United States Patent
Furst et al.

(10) Patent No.: US 7,648,591 B2
(45) Date of Patent: *Jan. 19, 2010

(54) METAL ALLOYS FOR MEDICAL DEVICES

(75) Inventors: Joseph G. Furst, Lyndhurst, OH (US); Udayan Patel, San Jose, CA (US); Raymond W. Buckman, Jr., Pittsburgh, PA (US)

(73) Assignee: ICON Medical Corp., Altanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/272,317

(22) Filed: Nov. 17, 2008

(65) Prior Publication Data

US 2009/0068249 A1    Mar. 12, 2009

Related U.S. Application Data

(63) Continuation of application No. 11/338,265, filed on Jan. 24, 2006, now Pat. No. 7,488,444, which is a continuation-in-part of application No. 11/282,461, filed on Nov. 18, 2005, now Pat. No. 7,452,502, said application No. 11/338,265 is a continuation-in-part of application No. 11/282,376, filed on Nov. 18, 2005, now Pat. No. 7,452,501.

(60) Provisional application No. 60/694,891, filed on Jun. 29, 2005, provisional application No. 60/658,226, filed on Mar. 3, 2005, provisional application No. 60/694,881, filed on Jun. 29, 2005, provisional application No. 60/739,688, filed on Nov. 23, 2005.

(51) Int. Cl.
    *C22C 27/00*      (2006.01)
    *A61F 2/06*      (2006.01)

(52) U.S. Cl. .................. 148/423; 148/407; 420/429; 420/433; 623/23.7

(58) Field of Classification Search .................. 148/423; 420/429, 433
See application file for complete search history.

(56) References Cited

U.S. PATENT DOCUMENTS

| | | | |
|---|---|---|---|
| 3,964,482 A | 6/1976 | Gerstel | |
| 5,059,205 A | 10/1991 | El-Nounov et al. | |
| 5,091,205 A | 2/1992 | Fan | |
| 5,226,909 A | 7/1993 | Evans et al. | |

(Continued)

FOREIGN PATENT DOCUMENTS

CA      2172187      6/2001

(Continued)

OTHER PUBLICATIONS

W.D. Klopp, Technology status of molybdenum and tungsten alloys, Space Nuclear Power Systems, Orbit Book Company, Malabar, FL, (1984), Ch. 42, p. 359-369.*

(Continued)

*Primary Examiner*—George Wyszomierski
*Assistant Examiner*—Mark L Shevin
(74) *Attorney, Agent, or Firm*—Fay Sharpe LLP; Brian E. Turung

(57) ABSTRACT

A medical device that is at least partially formed of a novel metal alloy, which novel metal alloy improves the physical properties of the medical device.

44 Claims, 6 Drawing Sheets

U.S. PATENT DOCUMENTS

| | | | |
|---|---|---|---|
| 5,252,288 A | | 10/1993 | Yamamoto et al. |
| 5,263,349 A | | 11/1993 | Felix et al. |
| 5,344,402 A | | 9/1994 | Crocker |
| 5,344,426 A | | 9/1994 | Lau et al. |
| 5,372,661 A | | 12/1994 | Felix |
| 5,437,744 A | * | 8/1995 | Carlen .................. 148/423 |
| 5,443,498 A | | 8/1995 | Fontaine |
| 5,605,696 A | | 2/1997 | Eury |
| 5,609,629 A | * | 3/1997 | Fearnot et al. ............. 623/1.42 |
| 5,628,787 A | | 5/1997 | Mayer |
| 5,632,840 A | | 5/1997 | Campbell |
| 5,649,977 A | | 7/1997 | Campbell |
| 5,755,770 A | | 5/1998 | Ravenscroft |
| 5,800,511 A | | 9/1998 | Mayer |
| 5,824,046 A | | 10/1998 | Smith et al. |
| 5,824,077 A | | 10/1998 | Mayer |
| 5,843,172 A | | 12/1998 | Yan |
| 5,891,191 A | | 4/1999 | Stinson |
| 5,916,263 A | | 6/1999 | Goicoechea et al. |
| 5,919,570 A | | 7/1999 | Hostettler et al. |
| 5,951,585 A | | 9/1999 | Cathcart et al. |
| 5,957,930 A | | 9/1999 | Vrba |
| 5,993,545 A | | 11/1999 | Lupton |
| 6,039,920 A | | 3/2000 | Koch |
| 6,102,979 A | | 8/2000 | Bianco et al. |
| 6,123,712 A | | 9/2000 | DiCaprio et al. |
| 6,137,060 A | | 10/2000 | Avellanet |
| 6,238,491 B1 | | 5/2001 | Davidson et al. |
| 6,240,616 B1 | | 6/2001 | Yan |
| 6,253,443 B1 | | 7/2001 | Johnson |
| 6,273,908 B1 | | 8/2001 | Ndondo-Lay |
| 6,290,721 B1 | | 9/2001 | Heath |
| 6,334,856 B1 | * | 1/2002 | Allen et al. ................ 604/191 |
| 6,379,380 B1 | | 4/2002 | Satz |
| 6,527,802 B1 | | 3/2003 | Mayer |
| 6,638,301 B1 | | 10/2003 | Chandrasekaren et al. |
| 6,702,849 B1 | | 3/2004 | Dutta et al. |
| 6,709,379 B1 | | 3/2004 | Brandau et al. |
| 6,723,120 B2 | | 4/2004 | Yan |
| 6,730,699 B2 | | 5/2004 | Li et al. |
| 6,749,554 B1 | | 6/2004 | Snow et al. |
| 6,764,505 B1 | | 7/2004 | Hossainy et al. |
| 6,790,218 B2 | | 9/2004 | Jayaraman |
| 6,790,372 B2 | | 9/2004 | Roy |
| 6,830,638 B2 | | 12/2004 | Boylan et al. |
| 6,865,810 B2 | | 3/2005 | Stinson |
| 6,920,677 B2 | | 7/2005 | Dolan et al. |
| 6,924,087 B2 | | 8/2005 | Yeshurun |
| 2001/0013166 A1 | | 8/2001 | Yan |
| 2002/0098278 A1 | | 7/2002 | Bates |
| 2002/0193865 A1 | | 12/2002 | Radisch |
| 2003/0040790 A1 | | 2/2003 | Furst |
| 2003/0077200 A1 | | 4/2003 | Craig |
| 2003/0100499 A1 | | 5/2003 | Epstein |
| 2003/0181972 A1 | | 9/2003 | Jansen |
| 2004/0000046 A1 | | 1/2004 | Stinson |
| 2004/0049261 A1 | * | 3/2004 | Xu ............................ 623/1.15 |
| 2004/0073291 A1 | | 4/2004 | Brown |
| 2004/0086674 A1 | | 5/2004 | Holman |
| 2004/0143317 A1 | | 7/2004 | Stinson |
| 2004/0230290 A1 | | 11/2004 | Weber |
| 2004/0243225 A1 | | 12/2004 | Ragheb |
| 2004/0265615 A1 | | 12/2004 | Kodas |
| 2005/0092507 A1 | | 5/2005 | Marshall |
| 2005/0131522 A1 | | 6/2005 | Stinson |
| 2005/0150096 A1 | | 7/2005 | Stinson |
| 2005/0182482 A1 | | 8/2005 | Wang |
| 2005/0216075 A1 | | 9/2005 | Wang |
| 2005/0238522 A1 | | 10/2005 | Leonhardt et al. |
| 2006/0136051 A1 | | 6/2006 | Furst et al. |
| 2007/0003753 A1 | | 1/2007 | Asgari |

FOREIGN PATENT DOCUMENTS

| | | |
|---|---|---|
| EP | 734721 | 2/1996 |
| EP | 714640 | 6/1996 |
| EP | 756853 | 2/1997 |
| RU | 333209 | 6/2006 |
| WO | WO 93/19803 | 10/1993 |
| WO | WO 95/30384 | 11/1995 |
| WO | WO 01/41678 | 6/2001 |

OTHER PUBLICATIONS

A.J. Mueller, et al, Evaluation of oxide dispersion strengthened (ODS) molybdenum and molybdenum-rhenium alloys, B-T-3148, (1999), p. 1-18.*

Refractory Metals Forum: Rhenium and Its Alloys, B.D. Bryskin Sep. 1992.

The Effect of Annealing Practice on the Structure and Mechanical Properties of P/M MO—47.5% Re Alloy, John A. Shields, Jr. CLI-MAX Specialty Metals, Cleveland, OH 44117.

Delute Mo-Re Alloys—A Critical Evaluation of Their Comparative Mechanical Properties, J. Watsworth, T.T. Nieg, and J.J. Stephens Dec. 6, 1985.

Technology Status of Molybdenum and Tungsten Alloys, W.D. Klopp, Materials Consultant, 1542 Mendelssohn Dr., Westlake, OH 44145 1985.

The Alloys of Rhenium with Molybdenum or with Tungsten and Having Good High Temperature Properties, G.A. Geach and J.E. Hughes. 1956.

Behaviour of Tungsten, Molybdenum, and Alloys under Unusual Heating Conditions, Ralf Eck, Hubert Bildstein, Fritz Simader, Roland Stickler, Josef Tinzl 1989.

Rhenium and Molybdenum/Tungsten Based Alloys: An Overview of Database, Boris D. Bryskin and Jan C. Carlen 1998.

Mechanical Properties of Mo-Re Alloys at Different Test Temperatures, A.V. Abramyan, N.N. Morgunova, S.A. Golovanenko, and N.I. Kazakova 1988.

Needles, Sutures and Knots, Part III; Specific Suture Materials Al Sherbeeny,M., MD, vol. 1, Jul. 2004.

Microsystems for Drug and Gene Delivery, Michael L. Reed, Senior Member, IEEE & Whye-Kei Lye, Member, IEEE 2004.

Silicon Micromachined Hollow Microneedles for Transdermal Liquid Transport, Jan J.G.E. Gardeniers, Regina Luttge, Erwin J.W. Berenschot, Meint J. De Boer, Shuki Y. Yeshurun, Meir Hefetz, Ronnyb van't Oever, and Abert van den Berg, Journal of Microelectromechanical Systems, vol. 12, No. 6, Dec. 2003.

A New Method for the Estimation for the Absorption Time of Bioabsorbable Polymers in the Body, D.C.tunc, M. Gockbora and P.Higham/ Stryker Howmedica Osteonics, Advanced Technology Group, Mahwa, NJ 07430 USA vol. 15, No. 6, Jun. 2002.

Synthesis and comparative biodegradability studies of three poly(alkylene succinate)s. D. Bikiaris, G. Papageorgiou, D. Achilias, Laboratory of Organic Chemical Technology, Dept. of Chemistry, Aristotle University of Thessaloniki, GR-541 24, Thessaloniki, Macedonia, Greece 2006.

Leonhardt et al., "Investigation of Mechanical Properties and Microstructure of Various Molybdenum-Rhenium Alloys", AIP Conference Proceedings, vol. 458, p. 685, 1999.

Freund et al., "Stress-Rupture Strength and Creep Behaviour on Molybdenum-Rhenium Alloys", TMS $129^{th}$ Annual Meeting & Exhibtion, Mar. 12-16, 2000.

A.J. Mueller et al., Evaluation of oxide dispersion strengthened (ODS) molybdenum and molybdenum-rhenium alloys, B-T-3148M (1999), p. 1-18.

Metals handbook Desk Edition, $2^{nd}$ Edition. Copyright 1998 by ASM Intl.

* cited by examiner

METAL ALLOYS FOR MEDICAL DEVICES

The present invention is a continuation of U.S. patent application Ser. No. 11/338,265 filed Jan. 24, 2006 now U.S. Pat. No. 7,488,444, which in turn is a continuation-in-part of U.S. patent application Ser. No. 11/282,461 filed Nov. 18, 2005 now U.S. Pat. No. 7,452,502 entitled "Metal Alloy for a Stent" which claims priority on U.S. Provisional Application Ser. No. 60/694,891 filed Jun. 29, 2005 entitled "Improved Metal Alloys for Medical Devices", all of which are incorporated herein by reference.

The present invention is also a continuation of U.S. patent application Ser. No. 11/338,265 filed Jan. 24, 2006, which in turn is a continuation-in-part of U.S. patent application Ser. No. 11/282,376 filed Nov. 18, 2005 now U.S. Pat. No. 7,452,501 entitled "Metal Alloy for a Stent, which is incorporated herein by reference.

The present invention is also a continuation of U.S. patent application Ser. No. 11/338,265 filed Jan. 24, 2006, which in turn claims priority on U.S. Provisional Application Ser. Nos. 60/658,226 filed Mar. 3, 2005 entitled "Improved Metal Alloys for Medical Devices"; 60/694,881 filed Jun. 29, 2005 entitled "Improved Metal Alloys for Medical Devices"; and 60/739,688 filed Nov. 23, 2005 entitled "Process for Forming an Improved Metal Alloy Stent", all of which are incorporated herein by reference.

The invention relates generally to medical devices, and particularly to a medical device that is at least partially formed of a novel molybdenum and rhenium metal alloy, and more particularly to a graft that is at least partially formed of a novel molybdenum and rhenium metal and which graft is coating with one or more biological agents for use in treating a body passageway.

BACKGROUND OF THE INVENTION

Medical treatment of various illnesses or diseases commonly includes the use of one or more medical devices. Two types of medical device that are commonly used to repair various types of body passageways are an expandable graft or stent, or a surgical graft. These devices have been implanted in various areas of the mammalian anatomy. One purpose of a stent is to open a blocked or partially blocked body passageway. When a stent is used in a blood vessel, the stent is used to open the occluded vessel to achieve improved blood flow which is necessary to provide for the anatomical function of an organ. The procedure of opening a blocked or partially blocked body passageway commonly includes the use of one or more stents in combination with other medical devices such as, but not limited to, an introducer sheath, a guiding catheter, a guide wire, an angioplasty balloon, etc.

Various physical attributes of a stent can contribute directly to the success rate of the device. These physical attributes include radiopacity, hoop strength, radial force, thickness of the metal, dimensions of the metal and the like. Cobalt and chromium and stainless steel are commonly used to form stents. These materials are commonly used since such materials having a known history of safety, effectiveness and biocompatibility. These materials however have limited physical performance characteristics as to size, strength, weight, bendability, biostability and radiopacity.

The present invention can be generally directed to a medical device such as, but not limited to, a stent that is at least partially formed of a novel metal alloy that improves the physical properties of the medical device thereby improving the success rate of such medical device.

SUMMARY OF THE INVENTION

The present invention is generally directed to a medical device that is at least partially made of a novel metal alloy having improved properties as compared to past medical devices. The novel metal alloy used to at least partially form the medical device improves one or more properties (e.g., strength, durability, hardness, biostability, bendability, coefficient of friction, radial strength, flexibility, tensile strength, tensile elongation, longitudinal lengthening, stress-strain properties, improved recoil properties, radiopacity, heat sensitivity, biocompatibility, etc.) of such medical device. These one or more improved physical properties of the novel metal alloy can be achieved in the medical device without having to increase the bulk, volume and/or weight of the medical device, and in some instances these improved physical properties can be obtained even when the volume, bulk and or weight of the medical device is reduced as compared to medical devices that are at least partially formed from traditional stainless steel or cobalt and chromium alloy materials. The novel metal alloy that is used to at least partially form the medical device can thus 1) increase the radiopacity of the medical device, 2) increase the radial strength of the medical device, 3) increase the yield strength and/or ultimate tensile strength of the medical device, 4) improve the stress-strain properties of the medical device, 5) improve the crimping and/or expansion properties of the medical device, 6) improve the bendability and/or flexibility of the medical device, 7) improve the strength and/or durability of the medical device, 8) increase the hardness of the medical device, 9) improve the longitudinal lengthening properties of the medical device, 10) improved the recoil properties of the medical device, 11) improve the friction coefficient of the medical device, 12) improve the heat sensitivity properties of the medical device, 13) improve the biostability and/or biocompatibility properties of the medical device, and/or 14) enable smaller, thinner and/or lighter weight medical devices to be made. The medical device generally includes one or more materials that impart the desired properties to the medical device so as to withstand the manufacturing processes that are needed to produce the medical device. These manufacturing processes can include, but are not limited to, laser cutting, etching, crimping, annealing, drawing, pilgering, electroplating, electro-polishing, chemical polishing, cleaning, pickling, ion beam deposition or implantation, sputter coating, vacuum deposition, etc.

In one non-limiting aspect of the present invention, a medical device that can include the novel metal alloy is a stent for use in a body passageway; however, it can be appreciated that other types of medical devices could be at least partially formed from the novel metal alloy. As used herein, the term "body passageway" is defined to be any passageway or cavity in a living organism (e.g., bile duct, bronchiole tubes, nasal cavity, blood vessels, heart, esophagus, trachea, stomach, fallopian tube, uterus, ureter, urethra, the intestines, lymphatic vessels, nasal passageways, eustachian tube, acoustic meatus, etc.). The techniques employed to deliver the medical device to a treatment area include, but are not limited to, angioplasty, vascular anastomoses, interventional procedures, and any combinations thereof. For vascular applications, the term "body passageway" primarily refers to blood vessels and chambers in the heart. The stent can be an expandable stent that is expandable by a balloon and/or other means. The stent can have many shapes and forms. Such shapes can include, but are not limited to, stents disclosed in U.S. Pat. Nos. 6,206,916 and 6,436,133; and all the prior art cited in these patents. These various designs and configurations of stents in such patents are incorporated herein by reference.

In another and/or alternative non-limiting aspect of the present invention, the medical device is generally designed to include at least about 25 weight percent of the novel metal alloy; however, this is not required. In one non-limiting embodiment of the invention, the medical device includes at least about 40 weight percent of the novel metal alloy. In another and or alternative non-limiting embodiment of the invention, the medical device includes at least about 50 weight percent of the novel metal alloy. In still another and/or alternative non-limiting embodiment of the invention, the medical device includes at least about 60 weight percent of the novel metal alloy. In yet another and, or alternative non-limiting embodiment of the invention, the medical device includes at least about 70 weight percent of the novel metal alloy. In still yet another and/or alternative non-limiting embodiment of the invention, the medical device includes at least about 85 weight percent of the novel metal alloy. In a further and/or alternative non-limiting embodiment of the invention, the medical device includes at least about 90 weight percent of the novel metal alloy. In still a further and/or alternative non-limiting embodiment of the invention, the medical device includes at least about 95 weight percent of the novel metal alloy. In yet a further and/or alternative non-limiting embodiment of the invention, the medical device includes about 100 weight percent of the novel metal alloy.

In still another and/or alternative non-limiting aspect of the present invention, the novel metal alloy that is used to form all or part of the medical device 1) is not clad, metal sprayed, plated and/or formed (e.g., cold worked, hot worked, etc.) onto another metal, or 2) does not have another metal or metal alloy metal sprayed, plated, clad and/or formed onto the novel metal alloy. It will be appreciated that in some applications, the novel metal alloy of the present invention may be clad, metal sprayed, plated and or formed onto another metal, or another metal or metal alloy may be plated, metal sprayed, clad and/or formed onto the novel metal alloy when forming all or a portion of a medical device.

In yet another and/or alternative non-limiting aspect of the present invention, the novel metal alloy that is used to form all or a portion of the medical device includes rhenium and molybdenum. The novel alloy can include one or more other metals such as, but not limited to, calcium, chromium, cobalt, copper, gold, iron, lead, magnesium, nickel, niobium, platinum, rare earth metals, silver, tantalum, titanium, tungsten, yttrium, zinc, zirconium, and/or alloys thereof.

In still another and/or alternative non-limiting aspect of the present invention, the novel metal alloy that is used to form all or a portion of the medical device is a novel metal alloy that includes at least about 90 weight percent molybdenum and rhenium. In one non-limiting composition, the content of molybdenum and rhenium in the novel metal alloy is at least about 95 weight percent. In another and/or alternative non-limiting composition, the content of molybdenum and rhenium in the novel metal alloy is at least about 97 weight percent. In still another and/or alternative non-limiting composition, the content of molybdenum and rhenium in the novel metal alloy is at least about 98 weight percent. In yet another and/or alternative non-limiting composition, the content of molybdenum and rhenium in the novel metal alloy is at least about 99 weight percent. In still yet another and/or alternative non-limiting composition, the content of molybdenum and rhenium in the novel metal alloy is at least about 99.5 weight percent. In a further one non-limiting composition, the content of molybdenum and rhenium in the novel metal alloy is at least about 99.9 weight percent. In still a further and/or alternative non-limiting composition, the content of molybdenum and rhenium in the novel metal alloy is at least about 99.95 weight percent. In yet a further and/or alternative non-limiting composition, the content of molybdenum and rhenium in the novel metal alloy is at least about 99.99 weight percent. As can be appreciated, other weight percentages of the rhenium and molybdenum content of the novel metal alloy can be used. In one non-limiting composition, the purity level of the novel metal alloy is such so as to produce a solid solution of the novel metal alloy. A solid solution or homogeneous solution is defined as a metal alloy that includes two or more primary metals and the combined weight percent of the primary metals is at least about 95 weight percent, typically at least about 99 weight percent, more typically at least about 99.5 weight percent, even more typically at least about 99.8 weight percent, and still even more typically at least about 99.9 weight percent. A primary metal is a metal component of the metal alloy that is not a metal impurity. A solid solution of a novel metal alloy that includes rhenium and molybdenum as the primary metals is an alloy that includes at least about 95-99 weight percent rhenium and molybdenum. It is believed that a purity level of less than 95 weight percent molybdenum and rhenium adversely affects one or more physical properties of the metal alloy that are useful or desired in forming and/or using a medical device. In one embodiment of the invention, the rhenium content of the novel metal alloy in accordance with the present invention is at least about 40 weight percent. In one non-limiting composition, the rhenium content of the novel metal alloy is at least about 45 weight percent. In still another and, or alternative non-limiting composition, the rhenium content of the novel metal alloy is about 45-50 weight percent. In yet another and/or alternative non-limiting composition, the rhenium content of the novel metal alloy is about 47-48 weight percent. In still yet another and or alternative non-limiting composition, the rhenium content of the novel metal alloy is about 47.6-49.5 weight percent. As can be appreciated, other weight percentages of the rhenium content of the novel metal alloy can be used. In another and/or alternative embodiment of the invention, the molybdenum content of the novel metal alloy in accordance with the present invention is at least about 40 weight percent. In one non-limiting composition, the molybdenum content of the novel metal alloy is at least about 45 weight percent. In another and/or alternative non-limiting composition, the molybdenum content of the novel metal alloy is at least about 50 weight percent. In still another and/or alternative non-limiting composition, the molybdenum content of the novel metal alloy is about 50-60 percent. In yet another and, or alternative non-limiting composition, the molybdenum content of the novel metal alloy is about 50-56 weight percent. As can be appreciated, other weight percentages of the molybdenum content of the novel metal alloy can be used.

In still yet another and/or alternative non-limiting aspect of the present invention, the novel metal alloy that is used to form all or a portion of the medical device is a novel metal alloy that includes at least about 90 weight percent molybdenum and rhenium, and at least one additional metal which includes titanium, yttrium, and/or zirconium. The addition of controlled amounts of titanium, yttrium, and/or zirconium to the molybdenum and rhenium alloy has been found to form a metal alloy that has improved physical properties over a metal alloy that principally includes molybdenum and rhenium. For instance, the addition of controlled amounts of titanium, yttrium, and/or zirconium to the molybdenum and rhenium alloy can result in 1) an increase in yield strength of the alloy as compared to a metal alloy that principally includes molybdenum and rhenium, 2) an increase in tensile elongation of the alloy as compared to a metal alloy that principally includes molybdenum and rhenium, 3) an increase in ductility of the alloy as compared to a metal alloy that principally includes molybdenum and rhenium, 4) a reduction in grain size of the alloy as compared to a metal alloy that principally includes molybdenum and rhenium, 5) a reduction in the amount of free carbon, oxygen and/or nitrogen in the alloy as compared to a metal alloy that principally includes molybdenum and rhenium, and/or 6) a reduction in the tendency of the alloy to form micro-cracks during the forming of the alloy into a medical device as compared to the forming of a medical device from a metal alloy that principally includes molybdenum and rhenium. In one non-limiting composition, the content of molybdenum and rhenium and the at least one additional metal in the novel metal alloy is at least about 90 weight percent. In another and or alternative non-limiting composition, the content of molybdenum and rhenium and the at least one additional metal in the novel metal alloy is at least about 95 weight percent. In still another and/or alternative non-limiting composition, the content of molybdenum and rhenium and the at least one additional metal in the novel metal alloy is at least about 98 weight percent. In yet another and/or alternative non-limiting composition, the content of molybdenum and rhenium and the at least one additional metal in the novel metal alloy is at least about 99 weight percent. In still yet another and/or alternative non-limiting composition, the content of molybdenum and rhenium and the at least one additional metal in the novel metal alloy is at least about 99.5 weight percent. In a further one non-limiting composition, the content of molybdenum and rhenium and the at least one additional metal in the novel metal alloy is at least about 99.9 weight percent. In still a further and/or alternative non-limiting composition, the content of molybdenum and rhenium and the at least one additional metal in the novel metal alloy is at least about 99.95 weight percent. In yet a further and/or alternative non-limiting composition, the content of molybdenum and rhenium and the at least one additional metal in the novel metal alloy is at least about 99.99 weight percent. As can be appreciated, other weight percentages of the content of molybdenum and rhenium and the at least one additional metal in the novel metal alloy can be used. In one non-limiting composition, the purity level of the novel metal alloy is such so as to produce a solid solution of a rhenium and molybdenum and the at least one additional metal. A solid solution of a novel metal alloy that includes rhenium and molybdenum and the at least one additional metal of titanium, yttrium and/or zirconium as the primary metals is an alloy that includes at least about 95-99 weight percent rhenium and molybdenum and the at least one additional metal. It is believed that a purity level of less than 95 weight percent molybdenum and rhenium and the at least one additional metal adversely affects one or more physical properties of the metal alloy that are useful or desired in forming and/or using a medical device. In one embodiment of the invention, the rhenium content of the novel metal alloy in accordance with the present invention is at least about 40 weight percent. In one non-limiting composition, the rhenium content of the novel metal alloy is at least about 45 weight percent. In still another and/or alternative non-limiting composition, the rhenium content of the novel metal alloy is about 45-50 weight percent. In yet another and or alternative non-limiting composition, the rhenium content of the novel metal alloy is about 47-48 weight percent. As can be appreciated, other weight percentages of the rhenium content of the novel metal alloy can be used. In another and/or alternative embodiment of the invention, the molybdenum content of the novel metal alloy is at least about 40 weight percent. In one non-limiting composition, the molybdenum content of the novel metal alloy is at least about 45 weight percent. In another and/or alternative non-limiting composition, the molybdenum content of the novel metal alloy is at least about 50 weight percent. In still another and/or alternative non-limiting composition, the molybdenum content of the novel metal alloy is about 50-60 percent. In yet another and/or alternative non-limiting composition, the molybdenum content of the novel metal alloy is about 50-56 weight percent. As can be appreciated, other weight percentages of the molybdenum content of the novel metal alloy can be used. The combined content of titanium, yttrium and zirconium in the novel metal alloy is less than about 5 weight percent, typically no more than about 1 weight percent, and more typically no more than about 0.5 weight percent. A higher weight percent content of titanium, yttrium and/or zirconium in the novel metal alloy can begin to adversely affect the brittleness of the novel metal alloy. When titanium is included in the novel metal alloy, the titanium content is typically less than about 1 weight percent, more typically less than about 0.6 weight percent, even more typically about 0.05-0.5 weight percent, still even more typically about 0.1-0.5 weight percent. As can be appreciated, other weight percentages of the titanium content of the novel metal alloy can be used. When zirconium is included in the novel metal alloy, the zirconium content is typically less than about 0.5 weight percent, more typically less than about 0.3 weight percent, even more typically about 0.01-0.25 weight percent, still even more typically about 0.05-0.25 weight percent. As can be appreciated, other weight percentages of the zirconium content of the novel metal alloy can be used. When titanium and zirconium are included in the novel metal alloy, the weight ratio of titanium to zirconium is about 1-10:1, typically about 1.5-5:1, and more typically about 1.75-2.5:1. When yttrium is included in the novel metal alloy, the yttrium content is typically less than about 0.3 weight percent, more typically less than about 0.2 weight percent, and even more typically about 0.01-0.1 weight percent. As can be appreciated, other weight percentages of the yttrium content of the novel metal alloy can be used. The inclusion of titanium, yttrium and/or zirconium in the novel metal alloy is believed to result in a reduction of oxygen trapped in the solid solution of the novel metal alloy. The reduction of trapped oxygen enables the formation of a smaller grain size in the novel metal alloy and, or an increase in the ductility of the novel metal alloy. The reduction of trapped oxygen in the novel metal alloy can also increase the yield strength of the novel metal alloy as compared to alloys of only molybdenum and rhenium (i.e., 2-10% increase). The inclusion of titanium, yttrium and/or zirconium in the novel metal alloy is also believed to cause a reduction in the trapped free carbon in the novel metal alloy. The inclusion of titanium, yttrium and/or zirconium in the novel metal alloy is believed to form carbides with the free carbon in the novel metal alloy. This carbide formation is also believed to improve the ductility of the novel metal alloy and to also reduce the incidence of cracking during the forming of the metal alloy into a medical device (e.g., stent, etc.). As such, the novel metal alloy exhibits increased tensile elongation as compared to alloys of only molybdenum and rhenium (i.e., 1-8% increase). The inclusion of titanium, yttrium and/or zirconium in the novel metal alloy is also believed to cause a reduction in the trapped free nitrogen in the novel metal alloy. The inclusion of titanium, yttrium and/or zirconium in the novel metal alloy is believed to form carbo-nitrides with the free carbon and free nitrogen in the novel metal alloy. This carbo-nitride formation is also believed to improve the ductility of the novel metal alloy and to also reduce the incidence of cracking during the forming of the metal alloy into a medical device (e.g., stent, etc.). As such, the novel metal alloy exhibits increased tensile elongation as compared to alloys of only molybdenum and rhenium (i.e., 1-8% increase). The reduction in the amount of free carbon, oxygen and/or nitrogen in the novel metal alloy is also believed to increase the density of the novel metal alloy (i.e., 1-5% increase). The formation of carbides, carbo-nitrides, and/or oxides in the novel metal alloy results in the formation of dispersed second phase particles in the novel metal alloy, thereby facilitating in the formation of small grain sizes in the metal alloy.

In still another and/or alternative non-limiting aspect of the present invention, the novel metal alloy includes less than about 5 weight percent other metals and/or impurities. A high purity level of the novel metal alloy results in the formation of a more homogeneous alloy, which in turn results in a more uniform density throughout the novel metal alloy, and also results in the desired yield and ultimate tensile strengths of the novel metal alloy. The density of the novel metal alloy is generally at least about 12 gm/cc, and typically at least about 13-13.5 gm/cc. This substantially uniform high density of the novel metal alloy significantly improves the radiopacity of the novel metal alloy. In one non-limiting composition, the novel metal alloy includes less than about 1 weight percent other metals and/or impurities. In another and/or alternative non-limiting composition, the novel metal alloy includes less than about 0.5 weight percent other metals and/or impurities. In still another and or alternative non-limiting composition, the novel metal alloy includes less than about 0.4 weight percent other metals and or impurities. In yet another and/or alternative non-limiting composition, the novel metal alloy includes less than about 0.2 weight percent other metals and or impurities. In still yet another and/or alternative non-limiting composition, the novel metal alloy includes less than about 0.1 weight percent other metals and/or impurities. In a further and/or alternative non-limiting composition, the novel metal alloy includes less than about 0.05 weight percent other metals and/or impurities. In still a further and/or alternative non-limiting composition, the novel metal alloy includes less than about 0.02 weight percent other metals and/or impurities. In yet a further and/or alternative non-limiting composition, the novel metal alloy includes less than about 0.01 weight percent other metals and/or impurities. As can be appreciated, other weight percentages of the amount of other metals and/or impurities in the novel metal alloy can exist.

In yet another and/or alternative non-limiting aspect of the present invention, the novel metal alloy includes a certain amount of carbon and oxygen. These two elements have been found to affect the forming properties and brittleness of the novel metal alloy. The controlled atomic ratio of carbon and oxygen in the novel metal alloy also can be used to minimize the tendency of the novel metal alloy to form micro-cracks during the forming of the novel alloy into a medical device, and/or during the use and/or expansion of the medical device in a body passageway. In one non-limiting embodiment of the invention, the novel metal alloy includes up to about 200 ppm carbon and up to about 150 ppm oxygen. Higher carbon and oxygen contents in the novel metal alloy are believed to adversely affect one or more physical properties of the metal alloy that are useful or desired in forming and/or using a medical device. In one non-limiting formulation, the novel metal alloy includes up to about 150 ppm carbon. In still another and/or alternative non-limiting formulation, the novel metal alloy includes up to about 100 ppm carbon. In yet another and/or alternative non-limiting formulation, the novel metal alloy includes less than about 50 ppm carbon. In still yet another and/or alternative non-limiting formulation, the novel metal alloy includes up to about 100 ppm oxygen. In a further and or alternative non-limiting formulation, the novel metal alloy includes up to about 75 ppm oxygen. In still a further and/or alternative non-limiting formulation, the novel metal alloy includes up to about 50 ppm oxygen. In yet a further and/or alternative non-limiting formulation, the novel metal alloy includes up to about 30 ppm oxygen. In still yet a further and/or alternative non-limiting formulation, the novel metal alloy includes less than about 20 ppm oxygen. In yet a further and or alternative non-limiting formulation, the novel metal alloy includes less than about 10 ppm oxygen. As can be appreciated, other amounts of carbon and/or oxygen in the novel metal alloy can exist. In another and/or alternative non-limiting embodiment of the invention, the carbon to oxygen atomic ratio in the novel metal alloy is generally at least about 2:1 (i.e., weight ratio of about 1.5:1). The control of the atomic ratio of carbon to oxygen in the novel metal alloy allows for the redistribution of oxygen in the metal alloy so as to minimize the tendency of micro-cracking in the novel metal alloy during the forming of the novel alloy into a medical device, and/or during the use and/or expansion of the medical device in a body passageway. When the carbon to oxygen atomic ratio falls below 2-2.5:1 (i.e., weight ratio of about 1.5-1.88:1), the degree of elongation of the novel metal alloy decreases and the incidence of micro-cracking increases, thus adversely affecting one or more physical properties of the metal alloy that are useful or desired in forming and/or using the medical device. In one non-limiting formulation, the carbon to oxygen atomic ratio in the novel metal alloy is generally at least about 2.5:1 (i.e., weight ratio of about 1.88:1). In another and/or alternative non-limiting formulation, the carbon to oxygen atomic ratio in the novel metal alloy is generally at least about 3:1 (i.e., weight ratio of about 2.25:1). In still another and/or alternative non-limiting formulation, the carbon to oxygen atomic ratio in the novel metal alloy is generally at least about 4:1 (i.e., weight ratio of about 3:1). In yet another and/or alternative non-limiting formulation, the carbon to oxygen atomic ratio in the novel metal alloy is generally at least about 5:1 (i.e., weight ratio of about 3.75:1). In still yet another and/or alternative non-limiting formulation, the carbon to oxygen atomic ratio in the novel metal alloy is generally about 2.5-50:1 (i.e., weight ratio of about 1.88-37.54:1). In a further and/or alternative non-limiting formulation, the carbon to oxygen atomic ratio in the novel metal alloy is generally about 2.5-20:1 (i.e., weight ratio of about 1.88-15:1). In still a further and/or alternative non-limiting formulation, the carbon to oxygen atomic ratio in the novel metal alloy is generally about 2.5-10:1 (i.e., weight ratio of about 1.88-7.5:1). In yet a further and/or alternative non-limiting formulation, the carbon to oxygen atomic ratio in the novel metal alloy is generally about 2.5-5:1 (i.e., weight ratio of about 1.88-3.75:1). As can be appreciated, other atomic ratios of the carbon to oxygen in the novel metal alloy can be used.

In still yet another and/or alternative non-limiting aspect of the present invention, the novel metal alloy includes a controlled amount of nitrogen. Large amounts of nitrogen in the novel metal alloy can adversely affect the ductility of the novel metal alloy. This can in turn adversely affect the elongation properties of the novel metal alloy. A nitrogen content in the novel metal alloy of over 20 ppm can begin to cause the ductility of the novel metal alloy to unacceptably decrease, thus adversely affect one or more physical properties of the metal alloy that are useful or desired in forming and/or using the medical device. In one non-limiting embodiment of the invention, the novel metal alloy includes less than about 30 ppm nitrogen. In one non-limiting formulation, the novel metal alloy includes less than about 25 ppm nitrogen. In still another and/or alternative non-limiting formulation, the novel metal alloy includes less than about 10 ppm nitrogen. In yet another and/or alternative non-limiting formulation, the novel metal alloy includes less than about 5 ppm nitrogen. As can be appreciated, other amounts of nitrogen in the novel metal alloy can exist.

In a further and/or alternative non-limiting aspect of the present invention, the novel metal alloy has several physical properties that positively affect the medical device when at least partially formed of the novel metal alloy. In one non-limiting embodiment of the invention, the average hardness of the novel metal alloy tube used to form the medical device is generally at least about 60 (HRC) at 77° F. In one non-limiting aspect of this embodiment, the average hardness of the novel metal alloy tube used to form the medical device is generally at least about 70 (HRC) at 77° F., and typically about 80-100 (HRC) at 77° F. In another and/or alternative non-limiting embodiment of the invention, the average ultimate tensile strength of the novel metal alloy used to form the medical device is generally at least about 60 UTS (ksi). In non-limiting aspect of this embodiment, the average ultimate tensile strength of the novel metal alloy used to form the medical device is generally at least about 70 UTS (ksi), typically about 80-150 UTS (ksi), and more typically about 100-150 UTS (ksi). In still another and/or alternative non-limiting embodiment of the invention, the average yield strength of the novel metal alloy used to form the medical device is at least about 70 ksi. In one non-limiting aspect of this embodiment, the average yield strength of the novel metal alloy used to form the medical device is at least about 80 ksi, and typically about 100-140 (ksi). In yet another and/or alternative non-limiting embodiment of the invention, the average grain size of the novel metal alloy used to form the medical device is greater than 5 ASTM (e.g., ASTM E 112-96). The small grain size of the novel metal alloy enables the medical device to have the desired elongation and ductility properties that are useful in enabling the medical device to be formed, crimped and or expanded. In one non-limiting aspect of this embodiment, the average grain size of the novel metal alloy used to form the medical device is about 5.2-10 ASTM, typically, about 5.5-9 ASTM, more typically about 6-9 ASTM, still more typically about 6-8 ASTM, even more typically, about 6-7 ASTM, and still even more typically about 6.5-7 ASTM. In still yet another and/or alternative non-limiting embodiment of the invention, the average tensile elongation of the novel metal alloy used to form the medical device is at least about 25%. An average tensile elongation of at least 25% for the novel metal alloy is important to enable the medical device to be properly expanded when positioned in the treatment area of a body passageway. A medical device that does not have an average tensile elongation of at least about 25% can form micro-cracks and/or break during the forming, crimping and/or expansion of the medical device. In one non-limiting aspect of this embodiment, the average tensile elongation of the novel metal alloy used to form the medical device is about 25-35%. The unique combination of the rhenium content in the novel metal alloy in combination with achieving the desired purity and composition of the alloy and the desired grain size of the novel metal alloy results in 1) a medical device having the desired high ductility at about room temperature, 2) a medical device having the desired amount of tensile elongation, 3) a homogeneous or solid solution of a metal alloy having high radiopacity, 4) a reduction or prevention of microcrack formation and/or breaking of the metal alloy tube when the metal alloy tube is sized and/or cut to form the medical device, 5) a reduction or prevention of microcrack formation and/or breaking of the medical device when the medical device is crimped onto a balloon and/or other type of medical device for insertion into a body passageway, 6) a reduction or prevention of microcrack formation and/or breaking of the medical device when the medical device is bent and/or expanded in a body passageway, 7) a medical device having the desired ultimate tensile strength and yield strength, 8) a medical device that can have very thin wall thicknesses and still have the desired radial forces needed to retain the body passageway on an open state when the medical device has been expanded, and/or 9) a medical device that exhibits less recoil when the medical device is crimped onto a delivery system and/or expanded in a body passageway.

Several non-limiting examples of the novel metal alloy in accordance with the present invention are set forth below:

| Metal/Wt. % | Ex. 1 | Ex. 2 | Ex. 3 |
|---|---|---|---|
| C | ≦150 ppm | ≦150 ppm | ≦150 ppm |
| Mo | 50-60% | 50-60% | 50-55% |
| O | ≦100 ppm | ≦100 ppm | ≦100 ppm |
| N | ≦40 ppm | ≦40 ppm | ≦40 ppm |
| Re | 40-50% | 40-50% | 45-50% |
| Ti | ≦0.5% | ≦0.5% | ≦0.5% |
| Y | ≦0.1% | ≦0.1% | ≦0.1% |
| Zr | ≦0.25% | ≦0.25% | ≦0.25% |

| Metal/Wt. % | Ex. 4 | Ex. 5 | Ex. 6 |
|---|---|---|---|
| C | ≦150 ppm | ≦150 ppm | ≦150 ppm |
| Ca | 0% | 0% | 0% |
| Mg | 0% | 0% | 0% |
| Mo | 50-60% | 50-60% | 50-55% |
| O | ≦100 ppm | ≦100 ppm | ≦100 ppm |
| N | ≦40 ppm | ≦40 ppm | ≦40 ppm |
| Nb | 0% | ≦5% | 0% |
| Rare Earth Metal | 0% | ≦4% | 0% |
| Re | 40-50% | 40-50% | 45-50% |
| Ta | 0% | ≦3% | 0% |
| Ti | 0% | ≦1% | 0% |
| W | 0% | ≦3% | 0% |
| Y | 0% | ≦0.1% | 0% |
| Zn | 0% | ≦0.1% | 0% |
| Zr | 0% | ≦2% | 0% |

| Metal/Wt. % | Ex. 7 | Ex. 8 | Ex. 9 |
|---|---|---|---|
| C | ≦150 ppm | ≦150 ppm | ≦150 ppm |
| Ca | 0% | 0% | 0% |
| Mg | 0% | 0% | 0% |
| Mo | 52-55.5% | 51-58% | 50-56% |
| O | ≦100 ppm | ≦100 ppm | ≦100 ppm |
| N | ≦20 ppm | ≦20 ppm | ≦20 ppm |
| Rare Earth Metal | 0% | 0% | 0% |
| Re | 44.5-48% | 42-49% | 44-50% |
| Ta | 0% | 0% | 0% |
| Ti | 0% | 0% | 0% |
| W | 0% | 0% | 0% |
| Y | 0% | 0% | 0% |
| Zn | 0% | 0% | 0% |
| Zr | 0% | 0% | 0% |

In examples 1-9 above, the novel metal alloy is principally formed of rhenium and molybdenum. The novel metal alloy may also include controlled amounts of titanium, yttrium and/or zirconium. The content of other metals and or impurities is less than about 0.2 weight percent of the novel metal alloy. In the examples above, the ratio of carbon to oxygen is at least about 2.5:1 (i.e., weight ratio of carbon to oxygen of at least about 1.88:1), and the average grain size of novel metal alloy is about 6-10 ASTM.

Additional non-limiting examples of the novel metal alloy in accordance with the present invention are set forth below:

| Metal/Wt. % | Ex. 10 | Ex. 11 | Ex. 12 |
|---|---|---|---|
| C | ≦150 ppm | ≦50 ppm | ≦50 ppm |
| Mo | 51-54% | 52.5-55.5% | 50.5-52.4% |
| O | ≦50 ppm | ≦10 ppm | ≦10 ppm |
| N | ≦20 ppm | ≦10 ppm | ≦10 ppm |
| Re | 46-49% | 44.5-47.5% | 47.6-49.5% |

| Metal/Wt. % | Ex. 13 | Ex. 14 | Ex. 15 | Ex. 16 |
|---|---|---|---|---|
| C | ≦50 ppm | ≦50 ppm | ≦50 ppm | ≦50 ppm |
| Mo | 51-54% | 52.5-55.5% | 52-56% | 52.5-55% |
| O | ≦20 ppm | ≦20 ppm | ≦10 ppm | ≦10 ppm |
| N | ≦20 ppm | ≦20 ppm | ≦10 ppm | ≦10 ppm |
| Re | 46-49% | 44.5-47.5% | 44-48% | 45-47.5% |
| Ti | ≦0.4% | ≦0.4% | 0.2-0.4% | 0.3-0.4% |
| Y | ≦0.1% | ≦0.1% | 0-0.08% | 0.005-0.05% |
| Zr | ≦0.2% | ≦0.2% | 0-0.2% | 0.1-0.25% |

| Metal/Wt. % | Ex. 17 | Ex. 18 | Ex. 19 | Ex. 20 |
|---|---|---|---|---|
| C | ≦40 ppm | ≦40 ppm | ≦40 ppm | ≦40 ppm |
| Mo | 50.5-53% | 51.5-54% | 52-55% | 52.5-55% |
| O | ≦15 ppm | ≦15 ppm | ≦15 ppm | ≦10 ppm |
| N | ≦10 ppm | ≦10 ppm | ≦10 ppm | ≦10 ppm |
| Re | 47-49.5% | 46-48.5% | 45-48% | 45-47.5% |
| Ti | 0.1-0.35% | 0% | 0% | 0.1-0.3% |
| Y | 0% | 0.002-0.08% | 0% | 0% |
| Zr | 0% | 0% | 00.1-0.2% | 0.05-0.15% |

| Metal/Wt. % | Ex. 21 | Ex. 22 |
|---|---|---|
| C | ≦40 ppm | ≦40 ppm |
| Mo | 52-55% | 52.5-55.5% |
| O | ≦10 ppm | ≦10 ppm |
| N | ≦10 ppm | ≦10 ppm |
| Re | 45-49% | 44.5-47.5% |
| Ti | 0.05-0.4% | 0% |
| Y | 0.005-0.07% | 0.004-0.06% |
| Zr | 0% | 0.1-0.2% |

In examples 10-12 above, the novel metal alloy is principally formed of rhenium and molybdenum and the content of other metals and/or impurities is less than about 0.1 weight percent of the novel metal alloy, the atomic ratio of carbon to oxygen is about 2.5-10:1 (i.e., weight ratio of about 1.88-7.5:1), the average grain size of the novel metal alloy is about 6-9 ASTM, the tensile elongation of the metal alloy is about 25-35%, the average density of the metal alloy is at least about 13.4 gm/cc, the average yield strength of the metal alloy is about 98-122 (ksi), the average ultimate tensile strength of the metal alloy is about 100-150 UTS (ksi), and the average hardness of the metal alloy is about 80-100 (HRC) at 77° F. In examples 13-22 above, the novel metal alloy is principally formed of rhenium and molybdenum and at least one metal of titanium, yttrium and or zirconium, and the content of other metals and or impurities is less than about 0.1 weight percent of the novel metal alloy, the ratio of carbon to oxygen is about 2.5-10:1, the average grain size of the novel metal alloy is about 6-9 ASTM, the tensile elongation of the metal alloy is about 25-35%, the average density of the metal alloy is at least about 13.6 gm/cc, the average yield strength of the metal alloy is at least about 110 (ksi), the average ultimate tensile strength of the metal alloy is about 100-150 UTS (ksi), and the average hardness of the metal alloy is about 80-100 (HRC) at 77° F.

In another and/or alternative non-limiting aspect of the present invention, the use of the novel metal alloy in the medical device can increase the strength of the medical device as compared with stainless steel or chromium-cobalt alloys, thus less quantity of novel metal alloy can be used in the medical device to achieve similar strengths as compared to medical devices formed of different metals. As such, the resulting medical device can be made smaller and less bulky by use of the novel metal alloy without sacrificing the strength and durability of the medical device. Such a medical device can have a smaller profile, thus can be inserted in smaller areas, openings and or passageways. The novel metal alloy also can increase the radial strength of the medical device. For instance, the thickness of the walls of the medical device and/or the wires used to form the medical device can be made thinner and achieve a similar or improved radial strength as compared with thicker walled medical devices formed of stainless steel or cobalt and chromium alloy. The novel metal alloy also can improve stress-strain properties, bendability and flexibility of the medical device, thus increase the life of the medical device. For instance, the medical device can be used in regions that subject the medical device to bending. Due to the improved physical properties of the medical device from the novel metal alloy, the medical device has improved resistance to fracturing in such frequent bending environments. In addition or alternatively, the improved bendability and flexibility of the medical device due to the use of the novel metal alloy can enable the medical device to be more easily inserted into a body passageway. The novel metal alloy can also reduce the degree of recoil during the crimping and or expansion of the medical device. For example, the medical device better maintains its crimped form and/or better maintains its expanded form after expansion due to the use of the novel metal alloy. As such, when the medical device is to be mounted onto a delivery device when the medical device is crimped, the medical device better maintains its smaller profile during the insertion of the medical device in a body passageway. Also, the medical device better maintains its expanded profile after expansion so as to facilitate in the success of the medical device in the treatment area. In addition to the improved physical properties of the medical device by use of the novel metal alloy, the novel metal alloy has improved radiopaque properties as compared to standard materials such as stainless steel or cobalt-chromium alloy, thus reducing or eliminating the need for using marker materials on the medical device. For instance, the novel metal alloy is at least about 10-20% more radiopaque than stainless steel or cobalt-chromium alloy. Specifically, the novel metal alloy can be at least about 33% more radiopaque than cobalt-chromium alloy and at least about 41.5% more radiopaque than stainless steel.

In still yet another and/or alternative non-limiting aspect of the present invention, the medical device that is at least partially formed from the novel metal alloy can be formed by a variety of manufacturing techniques. In one non-limiting embodiment of the invention, the medical device can be formed from a rod or tube of the novel metal alloy. If a solid rod of the novel metal alloy is formed, the rod can be drilled (e.g., gun drilled, EDM, etc.) to form a cavity or passageway partially or fully through the rod. The rod or tube can be cleaned, polished, annealed, drawn, etc. to obtain the desired diameter and/or wall thickness of the metal tube. After the metal tube has been formed to the desired diameter and wall thickness, the metal tube can be formed into a medical device by a process such as, but not limited to, laser cutting, etching, etc. After the medical device has been formed, the medical device can be cleaned, polished, sterilized, etc. for final processing of the medical device. As can be appreciated, other or additional process steps can be used to at least partially form the medical device from the novel metal alloy.

In a further and/or alternative non-limiting aspect of the present invention, the novel alloy used to at least partially form the medical device is initially formed into a rod or a tube of novel metal alloy. The novel metal alloy rod or tube can be formed by various techniques such as, but not limited to, 1) melting the novel metal alloy and/or metals that form the novel metal alloy (e.g., vacuum arc melting, etc.) and then extruding and/or casting the novel metal alloy into a rod or tube, 2) melting the novel metal alloy and/or metals that form the novel metal alloy, forming a metal strip and then rolling and welding the strip into a tube, or 3) consolidating metal power of the novel metal alloy and/or metal powder of metals that form the novel metal alloy. In one non-limiting process, the rod or tube of the novel metal alloy is formed by consolidating metal power. In this process, fine particles of molybdenum and rhenium along with any additives are mixed to form a homogenous blend of particles. Typically, the average particle size of the metal powders is less than about 200 mesh (e.g., less than 74 microns). A larger average particle size can interfere with the proper mixing of the metal powders and/or adversely affect one or more physical properties of the rod or tube formed from the metal powders. In one non-limiting embodiment, the average particle size of the metal powders is less than about 230 mesh (e.g., less than 63 microns). In another and/or alternative non-limiting embodiment, the average particle size of the metal powders is about 230-635 mesh (i.e., about 20-63 microns). As can be appreciated, smaller average particle sizes can be used. The purity of the metal powders should be selected so that the metal powders contain very low levels of carbon, oxygen and nitrogen. Typically the carbon content of the molybdenum metal powder is less than about 100 ppm, the oxygen content of the molybdenum metal powder is less than about 50 ppm, and the nitrogen content of the molybdenum metal powder is less than about 20 ppm. Typically, the carbon content of the rhenium metal powder is less than about 100 ppm, the oxygen content of the rhenium metal powder is less than about 50 ppm, and the nitrogen content of the rhenium metal powder is less than about 20 ppm. Typically, metal powder having a purity grade of at least 99.9 and more typically at least about 99.95 should be used to obtain the desired purity of the powders of molybdenum and rhenium. When titanium, yttrium and/or zirconium powder is added to the metal powder mixture, the amount of carbon, oxygen and nitrogen in the power should also be minimized. Typically, metal powder having a purity grade of at least 99.8 and more typically at least about 99.9 should be used to obtain the desired purity of the powders of titanium, yttrium and/or zirconium. The blend of metal powder is then pressed together to form a solid solution of the novel metal alloy into a rod or tube. Typically, the pressing process is by an isostatic process (i.e., uniform pressure applied from all sides on the metal powder). When the metal powders are pressed together isostatically, cold isostatic pressing (CIP) is typically used to consolidate the metal powders; however, this is not required. The pressing process can be preformed in an inert atmosphere, an oxygen reducing atmosphere (e.g., hydrogen, argon and hydrogen mixture, etc.) and/or under a vacuum; however, this is not required. The average density of the rod or tube that is achieved by pressing together the metal powders is about 80-90% of the final average density of the rod or tube or about 70-95% the minimum theoretical density of the novel metal alloy. After the metal powders are pressed together, the pressed metal powders are sintered at high temperature (e.g. 2000-2500° C.) to fuse the metal powders together to form the solid metal rod or tube. The sintering of the consolidated metal powder can be preformed in an oxygen reducing atmosphere (e.g., hydrogen, argon and hydrogen mixture, etc.) and/or under a vacuum; however, this is not required. At the high sintering temperatures, a high hydrogen atmosphere will reduce both the amount of carbon and oxygen in the formed rod or tube. The sintered metal powder generally has an as-sintered average density of about 90-99% the minimum theoretical density of the novel metal alloy. Typically, the sintered rod or tube has a final average density of at least about 12 gm/cc, typically at least about 12.5 gm/cc, and more typically about 13-14 gm/cc. Typically, the rod or tube is formed to have a length of about 48 inches or less, however, longer lengths can be formed. A rod or tube formed by this process typically has an average concentricity deviation that is less than a rod or tube formed by an arc melting and molding process and a sheet and welding process. Generally, the average concentricity deviation of the rod or tube that is formed from compressed and sintered metal powders is less than about 20%, typically about 1-18%, and more typically about 1-5%. The average outer diameter of the rod or tube is typically less than about 2 inches, more typically less than about 1 inch, and even more typically no more than about 0.5 inch; however, larger tube sizes can be formed. In one non-limiting tube configuration, the tube has an inner diameter of about 0.31 inch plus or minus about 0.002 inch and an outer diameter of about 0.5 inch plus or minus about 0.002 inch. The wall thickness of the tube is about 0.095 inch plus or minus about 0.002 inch. As can be appreciated, this is just one example of many different sized tubes that can be formed.

In still a further and/or alternative non-limiting aspect of the present invention, when a solid rod of the novel metal alloy is formed, the rod is then formed into a tube prior to reducing the diameter of the rod. The rod can be formed into a tube by a variety of processes such as, but not limited to, drilling (e.g., gun drilling, etc.) or by cutting (e.g., EDM, etc.). The cavity or passageway formed in the rod typically is formed fully through the rod; however, this is not required.

In yet a further and/or alternative non-limiting aspect of the present invention, the rod or tube can be cleaned and/or polished after the rod or tube has been formed; however, this is not required. Typically, the rod or tube is cleaned and/or polished prior to being further processed; however, this is not required. When a rod of the novel metal alloy is formed into a tube, the formed tube is typically cleaned and/or polished prior to being further process; however, this is not required. When the rod or tube is resized and/or annealed as discussed in detail below, the resized and/or annealed rod or tube is typically cleaned and/or polished prior to and/or after each or after a series of resizing and/or annealing processes; however, this is not required. The cleaning and/or polishing of the rod or tube is used to remove impurities and/or contaminants from the surfaces of the rod or tube. Impurities and contaminants can become incorporated into the novel metal alloy during the processing of the rod or tube. The inadvertent incorporation of impurities and contaminants in the rod or tube can result in an undesired amount of carbon, nitrogen and/or oxygen, and/or other impurities in the novel metal alloy. The inclusion of impurities and contaminants in the novel metal alloy can result in premature micro-cracking of the novel metal alloy and/or an adverse affect on one or more physical properties of the novel metal alloy (e.g., decrease in tensile elongation, increased ductility, etc.). The cleaning of the novel metal alloy can be accomplished by a variety of techniques such as, but not limited to, 1) using a solvent (e.g., acetone, methyl alcohol, etc.) and wiping the novel metal alloy with a Kimwipe or other appropriate towel, 2) by at least partially dipping or immersing the novel metal alloy in a solvent and then ultrasonically cleaning the novel metal alloy, and/or 3) by at least partially dipping or immersing the novel metal alloy in a pickling solution. As can be appreciated, the novel metal alloy can be cleaned in other or additional ways. If the novel metal alloy is to be polished, the novel metal alloy is generally polished by use of a polishing solution that typically includes an acid solution; however, this is not required. In one non-limiting example, the polishing solution includes sulfuric acid; however, other or additional acids can be used. In one non-limiting polishing solution, the polishing solution can include by volume 60-95% sulfuric acid and 5-40% de-ionized water (DI water). Typically, the polishing solution that includes an acid will increase in temperature during the making of the solution and/or during the polishing procedure. As such, the polishing solution is typically stirred and/or cooled during making of the solution and/or during the polishing procedure. The temperature of the polishing solution is typically about 20-100° C., and typically greater than about 25° C. One non-limiting polishing technique that can be used is an electro-polishing technique. When an electro-polishing technique is used, a voltage of about 2-30V, and typically about 5-12V is applied to the rod or tube during the polishing process, however, it will be appreciated that other voltages can be used. The time used to polish the novel metal alloy is dependent on both the size of the rod or tube and the amount of material that needs to be removed from the rod or tube. The rod or tube can be processed by use of a two-step polishing process wherein the novel metal alloy piece is at least partially immersed in the polishing solution for a given period (e.g., 0.1-15 minutes, etc.), rinsed (e.g., DI water, etc.) for a short period of time (e.g., 0.02-1 minute, etc.), and then flipped over and at least partially immersed in the solution again for the same or similar duration as the first time; however, this is not required. The novel metal alloy can be rinsed (e.g., DI water, etc.) for a period of time (e.g., 0.01-5 minutes, etc.) before rinsing with a solvent (e.g., acetone, methyl alcohol, etc.); however, this is not required. The novel metal alloy can be dried (e.g., exposure to the atmosphere, maintained in an inert gas environment, etc.) on a clean surface. These polishing procedures can be repeated until the desired amount of polishing of the rod or tube is achieved.

In still yet a further and/or alternative non-limiting aspect of the present invention, the rod or tube is resized to the desired dimension of the medical device. In one non-limiting embodiment, the diameter of the rod or tube is reduced to a final rod or tube dimension in a single step or by a series of steps. During the reduction a rod or tube, the outer rod or tube diameter, the inner rod or tube diameter and/or wall thickness of the rod or tube are typically reduced; however, this is not required. The outer diameter size of the rod or tube is typically reduced by the use of one or more drawing processes. During the drawing process, care should be taken to not form micro-cracks in the rod or tube during the reduction of the rod or tube outer diameter. Generally, the rod or tube should not be reduced in outer diameter by more about 25% each time the rod or tube is drawn through a reducing mechanism (e.g., a die, etc.). In one non-limiting process step, the rod or tube is reduced in outer diameter by about 0.1-20% each time the rod or tube is drawn through a reducing mechanism. In another and/or alternative non-limiting process step, the rod or tube is reduced in outer diameter by about 1-15% each time the rod or tube is drawn through a reducing mechanism. In still another and/or alternative non-limiting process step, the rod or tube is reduced in outer diameter by about 2-15% each time the rod or tube is drawn through reducing mechanism. In yet another one non-limiting process step, the rod or tube is reduced in outer diameter by about 5-10% each time the rod or tube is drawn through reducing mechanism. In another and/or alternative non-limiting embodiment of the invention, the rod or tube of novel metal alloy is drawn through a die to reduce the outer diameter of the rod or tube. The drawing process is typically a cold drawing process or a plug drawing process through a die. When a cold drawing or mandrel drawing process is used, a lubricant (e.g., grease, etc.) is typically coated on the outer surface of the rod or tube and the rod or tube is then drawn though the die. Typically, little or no heat is used during the cold drawing process. After the rod or tube has been drawn through the die, the outer surface of the rod or tube is typically cleaned with a solvent to remove the lubricant so as to limit the amount of impurities that are incorporated in the novel metal alloy. This cold drawing process can be repeated several times until the desired outer diameter, inner diameter and wall thickness of the rod or tube is achieved. A plug drawing process can also or alternatively be used to size the rod or tube. The plug drawing process typically does not use a lubricant during the drawing process. The plug drawing process typically includes a heating step to heat the rod or tube prior and/or during the drawing of the rod or tube through the die. The elimination of the use of a lubricant can reduce the incidence of impurities being introduced into the metal alloy during the drawing process. During the plug drawing process, the rod or tube can be protected from oxygen and nitrogen by use of a vacuum environment, an oxygen reducing environment (e.g., hydrogen, argon and hydrogen mixture, etc.) or an inert environment. One non-limiting protective environment includes argon, hydrogen or argon and hydrogen; however, other or additional inert gasses can be used. As indicated above, the rod or tube is typically cleaned after each drawing process to remove impurities and/or other undesired materials from the surface of the rod or tube; however, this is not required.

In still yet a further and/or alternative non-limiting aspect of the present invention, the rod or tube is annealed after one or more drawing processes. The metal alloy rod or tube can be annealed after each drawing process or after a plurality of drawing processes. The metal alloy rod or tube is typically annealed prior to about a 60% outer diameter size reduction of the metal alloy rod or tube. In other words, the rod or tube should not be reduced in outer diameter by more than 60% before being annealed. A too large of a reduction in the outer diameter of the metal alloy rod or tube during the drawing process prior to the rod or tube being annealed can result in micro-cracking of the rod or tube. In one non-limiting processing step, the metal alloy rod or tube is annealed prior to about a 50% outer diameter size reduction of the metal alloy rod or tube. In another and/or alternative non-limiting processing step, the metal alloy rod or tube is annealed prior to about a 45% outer diameter size reduction of the metal alloy rod or tube. In still another and/or alternative non-limiting processing step, the metal alloy rod or tube is annealed prior to about a 1-45% outer diameter size reduction of the metal alloy rod or tube. In yet another and/or alternative non-limiting processing step, the metal alloy rod or tube is annealed prior to about a 5-30% outer diameter size reduction of the metal alloy rod or tube. In still yet another and/or alternative non-limiting processing step, the metal alloy rod or tube is annealed prior to about a 5-15% outer diameter size reduction of the metal alloy rod or tube. When the rod or tube is annealed, the rod or tube is typically heated to a temperature of about 1300-1700° C. for a period of about 2-200 minutes; however, other temperatures and or times can be used. In one non-limiting processing step, the metal alloy rod or tube is annealed at a temperature of about 1400-1600° C. for about 2-30 minutes. The annealing process typically occurs in an inert environment or an oxygen reducing environment so as to limit the amount of impurities that may embed themselves in the novel metal alloy during the annealing process. One non-limiting oxygen reducing environment that can be used during the annealing process is a hydrogen environment; however, it can be appreciated that a vacuum environment can be used or one or more other or additional gasses can be used to create the oxygen reducing environment. At the annealing temperatures, a hydrogen containing atmosphere can further reduce the amount of oxygen in the rod or tube. The chamber in which the rod or tube is annealed should be substantially free of impurities (e.g., carbon, oxygen, and/or nitrogen) so as to limit the amount of impurities that can embed themselves in the rod or tube during the annealing process. The annealing chamber typically is formed of a material that will not impart impurities to the rod or tube as the rod or tube is being annealed. A non-limiting material that can be used to form the annealing chamber includes, but is not limited to, molybdenum, rhenium, tungsten, molybdenum TZM alloy, ceramic, etc. When the rod or tube is restrained in the annealing chamber, the restraining apparatuses that are used to contact the novel metal alloy rod or tube are typically formed of materials that will not introduce impurities to the novel metal alloy during the processing of the rod or tube. Non-limiting examples of materials that can be used to at least partially form the restraining apparatuses include, but are not limited to, molybdenum, titanium, yttrium, zirconium, rhenium and/or tungsten.

In another and/or alternative non-limiting aspect of the present invention, the rod or tube can be cleaned prior to and/or after being annealed. The cleaning process is designed to remove impurities and/or other materials from the surfaces of the rod or tube. Impurities that are on one or more surfaces of the rod or tube can become permanently embedded into the rod or tube during the annealing processes. These imbedded impurities can adversely affect the physical properties of the novel metal alloy as the rod or tube is formed into a medical device, and/or can adversely affect the operation and/or life of the medical device. In one non-limiting embodiment of the invention, the cleaning process includes a delubrication or degreasing process which is typically followed by pickling process; however, this is not required. The delubrication or degreasing process followed by pickling process are typically used when a lubricant has been used on the rod or tube during a drawing process. Lubricants commonly include carbon compounds and other types of compounds that can adversely affect the novel metal alloy if such compounds and/or elements in such compounds become associated and/or embedded with the novel metal alloy during an annealing process. The delubrication or degreasing process can be accomplished by a variety of techniques such as, but not limited to, 1) using a solvent (e.g., acetone, methyl alcohol, etc.) and wiping the novel metal alloy with a Kimwipe or other appropriate towel, and/or 2) by at least partially dipping or immersing the novel metal alloy in a solvent and then ultrasonically cleaning the novel metal alloy. As can be appreciated, the novel metal alloy can be delubricated or degreased in other or additional ways. After the novel metal alloy rod or tube has been delubricated or degreased, the rod or tube can be further cleaned by use of a pickling process. The pickling process, when used, includes the use of one or more acids to remove impurities from the surface of the rod or tube. Non-limiting examples of acids that can be used as the pickling solution include, but are not limited to, nitric acid, acetic acid, sulfuric acid, hydrochloric acid, and/or hydrofluoric acid. These acids are typically analytical reagent (ACS) grade acids. The acid solution and acid concentration are selected to remove oxides and other impurities on the rod or tube surface without damaging or over etching the surface of the rod or tube. A rod or tube surface that includes a large amount of oxides typically requires a stronger pickling solution and/or long picking process times. Non-limiting examples of pickling solutions include 1) 25-60% DI water, 30-60% nitric acid, and 2-20% sulfuric acid; 2) 40-75% acetic acid, 10-35% nitric acid, and 1-12% hydrofluoric acid; and 3) 50-100% hydrochloric acid. As can be appreciated, one or more different pickling solutions can be used during the pickling process. During the pickling process, the rod or tube is fully or partially immersed in the pickling solution for a sufficient amount of time to remove the impurities from the surface of the rod or tube. Typically, the time period for pickling is about 2-120 seconds; however, other time periods can be used. After the rod or tube has been pickled, the rod or tube is typically rinsed with a water (e.g., DI water, etc.) and/or a solvent (e.g., acetone, methyl alcohol, etc.) to remove any pickling solution from the rod or tube and then the rod or tube is allowed to dry. The rod or tube may be keep in an protective environment during the rinse and/or drying process to inhibit or prevent oxides from reforming on the surface of the rod or tube prior to the rod or tube being annealed; however, this is not required.

In yet another and/or alternative non-limiting aspect of the present invention, the restraining apparatuses that are used to contact the novel metal alloy rod or tube during an annealing process and or drawing process are typically formed of materials that will not introduce impurities to the novel metal alloy during the processing of the rod or tube. In one non-limiting embodiment, when the metal alloy rod or tube is exposed to temperatures above 150° C., the materials that contact the novel metal alloy rod or tube during the processing of the rod or tube are typically made from molybdenum, rhenium and/or tungsten. When the novel metal alloy rod or tube is processed at lower temperatures (i.e., 150° C. or less), materials made from Teflon parts can also or alternatively be used.

In still another and/or alternative non-limiting aspect of the present invention, the novel metal alloy rod or tube, after being formed to the desired outer diameter, inner diameter and/or wall thickness, can be cut and/or etched to at least partially form the desired configuration of the medical device (e.g., stent, etc.). In one non limiting embodiment of the invention, the novel metal alloy rod or tube is at least partially cut by a laser. The laser is typically desired to have a beam strength which can heat the novel metal alloy rod or tube to a temperature of at least about 2200-2300° C. In one non-limiting aspect of this embodiment, a pulsed YAGI-ND or $CO_2$ laser is used to at least partially cut a pattern of medical device out of the novel metal alloy rod or tube. In another and/or alternative non-limiting aspect of this embodiment, the cutting of the novel metal alloy rod or tube by the laser can occurs in a vacuum environment, an oxygen reducing environment, or an inert environment; however, this is not required. It has been found that laser cutting of the rod or tube in a non-protected environment can result in impurities being introduced into the cut rod or tube, which introduced impurities can induce micro-cracking of the rod or tube during the cutting of the rod or tube. One non-limiting oxygen reducing environment includes a combination of argon and hydrogen; however, a vacuum environment, an inert environment, or other or additional gasses can be used to form the oxygen reducing environment. In still another and/or alternative non-limiting aspect of this embodiment, the novel metal alloy rod or tube is stabilized so as to limit or prevent vibration of the rod or tube during the cutting process. The apparatus used to stabilize the rod or tube can be formed of molybdenum, rhenium, tungsten, molybdenum TZM alloy, ceramic, etc. so as to not introduce contaminants to the rod or tube during the cutting process; however, this is not required. Vibrations in the rod or tube during the cutting of the rod or tube can result in the formation of micro-cracks in the rod or tube as the rod or tube is cut. The average amplitude of vibration during the cutting of the rod or tube should be no more than about 150% the wall thickness of the rod or tube. In one non-limiting aspect of this embodiment, the average amplitude of vibration should be no more than about 100% the wall thickness of the rod or tube. In another non-limiting aspect of this embodiment, the average amplitude of vibration should be no more than about 75% the wall thickness of the rod or tube. In still another non-limiting aspect of this embodiment, the average amplitude of vibration should be no more than about 50% the wall thickness of the rod or tube. In yet another non-limiting aspect of this embodiment, the average amplitude of vibration should be no more than about 25% the wall thickness of the rod or tube. In still yet another non-limiting aspect of this embodiment, the average amplitude of vibration should be no more than about 15% the wall thickness of the rod or tube.

In still yet another and/or alternative non-limiting aspect of the present invention, the novel metal alloy rod or tube, after being formed to the desired medical device, can be cleaned, polished, sterilized, etc. for final processing of the medical device. In one non-limiting embodiment of the invention, the medical device is electropolished. In one non-limiting aspect of this embodiment, the medical device is cleaned prior to being exposed to the polishing solution; however, this is not required. The cleaning process, when used, can be accomplished by a variety of techniques such as, but not limited to, 1) using a solvent (e.g., acetone, methyl alcohol, etc.) and wiping the medical device with a Kimwipe or other appropriate towel, and/or 2) by at least partially dipping or immersing the medical device in a solvent and then ultrasonically cleaning the medical device. As can be appreciated, the medical device can be cleaned in other or additional ways. In another and/or alternative non-limiting aspect of this embodiment, the polishing solution can include one or more acids. One non-limiting formulation of the polishing solution includes about 10-80 percent by volume sulfuric acid. As can be appreciated, other polishing solution compositions can be used. In still another and/or alternative non-limiting aspect of this embodiment, about 5-12 volts are directed to the medical device during the electropolishing process; however, other voltage levels can be used. In yet another and/or alternative non-limiting aspect of this embodiment, the medical device is rinsed with water and/or a solvent and allowed to dry to remove polishing solution on the medical device.

In one non-limiting process for manufacturing a medical device in accordance with the present invention, the process includes the following process steps: 1) forming a novel metal alloy rod or tube; 2) resizing the rod or tube, 3) cleaning and/or pickling the surface of the rod or tube prior to annealing the rod or tube; 4) annealing the rod or tube; and 5) repeating steps 2-4 until the rod or tube has been sized to the desired size. In another and/or alternative non-limiting process for manufacturing a medical device in accordance with the present invention, the process includes the following process steps: 1) forming a novel metal alloy rod or tube; 2) resizing the rod or tube by use of a mandrel and/or plug drawing process, 3) cleaning and/or pickling the surface of the rod or tube prior to annealing the rod or tube; 4) annealing the rod or tube prior to a 60% outer diameter size reduction of the rod or tube; 5) repeating steps 2-4 until the rod or tube has been sized to the desired size; 6) cutting and/or etching the rod or tube to at least partially form the medical device; and 7) cleaning and/or electropolishing the medical device. In still another and/or alternative non-limiting process for manufacturing a medical device in accordance with the present invention, the process includes the following process steps: 1) consolidating metal power of the novel metal alloy and/or metal powder of metals that form the novel metal alloy into a tube; 2) resizing the tube one or more times by use of a plug drawing process, 3) cleaning and/or pickling the surface of the tube after each plug drawing process; 4) annealing the tube prior to a 45% outer diameter size reduction of the tube; 5) repeating steps 2-4 until the tube has been sized to the desired size; 6) laser cutting the tube to at least partially form the medical device; and 7) cleaning and/or electropolishing the medical device. As can be appreciated, other or additional process steps can be used to form the medical device from a novel metal alloy. In each of the non-limiting processes set forth above, the medical device can be further processed to include 1) a marker material, 2) one or more biological agents, 3) one or more polymer coatings, and/or 4) one or more surface or microstructures.

In yet another and/or alternative non-limiting aspect of the present invention, the medical device can include, contain and/or be coated with one or more biological agents that facilitate in the success of the medical device and/or treated area. The medical device can include, contain and/or be coated with one or more biological agents that inhibit or prevent in-stent restenosis, vascular narrowing, and/or thrombosis during and/or after the medical device is inserted into a treatment area; however, this is not required. In addition or alternatively, the medical device can include, contain and/or be coated with one or more biological agents that can be used in conjunction with the one or more biological agents that inhibit or prevent in-stent restenosis, vascular narrowing, and/or thrombosis that are included in, contained in and/or coated in the medical device. As such, the medical device, when it includes, contains, and/or is coated with one or more biological agents, can include one or more biological agents to address one or more medical needs. The term "biological agent" includes, but is not limited to, a substance, drug, or otherwise formulated and/or designed to prevent, inhibit and/or treat one or more biological problems, and/or to promote the healing in a treated area. Non-limiting examples of biological problems that can be addressed by one or more biological agents include, but are not limited to, viral, fungus and/or bacteria infection, vascular diseases and/or disorders; digestive diseases and/or disorders; reproductive diseases and/or disorders; lymphatic diseases and/or disorders, cancer; implant rejection; pain; nausea; swelling; arthritis; bone diseases and/or disorders; organ failure; immunity diseases and/or disorders; cholesterol problems; blood diseases and/or disorders, lung diseases and/or disorders; heart diseases and/or disorders; brain diseases and/or disorders; neuralgia diseases and/or disorders; kidney diseases and or disorders; ulcers; liver diseases and/or disorders; intestinal diseases and/or disorders; gallbladder diseases and/or disorders; pancreatic diseases and/or disorders; psychological disorders; respirator diseases and or disorders; gland diseases and/or disorders; skin diseases and/or disorders; hearing diseases and/or disorders; oral diseases and/or disorders; nasal diseases and/or disorders; eye diseases and/or disorders, fatigue; genetic diseases and/or disorders; burns; scarring and/or scars; trauma; weight diseases and/or disorders; addiction diseases and/or disorders; hair loss; cramps; muscle spasms; tissue repair; and/or the like. Non-limiting examples of biological agents that can be used include, but are not limited to, 5-Fluorouracil and/or derivatives thereof, 5-Phenylmethimazole and/or derivatives thereof; ACE inhibitors and/or derivatives thereof; acenocoumarol and/or derivatives thereof; acyclovir and/or derivatives thereof; actilyse and/or derivatives thereof; adrenocorticotropic hormone and/or derivatives thereof; adriamycin and/or derivatives thereof; agents that modulate intracellular $Ca_{2+}$ transport such as L-type (e.g., diltiazem, nifedipine, verapamil, etc.) or T-type $Ca_{2+}$ channel blockers (e.g., amiloride, etc.); alpha-adrenergic blocking agents and/or derivatives thereof; alteplase and/or derivatives thereof; amino glycosides and/or derivatives thereof (e.g. gentamycin, tobramycin, etc.); angiopeptin and/or derivatives thereof; angiostatic steroid and/or derivatives thereof; angiotensin II receptor antagonists and or derivatives thereof; anistreplase and/or derivatives thereof; antagonists of vascular epithelial growth factor and/or derivatives thereof; antibiotics; anti-coagulant compounds and/or derivatives thereof; anti-fibrosis compounds and/or derivatives thereof; anti-fungal compounds and/or derivatives thereof; anti-inflammatory compounds and/or derivatives thereof; Anti-Invasive Factor and/or derivatives thereof; anti-metabolite compounds and/or derivatives thereof (e.g., staurosporin, trichothecenes, and modified diphtheria and ricin toxins, Pseudomonas exotoxin, etc.); anti-matrix compounds and/or derivatives thereof (e.g., colchicine, tamoxifen, etc.); anti-microbial agents and/or derivatives thereof; anti-migratory agents and/or derivatives thereof (e.g., caffeic acid derivatives, nilvadipine, etc.); anti-mitotic compounds and/or derivatives thereof; anti-neoplastic compounds and/or derivatives thereof; anti-oxidants and/or derivatives thereof; anti-platelet compounds and/or derivatives thereof; anti-proliferative and/or derivatives thereof; anti-thrombogenic agents and/or derivatives thereof; argatroban and/or derivatives thereof; ap-1 inhibitors and/or derivatives thereof (e.g., for tyrosine kinase, protein kinase C, myosin light chain kinase, $Ca_{2+}$/calmodulin kinase II, casein kinase II, etc.); aspirin and/or derivatives thereof; azathioprine and/or derivatives thereof; β-Estradiol and/or derivatives thereof; β-1-anticollagenase and/or derivatives thereof, calcium channel blockers and/or derivatives thereof; calmodulin antagonists and/or derivatives thereof (e.g. $H_7$, etc.); CAPTOPRIL and/or derivatives thereof; cartilage-derived inhibitor and/or derivatives thereof; ChIMP-3 and/or derivatives thereof; cephalosporin and/or derivatives thereof (e.g., cefadroxil, cefazolin, cefaclor, etc.); chloroquine and/or derivatives thereof; chemotherapeutic compounds and/or derivatives thereof (e.g., 5-fluorouracil, vincristine, vinblastine, cisplatin, doxyrubicin, adriamycin, tamoifen, etc.); chymostatin and/or derivatives thereof; CILAZAPRIL and/or derivatives thereof; clopidigrel and/or derivatives thereof; clotrimazole and/or derivatives thereof; colchicine and/or derivatives thereof; cortisone and/or derivatives thereof; coumadin and/or derivatives thereof; curacin-A and or derivatives thereof; cyclosporine and/or derivatives thereof; cytochalasin and/or derivatives thereof (e.g., cytochalasin A, cytochalasin B, cytochalasin C, cytochalasin D, cytochalasin E, cytochalasin F, cytochalasin G, cytochalasin H, cytochalasin J, cytochalasin K, cytochalasin L, cytochalasin M, cytochalasin N, cytochalasin O, cytochalasin P, cytochalasin Q, cytochalasin R, cytochalasin S, chaetoglobosin A, chaetoglobosin B, chaetoglobosin C, chaetoglobosin D, chaetoglobosin E, chaetoglobosin F, chaetoglobosin G, chaetoglobosin J, chaetoglobosin K, deoxaphomin, proxiphomin, protophomin, zygosporin D, zygosporin E, zygosporin F, zygosporin G, aspochalasin B, aspochalasin C, aspochalasin D, etc.); cytokines and or derivatives thereof; desirudin and/or derivatives thereof; dexamethazone and/or derivatives thereof; dipyridamole and or derivatives thereof; eminase and/or derivatives thereof; endothelin and/or derivatives thereof; endothelial growth factor and/or derivatives thereof; epidermal growth factor and/or derivatives thereof; epothilone and/or derivatives thereof; estramustine and/or derivatives thereof; estrogen and/or derivatives thereof; fenoprofen and/or derivatives thereof; fluorouracil and/or derivatives thereof; flucytosine and/or derivatives thereof; forskolin and/or derivatives thereof; ganciclovir and/or derivatives thereof; glucocorticoids and/or derivatives thereof (e.g. dexamethasone, betamethasone, etc.); glycoprotein IIb/IIIa platelet membrane receptor antibody and/or derivatives thereof; GM-CSF and/or derivatives thereof; griseofulvin and/or derivatives thereof; growth factors and/or derivatives thereof (e.g., VEGF; TGF; IGF; PDGF; FGF, etc.); growth hormone and/or derivatives thereof; heparin and/or derivatives thereof; hirudin and or derivatives thereof; hyaluronate and/or derivatives thereof, hydrocortisone and/or derivatives thereof; ibuprofen and/or derivatives thereof; immunosuppressive agents and/or derivatives thereof (e.g., adrenocorticosteroids, cyclosporine, etc.); indomethacin and/or derivatives thereof; inhibitors of the sodium calcium antiporter and/or derivatives thereof (e.g., amiloride, etc.); inhibitors of the $IP_3$ receptor and/or derivatives thereof; inhibitors of the sodium/hydrogen antiporter and/or derivatives thereof (e.g., amiloride and derivatives thereof, etc.); insulin and/or derivatives thereof; Interferon alpha 2 Macroglobulin and/or derivatives thereof; ketoconazole and or derivatives thereof; Lepirudin and/or derivatives thereof; LISINOPRIL and/or derivatives thereof; LOVASTATIN and/or derivatives thereof; marevan and/or derivatives thereof; mefloquine and/or derivatives thereof; metalloproteinase inhibitors and/or derivatives thereof; methotrexate and/or derivatives thereof; metronidazole and/or derivatives thereof; miconazole and/or derivatives thereof; monoclonal antibodies and/or derivatives thereof; mutamycin and/or derivatives thereof; naproxen and/or derivatives thereof; nitric oxide and/or derivatives thereof; nitroprusside and or derivatives thereof; nucleic acid analogues and/or derivatives thereof (e.g., peptide nucleic acids, etc.); nystatin and/or derivatives thereof; oligonucleotides and or derivatives thereof; paclitaxel and/or derivatives thereof; penicillin and/or derivatives thereof, pentamidine isethionate and/or derivatives thereof; phenindione and or derivatives thereof; phenylbutazone and/or derivatives thereof; phosphodiesterase inhibitors and/or derivatives thereof; Plasminogen Activator Inhibitor-1 and/or derivatives thereof; Plasminogen Activator Inhibitor-2 and/or derivatives thereof; Platelet Factor 4 and/or derivatives thereof; platelet derived growth factor and/or derivatives thereof; plavix and/or derivatives thereof; POSTMI 75 and/or derivatives thereof; prednisone and/or derivatives thereof, prednisolone and/or derivatives thereof; probucol and/or derivatives thereof; progesterone and/or derivatives thereof; prostacyclin and/or derivatives thereof; prostaglandin inhibitors and/or derivatives thereof; protamine and/or derivatives thereof; protease and/or derivatives thereof; protein kinase inhibitors and/or derivatives thereof (e.g., staurosporin, etc.); quinine and/or derivatives thereof; radioactive agents and/or derivatives thereof (e.g., Cu-64, Ca-67, Cs-131, Ga-68, Zr-89, Ku-97, Tc-99m, Rh-105, Pd-103, Pd-109, In-111, I-123, I-125, I-131, Re-186, Re-188, Au-198, Au-199, Pb-203, At-211, Pb-212, Bi-212, $H_3P^{32}O_4$, etc.); rapamycin and/or derivatives thereof; receptor antagonists for histamine and/or derivatives thereof; refludan and/or derivatives thereof; retinoic acids and/or derivatives thereof; revasc and/or derivatives thereof, rifamycin and/or derivatives thereof; sense or anti-sense oligonucleotides and/or derivatives thereof (e.g., DNA, RNA, plasmid DNA, plasmid RNA, etc.); seramin and/or derivatives thereof; steroids; seramin and/or derivatives thereof; serotonin and/or derivatives thereof; serotonin blockers and/or derivatives thereof; streptokinase and/or derivatives thereof; sulfasalazine and/or derivatives thereof; sulfonamides and/or derivatives thereof (e.g., sulfamethoxazole, etc.); sulphated chitin derivatives; Sulphated Polysaccharide Peptidoglycan Complex and or derivatives thereof; $T_{H1}$ and/or derivatives thereof (e.g., Interleukins-2, -12, and -15, gamma interferon, etc.); thioprotese inhibitors and/or derivatives thereof; taxol and/or derivatives thereof (e.g., taxotere, baccatin, 10-deacetyltaxol, 7-xylosyl-10-deacetyltaxol, cephalomannine, 10-deacetyl-7-epitaxol, 7 epitaxol, 10-deacetylbaccatin III, 10-deacetylcephaolmannine, etc.); ticlid and/or derivatives thereof; ticlopidine and/or derivatives thereof; tick anti-coagulant peptide and/or derivatives thereof; thioprotese inhibitors and/or derivatives thereof; thyroid hormone and/or derivatives thereof; Tissue Inhibitor of Metalloproteinase-1 and or derivatives thereof, Tissue Inhibitor of Metalloproteinase-2 and or derivatives thereof; tissue plasma activators; TNF and/or derivatives thereof, tocopherol and/or derivatives thereof; toxins and/or derivatives thereof; tranilast and/or derivatives thereof, transforming growth factors alpha and beta and/or derivatives thereof; trapidil and/or derivatives thereof; triazolopyrimidine and/or derivatives thereof; vapiprost and/or derivatives thereof; vinblastine and/or derivatives thereof; vincristine and/or derivatives thereof; zidovudine and/or derivatives thereof. As can be appreciated, the biological agent can include one or more derivatives of the above listed compounds and/or other compounds. In one non-limiting embodiment, the biological agent includes, but is not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The type and/or amount of biological agent included on, in and/or in conjunction with the medical device is generally selected for the treatment of one or more medical treatments. Typically the amount of biological agent included on, in and/or used in conjunction with the medical device is about 0.01-100 ug per $mm^2$; however, other amounts can be used. The amount of two of more biological agents on, in and/or used in conjunction with the medical device can be the same or different. In one non-limiting example, the medical device can be coated with and/or includes one or more biological agents such as, but not limited to, trapidil and/or trapidil derivatives, taxol, taxol derivatives (e.g., taxotere, baccatin, 10-deacetyltaxol, 7-xylosyl-10-deacetyltaxol, cephalomannine, 10-deacetyl-7-epitaxol, 7 epitaxol, 10-deacetylbaccatin III, 10-deacetylcephaolmannine, etc.), cytochalasin, cytochalasin derivatives (e.g., cytochalasin A, cytochalasin B, cytochalasin C, cytochalasin D, cytochalasin E, cytochalasin F, cytochalasin G, cytochalasin H, cytochalasin J, cytochalasin K, cytochalasin L, cytochalasin M, cytochalasin N, cytochalasin O, cytochalasin P, cytochalasin Q, cytochalasin R, cytochalasin S, chaetoglobosin A, chaetoglobosin B, chaetoglobosin C, chaetoglobosin D, chaetoglobosin E, chaetoglobosin F, chaetoglobosin G, chaetoglobosin J, chaetoglobosin K, deoxaphomin, proxiphomin, protophomin, zygosporin D, zygosporin E, zygosporin F, zygosporin G, aspochalasin B, aspochalasin C, aspochalasin D, etc.), paclitaxel, paclitaxel derivatives, rapamycin, rapamycin derivatives, 5-Phenylmethimazole, 5-Phenylmethimazole derivatives, GM-CSF (granulo-cyte-macrophage colony-stimulating-factor), GM-CSF derivatives, or combinations thereof. In one non-limiting embodiment of the invention, the medical device can be partially of fully coated with one or more biological agents, impregnated with one or more biological agents to facilitate in the success of a particular medical procedure. The one or more biological agents can be coated on and/or impregnated in the medical device by a variety of mechanisms such as, but not limited to, spraying (e.g., atomizing spray techniques, etc.), dip coating, roll coating, sonication, brushing, plasma deposition, depositing by vapor deposition. In another and/or alternative non-limiting embodiment of the invention, the type and/or amount of biological agent included on, in and/or in conjunction with the medical device is generally selected for the treatment of one or more medical treatments. Typically, the amount of biological agent included on, in and/or used in conjunction with the medical device is about 0.01-100 ug per $mm^2$; however, other amounts can be used. The amount of two or more biological agents on, in and/or used in conjunction with the medical device can be the same or different. For instance, one or more biological agents can be coated on, and/or incorporated in one or more portions of the medical device to provide local and/or systemic delivery of one or more biological agents in and/or to a body passageway to a) inhibit or prevent thrombosis, in-stent restenosis, vascular narrowing and/or restenosis after the medical device has been inserted in and/or connected to a body passageway, b) at least partially passivate, remove and/or dissolve lipids, fibroblast, fibrin. etc. in a body passageway so as to at least partially remove such materials and/or to passivate such vulnerable materials (e.g., vulnerable plaque, etc.) in the body passageway in the region of the medical device and/or down stream of the medical device. As can be appreciated, the one or more biological agents can have many other or additional uses. In another and/or alternative non-limiting example, the medical device is coated with and/or includes one or more biological agents such as, but not limited to, trapidil and/or trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. In still another and/or alternative non-limiting example, the medical device is coated with and/or includes one or more biological agents such as, but not limited to trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof and one or more additional biological agents, such as, but not limited to, biological agents associated with thrombolytics, vasodilators, anti-hypertensive agents, anti-microbial or anti-biotic, anti-mitotic, anti-proliferative, anti-secretory agents, non-steroidal anti-inflammatory drugs, immunosuppressive agents, growth factors and growth factor antagonists, antitumor and/or chemotherapeutic agents, anti-polymerases, anti-viral agents, anti-body targeted therapy agents, hormones, anti-oxidants, biologic components, radio-therapeutic agents, radiopaque agents and/or radio-labeled agents. In addition to these biological agents, the medical device can be coated with and/or include one or more biological agents that are capable of inhibiting or preventing any adverse biological response by and/or to the medical device that could possibly lead to device failure and/or an adverse reaction by human or animal tissue. A wide range of biological agents thus can be used.

In a further and/or alternative non-limiting aspect of the present invention, the one or more biological agents on and/or in the medical device, when used on the medical device, can be released in a controlled manner so the area in question to be treated is provided with the desired dosage of biological agent over a sustained period of time. As can be appreciated, controlled release of one or more biological agents on the medical device is not always required and/or desirable. As such, one or more of the biological agents on and/or in the medical device can be uncontrollably released from the medical device during and/or after insertion of the medical device in the treatment area. It can also be appreciated that one or more biological agents on and/or in the medical device can be controllably released from the medical device and one or more biological agents on and/or in the medical device can be uncontrollably released from the medical device. It can also be appreciated that one or more biological agents on and/or in one region of the medical device can be controllably released from the medical device and one or more biological agents on and/or in the medical device can be uncontrollably released from another region on the medical device. As such, the medical device can be designed such that 1) all the biological agent on and/or in the medical device is controllably released, 2) some of the biological agent on and/or in the medical device is controllably released and some of the biological agent on the medical device is non-controllably released, or 3) none of the biological agent on and/or in the medical device is controllably released. The medical device can also be designed such that the rate of release of the one or more biological agents from the medical device is the same or different. The medical device can also be designed such that the rate of release of the one or more biological agents from one or more regions on the medical device is the same or different. Non-limiting arrangements that can be used to control the release of one or more biological agent from the medical device include a) at least partially coat one or more biological agents with one or more polymers, b) at least partially incorporate and/or at least partially encapsulate one or more biological agents into and/or with one or more polymers, and/or c) insert one or more biological agents in pores, passageway, cavities, etc. in the medical device and at least partially coat or cover such pores, passageway, cavities, etc. with one or more polymers. As can be appreciated, other or additional arrangements can be used to control the release of one or more biological agent from the medical device. The one or more polymers used to at least partially control the release of one or more biological agent from the medical device can be porous or non-porous. The one or more biological agents can be inserted into and/or applied to one or more surface structures and/or micro-structures on the medical device, and/or be used to at least partially form one or more surface structures and/or micro-structures on the medical device. As such, the one or more biological agents on the medical device can be 1) coated on one or more surface regions of the medical device, 2) inserted and/or impregnated in one or more surface structures and/or micro-structures, etc. of the medical device, and/or 3) form at least a portion or be included in at least a portion of the structure of the medical device. When the one or more biological agents are coated on the medical device, the one or more biological agents can 1) be directly coated on one or more surfaces of the medical device, 2) be mixed with one or more coating polymers or other coating materials and then at least partially coated on one or more surfaces of the medical device, 3) be at least partially coated on the surface of another coating material that has been at least partially coated on the medical device, and/or 4) be at least partially encapsulated between a) a surface or region of the medical device and one or more other coating materials and/or b) two or more other coating materials. As can be appreciated, many other coating arrangements can be additionally or alternatively used. When the one or more biological agents are inserted and/or impregnated in one or more internal structures, surface structures and/or micro-structures of the medical device, 1) one or more other coating materials can be applied at least partially over the one or more internal structures, surface structures and/or micro-structures of the medical device, and/or 2) one or more polymers can be combined with one or more biological agents. As such, the one or more biological agents can be 1) embedded in the structure of the medical device; 2) positioned in one or more internal structures of the medical device; 3) encapsulated between two polymer coatings; 4) encapsulated between the base structure and a polymer coating; 5) mixed in the base structure of the medical device that includes at least one polymer coating; or 6) one or more combinations of 1, 2, 3, 4 and/or 5. In addition or alternatively, the one or more coating of the one or more polymers on the medical device can include 1) one or more coatings of non-porous polymers; 2) one or more coatings of a combination of one or more porous polymers and one or more non-porous polymers; 3) one or more coating of porous polymer, or 4) one or more combinations of options 1, 2, and 3. As can be appreciated different biological agents can be located in and/or between different polymer coating layers and/or on and/or the structure of the medical device. As can also be appreciated, many other and/or additional coating combinations and/or configurations can be used. The concentration of one or more biological agents, the type of polymer, the type and/or shape of internal structures in the medical device and/or the coating thickness of one or more biological agents can be used to control the release time, the release rate and/or the dosage amount of one or more biological agents; however, other or additional combinations can be used. As such, the biological agent and polymer system combination and location on the medical device can be numerous. As can also be appreciated, one or more biological agents can be deposited on the top surface of the medical device to provide an initial uncontrolled burst effect of the one or more biological agents prior to 1) the control release of the one or more biological agents through one or more layers of polymer system that include one or more non-porous polymers and/or 2) the uncontrolled release of the one or more biological agents through one or more layers of polymer system. The one or more biological agents and/or polymers can be coated on the medical device by a variety of mechanisms such as, but not limited to, spraying (e.g., atomizing spray techniques, etc.), dip coating, roll coating, sonication, brushing, plasma deposition, and/or depositing by vapor deposition. The thickness of each polymer layer and/or layer of biological agent is generally at least about 0.01 µm and is generally less than about 150 µm. In one non-limiting embodiment, the thickness of a polymer layer and/or layer of biological agent is about 0.02-75 µm, more particularly about 0.05-50 µm, and even more particularly about 1-30 µm. When the medical device includes and/or is coated with one or more biological agents such that at least one of the biological agents is at least partially controllably released from the medical device, the need or use of body-wide therapy for extended periods of time can be reduced or eliminated. In the past, the use of body-wide therapy was used by the patient long after the patient left the hospital or other type of medical facility. This body-wide therapy could last days, weeks, months or sometimes over a year after surgery. The medical device of the present invention can be applied or inserted into a treatment area and 1) merely requires reduced use and/or extended use of body wide therapy after application or insertion of the medical device or 2) does not require use and/or extended use of body-wide therapy after application or insertion of the medical device. As can be appreciated, use and/or extended use of body wide therapy can be used after application or insertion of the medical device at the treatment area. In one non-limiting example, no body-wide therapy is needed after the insertion of the medical device into a patient. In another and/or alternative non-limiting example, short term use of body-wide therapy is needed or used after the insertion of the medical device into a patient. Such short term use can be terminated after the release of the patient from the hospital or other type of medical facility, or one to two days or weeks after the release of the patient from the hospital or other type of medical facility; however, it will be appreciated that other time periods of body-wide therapy can be used. As a result of the use of the medical device of the present invention, the use of body-wide therapy after a medical procedure involving the insertion of a medical device into a treatment area can be significantly reduced or eliminated.

In another and/or alternative non-limiting aspect of the present invention, controlled release of one or more biological agents from the medical device, when controlled release is desired, can be accomplished by using one or more non-porous polymer layers; however, other and/or additional mechanisms can be used to controllably release the one or more biological agents. The one or more biological agents are at least partially controllably released by molecular diffusion through the one or more non-porous polymer layers. When one or more non-porous polymer layers are used, the one or more polymer layers are typically biocompatible polymers; however, this is not required. The one or more non-porous polymers can be applied to the medical device without the use of chemical, solvents, and or catalysts; however, this is not required. In one non-limiting example the non-porous polymer can be at least partially applied by, but not limited to, vapor deposition and/or plasma deposition. The non-porous polymer can be selected so as to polymerize and cure merely upon condensation from the vapor phase; however, this is not required. The application of the one or more non-porous polymer layers can be accomplished without increasing the temperature above ambient temperature (e.g., 65-90° F.); however, this is not required. The non-porous polymer system can be mixed with one or more biological agents prior to being coated on the medical device and/or be coated on a medical device that previously included one or more biological agents; however, this is not required. The use or one or more non-porous polymer layers allow for accurate controlled release of the biological agent from the medical device. The controlled release of one or more biological agents through the non-porous polymer is at least partially controlled on a molecular level utilizing the motility of diffusion of the biological agent through the non-porous polymer. In one non-limiting example, the one or more non-porous polymer layers can include, but are not limited to, polyamide, parylene (e.g., parylene C, parylene N) and/or a parylene derivative.

In still another and/or alternative non-limiting aspect of the present invention, controlled release of one or more biological agents from the medical device, when controlled release is desired, can be accomplished by using one or more polymers that form a chemical bond with one or more biological agents. In one non-limiting example, at least one biological agent includes trapidil, trapidil derivative or a salt thereof that is covalently bonded to at least one polymer such as, but not limited to, an ethylene-acrylic acid copolymer. The ethylene is the hydrophobic group and acrylic acid is the hydrophilic group. The mole ratio of the ethylene to the acrylic acid in the copolymer can be used to control the hydrophobicity of the copolymer. The degree of hydrophobicity of one or more polymers can also be used to control the release rate of one or more biological agents from the one or more polymers. The amount of biological agent that can be loaded with one or more polymers may be a function of the concentration of anionic groups and/or cationic groups in the one or more polymer. For biological agents that are anionic, the concentration of biological agent that can be loaded on the one or more polymers is generally a function of the concentration of cationic groups (e.g. amine groups and the like) in the one or more polymer and the fraction of these cationic groups that can ionically bind to the anionic form of the one or more biological agents. For biological agents that are cationic (e.g., trapidil, etc.), the concentration of biological agent that can be loaded on the one or more polymers is generally a function of the concentration of anionic groups (i.e., carboxylate groups, phosphate groups, sulfate groups, and/or other organic anionic groups) in the one or more polymers, and the fraction of these anionic groups that can ionically bind to the cationic form of the one or more biological agents. As such, the concentration of one or more biological agent that can be bound to the one or more polymers can be varied by controlling the amount of hydrophobic and hydrophilic monomer in the one or more polymers, by controlling the efficiency of salt formation between the biological agent, and/or the anionic/cationic groups in the one or more polymers.

In still another and/or alternative non-limiting aspect of the present invention, controlled release of one or more biological agents from the medical device, when controlled release is desired, can be accomplished by using one or more polymers that include one or more induced cross-links. These one or more cross-links can be used to at least partially control the rate of release of the one or more biological agents from the one or more polymers. The cross-linking in the one or more polymers can be instituted by a number to techniques such as, but not limited to using catalysts, using radiation, using heat, and/or the like. The one or more cross-links formed in the one or more polymers can result in the one or more biological agents to become partially or fully entrapped within the cross-linking, and/or form a bond with the cross-linking. As such, the partially or fully biological agent takes longer to release itself from the cross-linking, thereby delaying the release rate of the one or more biological agents from the one or more polymers. Consequently, the amount of biological agent, and/or the rate at which the biological agent is released from the medical device over time can be at least partially controlled by the amount or degree of cross-linking in the one or more polymers.

In still a further and/or alternative aspect of the present invention, a variety of polymers can be coated on the medical device and/or be used to form at least a portion of the medical device. The one or more polymers can be used on the medical for a variety of reasons such as, but not limited to, 1) forming a portion of the medical device, 2) improving a physical property of the medical device (e.g., improve strength, improve durability, improve biocompatibility, reduce friction, etc.), 3) forming a protective coating on one or more surface structures on the medical device, 4) at least partially forming one or more surface structures on the medical device, and/or 5) at least partially controlling a release rate of one or more biological agents from the medical device. As can be appreciated, the one or more polymers can have other or additional uses on the medical device. The one or more polymers can be porous, non-porous, biostable, biodegradable (i.e. dissolves, degrades, is absorbed, or any combination thereof in the body), and or biocompatible. When the medical device is coated with one or more polymers, the polymer can include 1) one or more coatings of non-porous polymers; 2) one or more coatings of a combination of one or more porous polymers and one or more non-porous polymers; 3) one or more coatings of one or more porous polymers and one or more coatings of one or more non-porous polymers; 4) one or more coating of porous polymer, or 5) one or more combinations of options 1, 2, 3 and 4. The thickness of one or more of the polymer layers can be the same or different. When one or more layers of polymer are coated onto at least a portion of the medical device, the one or more coatings can be applied by a variety of techniques such as, but not limited to, vapor deposition and/or plasma deposition, spraying, dip-coating, roll coating, sonication, atomization, brushing and/or the like; however, other or additional coating techniques can be used. The one or more polymers that can be coated on the medical device and/or used to at least partially form the medical device can be polymers that considered to be biodegradable, bioresorbable, or bioerodable; polymers that are considered to be biostable; and/or polymers that can be made to be biodegradable and/or bioresorbable with modification. Non-limiting examples of polymers that are considered to be biodegradable, bioresorbable, or bioerodable include, but are not limited to, aliphatic polyesters; poly(glycolic acid) and/or copolymers thereof (e.g., poly(glycolide trimethylene carbonate); poly(caprolactone glycolide)); poly(lactic acid) and/or isomers thereof (e.g., poly-L(lactic acid) and/or poly-D Lactic acid) and/or copolymers thereof (e.g. DL-PLA), with and without additives (e.g. calcium phosphate glass), and/or other copolymers (e.g. poly(caprolactone lactide), poly(lactide glycolide), poly(lactic acid ethylene glycol)); poly(ethylene glycol); poly(ethylene glycol) diacrylate; poly(lactide); polyalkylene succinate; polybutylene diglycolate; polyhydroxybutyrate (PHB); polyhydroxyvalerate (PHV); polyhydroxybutyrate/polyhydroxyvalerate copolymer (PHB/PHV); poly(hydroxybutyrate-co-valerate); polyhydroxyalkaoates (PHA); polycaprolactone; poly(caprolactone-polyethylene glycol) copolymer; poly(valerolactone); polyanhydrides; poly(orthoesters) and/or blends with polyanhydrides; poly(anhydride-co-imide); polycarbonates (aliphatic); poly(hydroxyl-esters); polydioxanone; polyanhydrides; polyanhydride esters; polycyanoacrylates; poly(alkyl 2-cyanoacrylates); poly(amino acids); poly(phosphazenes); poly(propylene fumarate); poly(propylene fumarate-co-ethylene glycol); poly(fumarate anhydrides); fibrinogen; fibrin; gelatin; cellulose and/or cellulose derivatives and/or cellulosic polymers (e.g., cellulose acetate, cellulose acetate butyrate, cellulose butyrate, cellulose ethers, cellulose nitrate, cellulose propionate, cellophane); chitosan and/or chitosan derivatives (e.g., chitosan NOCC, chitosan NOOC-G); alginate; polysaccharides; starch; amylase; collagen; polycarboxylic acids; poly(ethyl ester-co-carboxylate carbonate) (and/or other tyrosine derived polycarbonates); poly(iminocarbonate); poly(BPA-iminocarbonate); poly(trimethylene carbonate); poly(iminocarbonate-amide) copolymers and/or other pseudo-poly(amino acids); poly(ethylene glycol); poly(ethylene oxide); poly(ethylene oxide)/poly(butylene terephthalate) copolymer; poly(epsilon-caprolactone-dimethyltrimethylene carbonate); poly(ester amide); poly(amino acids) and conventional synthetic polymers thereof; poly(alkylene oxalates); poly(alkylcarbonate); poly(adipic anhydride); nylon copolyamides; NO-carboxymethyl chitosan NOCC); carboxymethyl cellulose; copoly(ether-esters) (e.g., PEO/PLA dextrans); polyketals; biodegradable polyethers; biodegradable polyesters; polydihydropyrans; polydepsipeptides; polyarylates (L-tyrosine-derived) and/or free acid polyarylates; polyamides (e.g. Nylon 66, polycaprolactam); poly(propylene fumarate-co-ethylene glycol) (e.g., fumarate anhydrides); hyaluronates; poly-p-dioxanone; polypeptides and proteins; polyphosphoester; polyphosphoester urethane; polysaccharides; pseudo-poly(amino acids); starch; terpolymer; (copolymers of glycolide, lactide, or dimethyltrimethylene carbonate); rayon; rayon triacetate; latex; and/pr copolymers, blends, and/or composites of above. Non-limiting examples of polymers that considered to be biostable include, but are not limited to, parylene; parylene c; parylene f, parylene n; parylene derivatives; maleic anyhydride polymers; phosphorylcholine; poly n-butyl methacrylate (PBMA); polyethylene-co-vinyl acetate (PEVA); PBMA/PEVA blend or copolymer; polytetrafluoroethene (Teflon®) and derivatives; poly-paraphenylene terephthalamide (Kevlar®); poly(ether ether ketone) (PEEK); poly(styrene-b-isobutylene-b-styrene) (Translute™); tetramethyldisiloxane (side chain or copolymer); polyimides polysulfides; poly(ethylene terephthalate); poly(methyl methacrylate); poly(ethylene-co-methyl methacrylate); styrene-ethylene/butylene-styrene block copolymers; ABS; SAN acrylic polymers and/or copolymers (e.g., n-butyl-acrylate, n-butyl methacrylate, 2-ethylhexyl acrylate, lauryl-acrylate, 2-hydroxy-propyl acrylate, polyhydroxyethyl, methacrylate methylmethacrylate copolymers); glycosaminoglycans; alkyd resins; elastin; polyether sulfones; epoxy resin; poly(oxymethylene); polyolefins; polymers of silicone; polymers of methane; polyisobutylene; ethylene-alphaolefin copolymers; polyethylene; polyacrylonitrile; fluorosilicones; poly(propylene oxide); polyvinyl aromatics (e.g. polystyrene); poly(vinyl ethers) (e.g. polyvinyl methyl ether); poly(vinyl ketones); poly(vinylidene halides) (e.g. polyvinylidene fluoride, polyvinylidene chloride); poly(vinylpyrolidone); poly(vinylpyrolidone)/vinyl acetate copolymer; polyvinylpridine prolastin or silk-elastin polymers (SELP); silicone; silicone rubber; polyurethanes (polycarbonate polyurethanes, silicone urethane polymer) (e.g., chronoflex varieties, bionate varieties); vinyl halide polymers and/or copolymers (e.g. polyvinyl chloride); polyacrylic acid; ethylene acrylic acid copolymer; ethylene vinyl acetate copolymer; polyvinyl alcohol; poly(hydroxyl alkylmethacrylate); Polyvinyl esters (e.g. polyvinyl acetate); and/or copolymers, blends, and/or composites of above. Non-limiting examples of polymers that can be made to be biodegradable and/or bioresorbable with modification include, but are not limited to, hyaluronic acid (hyanluron); polycarbonates; polyorthocarbonates; copolymers of vinyl monomers; polyacetals; biodegradable polyurethanes; polyacrylamide; polyisocyanates; polyamide; and/or copolymers, blends, and/or composites of above. As can be appreciated, other and/or additional polymers and/or derivatives of one or more of the above listed polymers can be used. The one or more polymers can be coated on the medical device by a variety of mechanisms such as, but not limited to, spraying (e.g., atomizing spray techniques, etc.), dip coating, roll coating, sonication, brushing, plasma deposition, and/or depositing by vapor deposition. The thickness of each polymer layer is generally at least about 0.01 μm and is generally less than about 150 μm; however, other thicknesses can be used, in one non-limiting embodiment, the thickness of a polymer layer and/or layer of biological agent is about 0.02-75 μm, more particularly about 0.05-50 μm, and even more particularly about 1-30 μm. As can be appreciated, other thicknesses can be used. In one non-limiting embodiment, the medical device includes and/or is coated with parylene, PLGA, POE, PGA, PLLA, PAA, PEG, chitosan and/or derivatives of one or more of these polymers. In another and/or alternative non-limiting embodiment, the medical device includes and/or is coated with a non-porous polymer that includes, but is not limited to, polyamide, parylene c, parylene n and/or a parylene derivative. In still another and/or alternative non-limiting embodiment, the medical device includes and/or is coated with poly(ethylene oxide), poly(ethylene glycol), and poly(propylene oxide), polymers of silicone, methane, tetrafluoroethylene (including TEFLON brand polymers), tetramethyldisiloxane, and the like.

In another and/or alternative non-limiting aspect of the present invention, the medical device, when including and/or is coated with one or more biological agents, can include and/or can be coated with one or more biological agents that are the same or different in different regions of the medical device and/or have differing amounts and/or concentrations in differing regions of the medical device. For instance, the medical device can a) be coated with and/or include one or more biologicals on at least one portion of the medical device and at least another portion of the medical device is not coated with and/or includes biological agent; b) be coated with and/or include one or more biologicals on at least one portion of the medical device that is different from one or more biologicals on at least another portion of the medical device; c) be coated with and/or include one or more biologicals at a concentration on at least one portion of the medical device that is different from the concentration of one or more biologicals on at least another portion of the medical device; etc.

In still another and/or alternative non-limiting aspect of the present invention, one or more surfaces of the medical device can be treated to achieve the desired coating properties of the one or more biological agents and one or more polymers coated on the medical device. Such surface treatment techniques include, but are not limited to, cleaning, buffing, smoothing, etching (chemical etching, plasma etching, etc.), etc. When an etching process is used, various gasses can be used for such a surface treatment process such as, but not limited to, carbon dioxide, nitrogen, oxygen, Freon, helium, hydrogen, etc. The plasma etching process can be used to clean the surface of the medical device, change the surface properties of the medical device so as to affect the adhesion properties, lubricity properties, etc. of the surface of the medical device. As can be appreciated, other or additional surface treatment processes can be used prior to the coating of one or more biological agents and/or polymers on the surface of the medical device. In one non-limiting manufacturing process, one or more portions of the medical device are cleaned and/or plasma etched; however, this is not required. Plasma etching can be used to clean the surface of the medical device, and or to form one or more non-smooth surfaces on the medical device to facilitate in the adhesion of one or more coatings of biological agents and or one or more coatings of polymer on the medical device. The gas for the plasma etching can include carbon dioxide and or other gasses. Once one or more surface regions of the medical device have been treated, one or more coatings of polymer and/or biological agent can be applied to one or more regions of the medical device. For instance, 1) one or more layers of porous or non-porous polymer can be coated on an outer and or inner surface of the medical device, 2) one or more layers of biological agent can be coated on an outer and/or inner surface of the medical device, or 3) one or more layers of porous or non-porous polymer that includes one or more biological agents can be coated on an outer and/or inner surface of the medical device. The one or more layers of biological agent can be applied to the medical device by a variety of techniques (e.g., dipping, rolling, brushing, spraying, particle atomization, etc.). One non-limiting coating technique is by an ultrasonic mist coating process wherein ultrasonic waves are used to break up the droplet of biological agent and form a mist of very fine droplets. These fine droplets have an average droplet diameter of about 0.1-3 microns. The fine droplet mist facilitates in the formation of a uniform coating thickness and can increase the coverage area on the medical device.

In still yet another and/or alternative non-limiting aspect of the present invention, one or more portions of the medical device can 1) include the same or different biological agents, 2) include the same or different amount of one or more biological agents, 3) include the same or different polymer coatings, 4) include the same or different coating thicknesses of one or more polymer coatings, 5) have one or more portions of the medical device controllably release and/or uncontrollably release one or more biological agents, and/or 6) have one or more portions of the medical device controllably release one or more biological agents and one or more portions of the medical device uncontrollably release one or more biological agents.

In yet another and/or alternative non-limiting aspect of the invention, the medical device can include a marker material that facilitates enabling the medical device to be properly positioned in a body passageway. The marker material is typically designed to be visible to electromagnetic waves (e.g., x-rays, microwaves, visible light, inferred waves, ultraviolet waves, etc.); sound waves (e.g., ultrasound waves, etc.); magnetic waves (e.g., MRI, etc.); and/or other types of electromagnetic waves (e.g., microwaves, visible light, inferred waves, ultraviolet waves, etc.). In one non-limiting embodiment, the marker material is visible to x-rays (i.e., radiopaque). The marker material can form all or a portion of the medical device and/or be coated on one or more portions (flaring portion and/or body portion; at ends of medical device; at or near transition of body portion and flaring section; etc.) of the medical device. The location of the marker material can be on one or multiple locations on the medical device. The size of the one or more regions that include the marker material can be the same or different. The marker material can be spaced at defined distances from one another so as to form ruler like markings on the medical device to facilitate in the positioning of the medical device in a body passageway. The marker material can be a rigid or flexible material. The marker material can be a biostable or biodegradable material. When the marker material is a rigid material, the marker material is typically formed of a metal material (e.g., metal band, metal plating, etc.); however, other or additional materials can be used. The metal which at least partially forms the medical device can function as a marker material; however, this is not required. When the marker material is a flexible material, the marker material typically is formed of one or more polymers that are marker materials in-of-themselves and or include one or more metal powders and/or metal compounds. In one non-limiting embodiment, the flexible marker material includes one or more metal powders in combinations with parylene, PLGA, POE, PGA, PLLA, PAA, PEG, chitosan and/or derivatives of one or more of these polymers. In another and/or alternative non-limiting embodiment, the flexible marker material includes one or more metals and/or metal powders of aluminum, barium, bismuth, cobalt, copper, chromium, gold, iron, stainless steel, titanium, vanadium, nickel, zirconium, niobium, lead, molybdenum, platinum, yttrium, calcium, rare earth metals, rhenium, zinc, silver, depleted radioactive elements, tantalum and/or tungsten; and/or compounds thereof. The marker material can be coated with a polymer protective material; however, this is not required. When the marker material is coated with a polymer protective material, the polymer coating can be used to 1) at least partially insulate the marker material from body fluids, 2) facilitate in retaining the marker material on the medical device, 3) at least partially shielding the marker material from damage during a medical procedure and/or 4) provide a desired surface profile on the medical device. As can be appreciated, the polymer coating can have other or additional uses. The polymer protective coating can be a biostable polymer or a biodegradable polymer (e.g., degrades and or is absorbed). The coating thickness of the protective coating polymer material, when used, is typically less than about 300 microns; however, other thickness can be used. In one non-limiting embodiment, the protective coating materials include parylene, PLGA, POE, PGA, PLLA, PAA, PEG, chitosan and or derivatives of one or more of these polymers.

In a further and/or alternative non-limiting aspect of the present invention, the medical device or one or more regions of the medical device can be constructed by use of one or more microelectromechanical manufacturing techniques (MEMS (e.g., micro-machining, laser micro-machining, laser micro-machining, micro-molding, etc.); however, other or additional manufacturing techniques can be used. The medical device can include one or more surface structures (e.g., pore, channel, pit, rib, slot, notch, bump, teeth, needle, well, hole, groove, etc.). These structures can be at least partially formed by MEMS (e.g., micro-machining, etc.) technology and/or other types of technology. The medical device can include one or more micro-structures (e.g., micro-needle, micro-pore, micro-cylinder, micro-cone, micro-pyramid, micro-tube, micro-parallelopiped, micro-prism, micro-hemisphere, teeth, rib, ridge, ratchet, hinge, zipper, zip-tie like structure, etc.) on the surface of the medical device. As defined herein, a micro-structure is a structure that has at least one dimension (e.g., average width, average diameter, average height, average length, average depth, etc.) that is no more than about 2 mm, and typically no more than about 1 mm. As can be appreciated, the medical device, when including one or more surface structures, a) all the surface structures can be micro-structures, b) all the surface structures can be non-micro-structures, or c) a portion of the surface structures can be micro-structures and a portion can be non-micro-structures. Non-limiting examples of structures that can be formed on the medical devices such as stents are illustrated in United States Patent Publication Nos. 2004/0093076 and 2004/0093077, which are incorporated herein by reference. Typically, the micro-structures, when formed, extend from or into the outer surface no more than about 400 microns, and more typically less than about 300 microns, and more typically about 15-250 microns; however, other sizes can be used. The micro-structures can be clustered together or disbursed throughout the surface of the medical device. Similar shaped and/or sized micro-structures and/or surface structures can be used, or different shaped and/or sized micro-structures can be used. When one or more surface structures and/or micro-structures are designed to extend from the surface of the medical device, the one or more surface structures and/or micro-structures can be formed in the extended position and or be designed so as to extend from the medical device during and/or after deployment of the medical device in a treatment area. The micro-structures and/or surface structures can be designed to contain and/or be fluidly connected to a passageway, cavity, etc.; however, this is not required. The one or more surface structures and/or micro-structures can be used to engage and/or penetrate surrounding tissue or organs once the medical device has be position on and or in a patient; however, this is not required. The one or more surface structures and/or micro-structures can be used to facilitate in forming maintaining a shape of a medical device (i.e., see devices in United States Patent Publication Nos. 2004/0093076 and 2004/0093077). The one or more surface structures and/or micro-structures can be at least partially formed by MEMS (e.g., micro-machining, laser micro-machining, micro-molding, etc.) technology; however, this is not required. In one non-limiting embodiment, the one or more surface structures and/or micro-structures can be at least partially formed of a biological agent and/or be formed of a polymer. One or more of the surface structures and/or micro-structures can include one or more internal passageways that can include one or more materials (e.g., biological agent, polymer, etc.); however, this is not required. The one or more surface structures and/or micro-structures can be formed by a variety of processes (e.g., machining, chemical modifications, chemical reactions, MEMS (e.g., micro-machining, etc.), etching, laser cutting, etc.). The one or more coatings and/or one or more surface structures and/or micro-structures of the medical device can be used for a variety of purposes such as, but not limited to, 1) increasing the bonding and/or adhesion of one or more biological agents, adhesives, marker materials and/or polymers to the medical device, 2) changing the appearance or surface characteristics of the medical device, and/or 3) controlling the release rate of one or more biological agents. The one or more micro-structures and/or surface structures can be biostable, biodegradable, etc. One or more regions of the medical device that are at least partially formed by microelectromechanical manufacturing techniques can be biostable, biodegradable, etc. The medical device or one or more regions of the medical device can be at least partially covered and/or filled with a protective material so to at least partially protect one or more regions of the medical device, and or one or more micro-structures and/or surface structures on the medical device from damage. One or more regions of the medical device, and/or one or more micro-structures and or surface structures on the medical device can be damaged when the medical device is 1) packaged and/or stored, 2) unpackaged, 3) connected to and or other secured and/or placed on another medical device, 4) inserted into a treatment area, 5) handled by a user, and or 6) form a barrier between one or more micro-structures and/or surface structures and fluids in the body passageway. As can be appreciated, the medical device can be damaged in other or additional ways. The protective material can be used to protect the medical device and one or more micro-structures and/or surface structures from such damage. The protective material can include one or more polymers previously identified above. The protective material can be 1) biostable and/or biodegradable and/or 2) porous and/or non-porous. In one non-limiting design, the polymer is at least partially biodegradable so as to at least partially exposed one or more micro-structure and/or surface structure to the environment after the medical device has been at least partially inserted into a treatment area. In another and/or additional non-limiting design, the protective material includes, but is not limited to, sugar (e.g., glucose, fructose, sucrose, etc.), carbohydrate compound, salt (e.g., NaCl, etc.), parylene, PLGA, POE, PGA, PLLA, PAA, PEG, chitosan and/or derivatives of one or more of these materials; however, other and/or additional materials can be used. In still another and/or additional non-limiting design, the thickness of the protective material is generally less than about 300 microns, and typically less than about 150 microns; however, other thicknesses can be used. The protective material can be coated by one or more mechanisms previously described herein.

In still yet another and/or alternative non-limiting aspect of the present invention, the medical device can include and/or be used with a physical hindrance. The physical hindrance can include, but is not limited to, an adhesive, a sheath, a magnet, tape, wire, string, etc. The physical hindrance can be used to 1) physically retain one or more regions of the medical device in a particular form or profile, 2) physically retain the medical device on a particular deployment device, 3) protect one or more surface structures and/or micro-structures on the medical device, and or 4) form a barrier between one or more surface regions, surface structures and/or micro-structures on the medical device and the fluids in a body passageway. As can be appreciated, the physical hindrance can have other and/or additional functions. The physical hindrance is typically a biodegradable material; however, a biostable material can be used. The physical hindrance can be designed to withstand sterilization of the medical device; however, this is not required. The physical hindrance can be applied to, included in and or be used in conjunction with one or more medical devices. Additionally or alternatively, the physical hindrance can be designed to be used with and or conjunction with a medical device for a limited period of time and then 1) disengage from the medical device after the medical device has been partially or fully deployed and/or 2) dissolve and/or degrade during and/or after the medical device has been partially or fully deployed; however, this is not required. Additionally or alternatively, the physical hindrance can be designed and be formulated to be temporarily used with a medical device to facilitate in the deployment of the medical device; however, this is not required. In one non-limiting use of the physical hindrance, the physical hindrance is designed or formulated to at least partially secure a medical device to another medical device that is used to at least partially transport the medical device to a location for treatment. In another and/or alternative non-limiting use of the physical hindrance, the physical hindrance is designed or formulated to at least partially maintain the medical device in a particular shape or form until the medical device is at least partially positioned in a treatment location. In still another and/or alternative non-limiting use of the physical hindrance, the physical hindrance is designed or formulated to at least partially maintain and/or secure one type of medical device to another type of medical instrument or device until the medical device is at least partially positioned in a treatment location. The physical hindrance can also or alternatively be designed and formulated to be used with a medical device to facilitate in the use of the medical device. In one non-limiting use of the physical hindrance, when in the form of an adhesive, can be formulated to at least partially secure a medical device to a treatment area so as to facilitate in maintaining the medical device at the treatment area. For instance, the physical hindrance can be used in such use to facilitate in maintaining a medical device on or at a treatment area until the medical device is properly secured to the treatment area by sutures, stitches, screws, nails, rod, etc; however, this is not required. Additionally or alternatively, the physical hindrance can be used to facilitate in maintaining a medical device on or at a treatment area until the medical device has partially or fully accomplished its objective. The physical hindrance is typically a biocompatible material so as to not cause unanticipated adverse effects when properly used. The physical hindrance can be biostable or biodegradable (e.g., degrades and/or is absorbed, etc.). When the physical hindrance includes or has one or more adhesives, the one or more adhesives can be applied to the medical device by, but is not limited to, spraying (e.g. atomizing spray techniques, etc.), dip coating, roll coating, sonication, brushing, plasma deposition, and/or depositing by vapor deposition, brushing, painting, etc.) on the medical device. The physical hindrance can also or alternatively form at least a part of the medical device. One or more regions and or surfaces of a medical device can also or alternatively include the physical hindrance. The physical hindrance can include one or more biological agents and/or other materials (e.g. marker material, polymer, etc.); however, this is not required. When the physical hindrance is or includes an adhesive, the adhesive can be formulated to controllably release one or more biological agents in the adhesive and/or coated on and/or contained within the medical device; however, this is not required. The adhesive can also or alternatively control the release of one or more biological agents located on and/or contained in the medical device by forming a penetrable or non-penetrable barrier to such biological agents; however, this is not required. The adhesive can include and/or be mixed with one or more polymers; however, this is not required. The one or more polymers can be used to 1) control the time of adhesion provided by said adhesive, 2) control the rate of degradation of the adhesive, and/or 3) control the rate of release of one or more biological agents from the adhesive and/or diffusing or penetrating through the adhesive layer; however, this is not required. When the physical hindrance includes a sheath, the sheath can be designed to partially or fully encircle the medical device. The sheath can be designed to be physically removed from the medical device after the medical device is deployed to a treatment area; however, this is not required. The sheath can be formed of a biodegradable material that at least partially degrades over time to at least partially expose one or more surface regions, micro-structures and/or surface structures of the medical device; however, this is not required. The sheath can include and or be at least partially coated with one or more biological agents. The sheath includes one or more polymers; however, this is not required. The one or more polymers can be used for a variety of reasons such as, but not limited to, 1) forming a portion of the sheath, 2) improving a physical property of the sheath (e.g., improve strength, improve durability, improve biocompatibility, reduce friction, etc.), and/or 3 at least partially controlling a release rate of one or more biological agents from the sheath. As can be appreciated, the one or more polymers can have other or additional uses on the sheath.

In another and/or alternative non-limiting aspect of the invention, the medical device can include a biostable construction. In such a design, the medical device has two or more stable configurations, including a first stable configuration with a first cross-sectional shape and a second stable configuration with a second cross-sectional shape. All or a portion of the medical device can include the biostable construction. The bistable construction can result in a generally uniform change in shape of the medical device, or one portion of the medical device can change into one or more configurations and one or more other portions of the medical device can change into one or more other configurations.

In still another and/or alternative aspect of the invention, the stent can be an expandable device that can be expanded by use of some other device (e.g., balloon, etc.) and/or is self expanding. The expandable stent can be fabricated from a material that has no or substantially no shape memory characteristics or can be partially fabricated from a material having shape-memory characteristics. Typically, when one or more shape-memory materials are used, the shape memory material composition is selected such that the shape memory material remains in an unexpanded configuration at a cold temperature (e.g., below body temperature); however, this is not required. When the shape memory material is heated (e.g., to body temperature) the expandable body section can be designed to expand to at least partially seal and secure the stent in a body passageway or other region; however, this is not required.

In still another and/or alternative non-limiting aspect of the invention, the medical device can be used in conjunction with one or more other biological agents that are not on the medical device. For instance, the success of the medical device can be improved by infusing, injecting or consuming orally one or more biological agents. Such biological agents can be the same and/or different from the one or more biological agents on and/or in the medical device. Such use of one or more biological agents are commonly used in systemic treatment of a patient after a medical procedure such as body wide after the medical device has been inserted in the treatment area can be reduced or eliminated by use of the novel alloy. Although the medical device of the present invention can be designed to reduce or eliminate the need for long periods of body wide therapy after the medical device has been inserted in the treatment area, the use of one or more biological agents can be used in conjunction with the medical device to enhance the success of the medical device and or reduce or prevent the occurrence of one or more biological problems (e.g., in-stent restenosis, vascular narrowing, thrombosis, infection, rejection of the medical device, etc.). For instance, solid dosage forms of biological agents for oral administration, and/or for other types of administration (e.g., suppositories, etc.) can be used. Such solid forms can include, but are not limited to capsules, tablets, effervescent tablets, chewable tablets, pills, powders, sachets, granules and gels. The solid form of the capsules, tablets, effervescent tablets, chewable tablets, pills, etc. can have a variety of shapes such as, but not limited to, spherical, cubical, cylindrical, pyramidal, and the like. In such solid dosage form, one or more biological agents can be admixed with at least one filler material such as, but not limited to, sucrose, lactose or starch; however, this is not required. Such dosage forms can include additional substances such as, but not limited to, inert diluents (e.g., lubricating agents, etc.). When capsules, tablets, effervescent tablets or pills are used, the dosage form can also include buffering agents; however, this is not required. Soft gelatin capsules can be prepared to contain a mixture of the one or more biological agents in combination with vegetable oil or other types of oil; however, this is not required. Hard gelatin capsules can contain granules of the one or more biological agents in combination with a solid carrier such as, but not limited to, lactose, potato starch, corn starch, cellulose derivatives of gelatin, etc; however, this is not required. Tablets and pills can be prepared with enteric coatings for additional time release characteristics; however, this is not required. Liquid dosage forms of the one or more biological agents for oral administration can include pharmaceutically acceptable emulsions, solutions, suspensions, syrups, elixirs, etc.; however, this is not required. In one non-limiting embodiment, when at least a portion of one or more biological agents is inserted into a treatment area (e.g., gel form, paste form, etc.) and or provided orally (e.g., pill, capsule, etc.) and/or anally (suppository, etc.), one or more of the biological agents can be controllably released; however, this is not required. In one non-limiting example, one or more biological agents can be given to a patient in solid dosage form and one or more of such biological agents can be controllably released from such solid dosage forms. In another and/or alternative non-limiting example trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof are given to a patient prior to, during and/or after the insertion of the medical device in a treatment area. As can be appreciated, other or additional biological agents can be used. Certain types of biological agents may be desirable to be present in a treated area for an extended period of time in order to utilize the full or nearly full clinical potential the biological agent. For instance, trapidil and/or trapidil derivatives is a compound that has many clinical attributes including, but not limited to, anti-platelet effects, inhibition of smooth muscle cells and monocytes, fibroblast proliferation and increased MAPK-1 which in turn deactivates kinase, a vasodilator, etc. These attributes can be effective in improving the success of a medical device that has been inserted at a treatment area. In some situations, these positive effects of trapidil and/or trapidil derivatives need to be prolonged in a treatment area in order to achieve complete clinical competency. Trapidil and/or trapidil derivatives have a half life in vivo of about 2-4 hours with hepatic clearance of 48 hours. In order to utilize the full clinical potential of trapidil and/or trapidil derivatives, trapidil and/or trapidil derivatives should be metabolized over an extended period of time without interruption; however, this is not required. By inserting trapidil and/or trapidil derivatives in a solid dosage form, the trapidil and/or trapidil derivatives could be released in a patient over extended periods of time in a controlled manner to achieve complete or nearly complete clinical competency of the trapidil and/or trapidil derivatives. In another and/or alternative non-limiting example, one or more biological agents are at least partially encapsulated in one or more polymers. The one or more polymers can be biodegradable, non-biodegradable, porous, and/or non-porous. When the one or more polymers are biodegradable, the rate of degradation of the one or more biodegradable polymers can be used to at least partially control the rate at which one or more biological agent that are released into a body passageway and/or other parts of the body over time. The one or more biological agents can be at least partially encapsulated with different polymer coating thickness, different numbers of coating layers, and/or with different polymers to alter the rate at which one or more biological agents are released in a body passageway and/or other parts of the body over time. The rate of degradation of the polymer is principally a function of 1) the water permeability and solubility of the polymer, 2) chemical composition of the polymer and/or biological agent, 3) mechanism of hydrolysis of the polymer, 4) the biological agent encapsulated in the polymer, 5) the size, shape and surface volume of the polymer, 6) porosity of the polymer, 7) the molecular weight of the polymer, 8) the degree of cross-linking in the polymer, 9) the degree of chemical bonding between the polymer and biological agent, and/or 10) the structure of the polymer and/or biological agent. As can be appreciated, other factors may also affect the rate of degradation of the polymer. When the one or more polymers are biostable, the rate at when the one or more biological agents are released from the biostable polymer is a function of 1) the porosity of the polymer, 2) the molecular diffusion rate of the biological agent through the polymer, 3) the degree of cross-linking in the polymer, 4) the degree of chemical bonding between the polymer and biological agent, 5) chemical composition of the polymer and/or biological agent, 6) the biological agent encapsulated in the polymer, 7) the size, shape and surface volume of the polymer, and/or 8) the structure of the polymer and/or biological agent. As can be appreciated, other factors may also affect the rate of release of the one or more biological agents from the biostable polymer. Many different polymers can be used such as, but not limited to, aliphatic polyester compounds (e.g., PLA (i.e. poly(D, L-lactic acid), poly(L-lactic acid)), PLGA (i.e. poly(lactide-co-glycoside), etc.), POE, PEG, PLLA, parylene, chitosan and/or derivatives thereof. As can be appreciated, the at least partially encapsulated biological agent can be introduced into a patient by means other than by oral introduction, such as, but not limited to, injection, topical applications, intravenously, eye drops, nasal spray, surgical insertion, suppositories, intrarticularly, intraocularly, intranasally, intradermally, sublingually, intravesically, intrathecally, intraperitoneally, intracranially, intramuscularly, subcutaneously, directly at a particular site, and the like.

In yet another and/or alternative non-limiting aspect of the invention, the medical device is in the form of a stent. The stent can be an expandable stent that is expandable by a balloon and/or is self-expanding. The stent can have one or more body members. The one or more body members can include first and second ends and a wall surface disposed between the first and second ends. Typically each body member has a first cross-sectional area which permits delivery of the body member into a body passageway, and a second, expanded cross-sectional area. The expansion of one or more body members of the stent can be accomplished in a variety of manners. In one manner, one or more body members are expanded to the second cross-sectional area by a radially, outwardly extending force applied at least partially from the interior region of the body member (e.g. by use of a balloon, etc.). The body member can include shape memory materials; however, this is not required. The second cross-sectional area of the stent can be fixed or variable. The stent can be designed such that one or more body members expand while substantially retaining the original longitudinal length of the body member; however, this is not required. The one or more body members can have a first cross-sectional shape that is generally circular so as to form a substantially tubular body member; however, the one or more body members can have other cross-sectional shapes. When the stent includes two or more body members, the two or more body members can be connected together by at least one connector member. The stent can include rounded, smooth and/or blunt surfaces to minimize and or prevent potential damage to a body passageway as the stent is inserted into a body passageway and/or expanded in a body passageway; however, this is not required. The stent can be treated with gamma, beta and/or e-beam radiation, and/or otherwise sterilized; however, this is not required. The stent is partially or fully formed from the novel metal alloy. The use of the novel metal alloy to form all or a portion of the stent can result in several advantages over stents formed from other materials. These advantages include, but are not limited to:

- The novel metal alloy has increased strength as compared with stainless steel or chromium-cobalt alloys, thus less quantity of novel metal alloy can be used in the stent to achieve similar strengths as compared to stents formed of different metals. As such, the resulting stent can be made smaller and less bulky by use of the novel metal alloy without sacrificing the strength and durability of the stent. The stent can also have a smaller profile, thus can be inserted into smaller areas, openings and/or passageways. The increased strength of the novel metal alloy also results in the increased radial strength of the stent. For instance, the thickness of the walls of the stent and/or the wires used to form the stent can be made thinner and achieve a similar or improved radial strength as compared with thicker walled stents formed of stainless steel or cobalt and chromium alloy.
- The novel metal alloy has improved stress-strain properties, bendability properties, elongation properties and/or flexibility properties of the stent as compared with stainless steel or chromium-cobalt alloys, thus resulting in an increase life for the stent. For instance, the stent can be used in regions that subject the stent to repeated bending. Due to the improved physical properties of the stent from the novel metal alloy, the stent has improved resistance to fracturing in such frequent bending environments. These improved physical properties at least in part result from the composition of the novel metal alloy; the grain size of the novel metal alloy; the carbon, oxygen and nitrogen content of the novel metal alloy; and/or the carbon oxygen ratio of the novel metal alloy.
- The novel metal alloy has a reduce the degree of recoil during the crimping and/or expansion of the stent as compared with stainless steel or chromium-cobalt alloys. The stent formed of the novel metal alloy better maintains its crimped form and/or better maintains its expanded form after expansion due to the use of the novel metal alloy. As such, when the stent is to be mounted onto a delivery device when the stent is crimped, the stent better maintains its smaller profile during the insertion of the stent in a body passageway. Also, the stent better maintains its expanded profile after expansion so as to facilitate in the success of the stent in the treatment area.
- The novel metal alloy has improved radiopaque properties as compared to standard materials such as stainless steel or cobalt-chromium alloy, thus reducing or eliminating the need for using marker materials on the stent. For instance, the novel metal alloy is at least about 10-20% more radiopaque than stainless steel or cobalt-chromium alloy.
- The novel metal alloy is less of an irritant to the body than stainless steel or cobalt-chromium alloy, thus can result in reduced inflammation, faster healing, increased success rates of the stent. When the stent is expanded in a body passageway, some minor damage to the interior of the passageway can occur. When the body begins to heal such minor damage, the body has less adverse reaction to the presence of the novel metal alloy than compared to other metals such as stainless steel or cobalt-chromium alloy.

In one non-limiting application of the present invention, there is provided a medical device that is at least partially formed of a novel metal alloy. The novel metal alloy imparts one or more improved physical characteristics to the medical device (e.g., strength, durability, hardness, biostability, bendability, coefficient of friction, radial strength, flexibility, tensile strength, elongation, longitudinal lengthening, stress-strain properties, improved recoil properties, radiopacity, heat sensitivity, biocapatability, etc.). The novel metal alloy includes at least about 95 weight percent rhenium and molybdenum. The medical device can be designed to release one or more biological agents in a controlled and/or uncontrolled fashion; however, this is not required. For instance, when the medical device includes one or more biological agents, all of the biological agents on the medical device can be controllably released from the medical device, all of the biological agent on the medical device can be uncontrollably released from the medical device, or some of the biological agent on the medical device can be controllably released and some uncontrollably released from the medical device. The controlled release of the one or more biological agents when used, can be at least partially accomplished by molecular diffusion through one or more non-porous polymer layers; however, it will be appreciated that other, or additional mechanism can be used to control the rate of release of one or more biological agents from one or more regions of the medical device. The medical device can include one or more layers of polymer and/or biological agent on the surface structure of one or more regions of the medical device; however, this is not required. The one or more polymers, when used, can include parylene (e.g., parylene C, parylene N), PLGA, POE, PGA, PLLA, PAA, PEG, chitosan and/or derivatives of one or more of these polymers; however, other or additional polymers can be used. Many different biological agents can be used on the medical device. Such biological agents, when used, can include, but not limited to, trapidil, trapidil derivatives, taxol, taxol derivatives, cylochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof, however, it will be appreciated that other or additional biological agents can be used. The polymer and/or biological agent, when included on and or forms a portion of the medical device, can be hydrophobic or hydrophilic so as to facilitate in the controlled release of the one or more biological agents; however, this is not required. The thickness of the one or more polymer layers, when used, can be selected to facilitate in the controlled release of the one or more biological agents; however, this is not required. The molecular weight and/or molecular structure of the one or more biological agents and/or one or more polymer can be selected to facilitate in the release of the one or more biological agents; however, this is not required. The medical device can have a variety of applications such as, but not limited to placement into the vascular system, esophagus, trachea, colon, biliary tract, or urinary tract; however, the medical device can have other applications. The medical device can have one or more body members, wherein each body member includes first and second ends and a wall surface disposed between the first and second ends. Each body member can have a first cross-sectional area which permits delivery of the body member into a body passageway, and a second, expanded cross-sectional area. The expansion of the medical device body member can be accomplished in a variety of manners. Typically, the body member is expanded to its second cross-sectional area by a radially, outwardly extending force applied at least partially from the interior region of the body member (e.g. by use of a balloon, etc.); however, this is not required. When the second cross-sectional area is variable, the second cross-sectional area is typically dependent upon the amount of radially outward force applied to the body member. The medical device can be designed such that the body member expands while retaining the original length of the body member; however, this is not required. The body member can have a first cross-sectional shape that is generally circular so as to form a substantially tubular body member; however, the body member can have other cross-sectional shapes. When the medical device includes two or more body members, the two or more body members can be connected together by at least one connector member. The medical device can include rounded, smooth and/or blunt surfaces to minimize and/or prevent damage to a body passageway as the medical device is inserted into a body passageway and/or expanded in a body passageway; however, this is not required. The medical device can be treated with gamma, beta and/or e-beam radiation, and/or otherwise sterilized; however, this is not required. The medical device can have multiple sections. The sections of the medical device can have a uniform architectural configuration, or can have differing architectural configurations. Each of the sections of the medical device can be formed of a single part or formed of multiple parts which have been attached. When a section is formed of multiple parts, typically the section is formed into one continuous piece; however, this is not required. As can be appreciated, the medical device can be formed into other devices such as, but not limited to, an orthopedic device. PFO (patent foramen ovale) device, other types of grafts, guide wide, sheaths, stent catheters, electrophysiology catheters, other type of implant, valve, screw, nail, rod, hypotube, catheter, staple or cutting device, etc. The medical device can include one or more surface structures and/or micro-structures that include one or more biological agents, adhesives and/or polymers; however, this is not required. These structures can be at least partially formed by MEMS (e.g., micro-machining, etc.) technology and/or other types of technology. The structures can be designed to contain and/or fluidly connected to a passageway that includes one or more biological agents; however, this is not required. These structures can be used to engage and/or penetrate surrounding tissue or organs once the medical device has been positioned on and/or in a patient; however, this is not required. One or more polymers, adhesives and/or biological agents can be inserted in these structures and or at least partially form these structures of the medical device; however, this is not required. The structures can be clustered together or disbursed throughout the surface of the medical device. Similar shaped and/or sized surface structures can be used, or different shaped and or sized structures can be used. The surface topography of the medical device can be uniform or vary to achieve the desired operation and/or biological agent released from the medical device. As can be appreciated, the medical device or one or more regions of the medical device can be constructed by use of one or more microelectromechanical manufacturing techniques (MEMS (e.g., micro-machining, etc.)); however, this is not required. Materials that can be used by MEMS (e.g., micro-machining, etc.) technology include, but are not limited to, chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, and chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, a PEG derivative, and/or a PEG derivative. The medical device is typically formed of abiocompatible material. The amount of biological agent when used on the medical device, can be selected for different medical treatments. Typically, the amount of biological agent used in a particular layer of biological agent or included in a polymer layer is about 0.01-100 ug per mm$^2$; however, other amounts can be used. As can be appreciated, one or more biological agents and/or polymers, when used, can be placed on different regions of the medical device to achieve the desired operation and/or biological agent release from the medical device. The medical device can include one or more coatings of biological agent on the other surface of the medical device to provide a burst of biological agent to a particular site or region; however, this is not required. The one or more biological agents, when used, can be selected so as to be chemically bonded to one or more polymers; however, this is not required. The time period the one or more biological agents, when used, are released from the medical device can vary. Generally, one or more biological agents, when used, are released from the medical device for at least several days after the medical device is inserted in the body of a patient; however, this is not required. One or more biological agents, when used, can be released from the medical device for at least about one week after the medical device is inserted in the body of a patient, more typically, at least about two weeks after the medical device is inserted in the body of a patient, and even more typically, about one week to one year after the medical device is inserted in the body of a patient. As can be appreciated, the time frame that one or more of the biological agents can be released from the medical device can be longer or shorter. One or more biological agents, when used, can be released from the medical device controllably released and/or non-controllably released. The time period for the release of two or more biological agents from the medical device can be the same or different. The type of the one or more biological agents used on the medical device, the release rate of the one or more biological agents from the medical device, and/or the concentration of the one or more biological agents being released from the medical device during a certain time period is typically selected to deliver one or more biological agents directly to the area of disease after the medical device has been implanted; however, this is not required. In one non-limiting design of medical device, the medical device releases one or more biological agents over a period of time after being inserted in the body after the medical device has been implanted. In another non-limiting design of medical device, the medical device releases one or more biological agents over a period of time after being inserted in the body so that no further drug therapy is required about two weeks to one month after the medical device has been implanted. In yet another non-limiting design of medical device, the medical device releases one or more biological agents over a period of up to one day after the medical device has been implanted. In still yet another non-limiting design of medical device, the medical device releases one or more biological agents over a period of up to one week after the medical device has been implanted. In a further non-limiting design of medical device, the medical device releases one or more biological agents over a period of up to two weeks after the medical device has been implanted. In still a further non-limiting design of medical device, the medical device releases one or more biological agents over a period of up to one month after the medical device has been implanted. In yet a further non-limiting design of medical device, the medical device releases one or more biological agents over a period of up to one year after the medical device has been implanted. As can be appreciated, the time or release of one or more biological agents from the medical device can be more than one year after the medical device has been implanted. The use of the medical device can be used in conjunction with other biological agents not on and/or in the medical device. For instance, the success of the medical device can be enhanced by infusing, injecting or consuming orally the same and/or different biological agent used for anti-platelet and/or anti-coagulation therapy that is being released from the medical device. The introduction of biological agents from a source other than the medical device can have an additive or synergistic effect which can enhance the success of the medical device. Solid or liquid dosage forms of biological agents for oral administration can be used, and/or liquid dosage forms of biological agents for intravenous administration can be used. When solid dosage forms are used, such solid forms include, but are not limited to, capsules, tablets, effervescent tablets, chewable tablets, pills, powders, sachets, granules and gels. In such solid dosage forms, the biological agent can be admixed with at least one filler material such as, but not limited to, sucrose, lactose or starch; however, this is not required. Such dosage forms can also include additional substances such as, but not limited to, inert diluents (e.g., lubricating agents, etc.); however, this is not required. When capsules, tablets, effervescent tablets or pills are used, the dosage form can also include buffering agents; however, this is not required. Soft gelatin capsules can be prepared to contain a mixture of the biological agent in combination with vegetable oil or other types of oil; however, this is not required. Hard gelatin capsules can contain granules of the biological agent in combination with a solid carrier such as, but not limited to, lactose, potato starch, corn starch, cellulose derivatives of gelatin, etc; however, this is not required. Tablets and pills can be prepared with enteric coatings for additional time release characteristics; however, this is not required. Liquid dosage forms of the biological agent for oral administration can include pharmaceutically acceptable emulsions, solutions, suspensions, syrups elixirs, etc.; however, this is not required. Typically the introduction of one or more biological agents used for anti-platelet and/or anti-coagulation therapy from a source other than the medical device is about one day after the medical device has been implanted in a patient, and typically up to about one week after the medical device has been implanted in a patient, and more typically up to about one month after the medical device has been implanted in a patient; however, it can be appreciated that periods of up to 2-3 months or more can be used.

One non-limiting object of the present invention is the provision of a medical device that is at least partially formed of a novel metal alloy.

Another and/or alternative non-limiting object of the present invention is the provision of a medical device having improved procedural success rates.

Still another and/or alternative non-limiting object of the present invention is the provision of a medical device that is formed of a material that improves the physical properties of the medical device.

Yet another and/or alternative non-limiting object of the present invention is the provision of a medical device that is at least partially formed of a novel metal alloy that has increased strength and can also be used as a marker material.

Still yet another and/or alternative non-limiting object of the present invention is the provision of a medical device that at least partially includes a novel metal alloy that enables the medical device to be formed with less material without sacrificing the strength of the medical device as compared to prior medical devices.

Still yet another and/or alternative non-limiting object of the present invention is the provision of a medical device that is simple and cost effective to manufacture.

A further and/or alternative non-limiting object of the present invention is the provision of a medical device that is at least partially coated with one or more polymer coatings.

Still a further and/or alternative non-limiting object of the present invention is the provision of a medical device that is coated with one or more biological agents.

Yet a further and/or alternative non-limiting object of the present invention is the provision of a medical device that has one or more polymer coatings to at least partially control the release rate of one or more biological agents.

Still yet a further and/or alternative non-limiting object of the present invention is the provision of a medical device that includes one or more surface structures and or micro-structures.

Still a further and/or alternative non-limiting object of the present invention is the provision of a method and process for forming a novel metal alloy into a medical device.

Another and/or alternative non-limiting object of the present invention is the provision of a medical device that includes one or more surface structures, micro-structures and/or internal structures and a protective coating that at least partially covers and/or protects such structures.

Yet another and/or alternative non-limiting object of the present invention is the provision of a medical device that includes one or more markers.

Still another and, or alternative non-limiting object of the present invention is the provision of a medical device that includes and/or is used with one or more physical hindrances.

Still yet another and/or alternative non-limiting object of the present invention is the provision of a medical device that can be used in conjunction with one or more biological agents not on or in the medical device.

A further and/or alternative non-limiting object of the present invention is the provision of a method and process for forming a novel metal alloy that inhibits or prevent the formation of micro-cracks during the processing of the alloy into a medical device.

Still a further and or alternative non-limiting object of the present invention is the provision of a method and process for forming a novel metal alloy that inhibits or prevents in the introduction of impurities into the alloy during the processing of the alloy into a medical device.

These and other advantages will become apparent to those skilled in the art upon the reading and following of this description taken together with the accompanying drawings.

BRIEF DESCRIPTION OF THE DRAWINGS

Reference may now be made to the drawings, which illustrate various embodiments that the invention may take in physical form and in certain parts and arrangements of parts wherein.

DETAILED DESCRIPTION OF THE INVENTION

Figure 1:
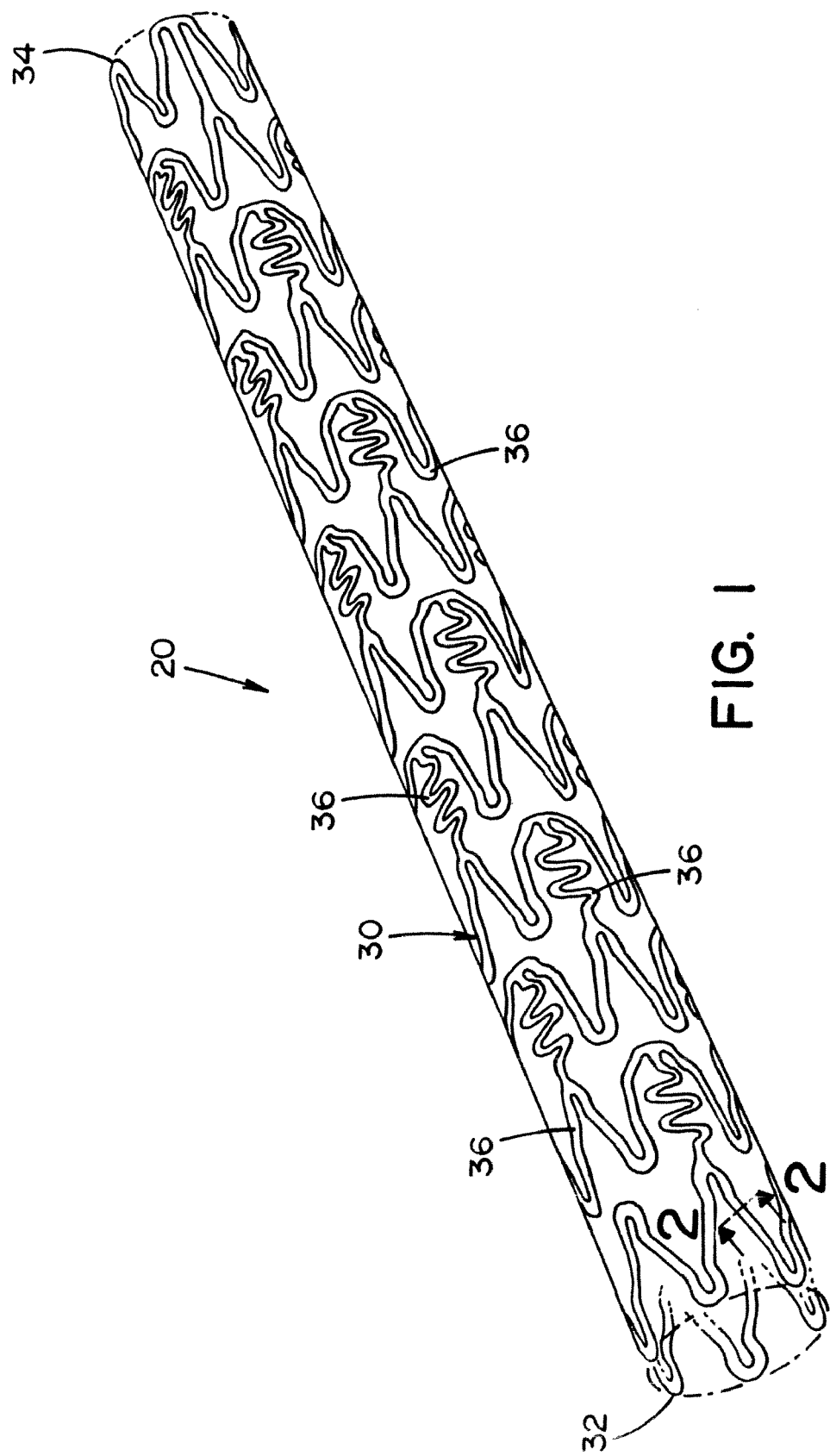
FIG. 1 is a perspective view of a section of a medical device in the form of an unexpanded stent which permits delivery of the stent into a body passageway.
Figure 2:
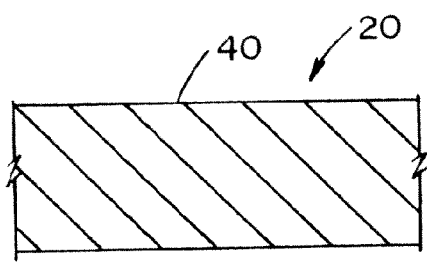
FIG. 2 is a cross-sectional view along line 2-2 of FIG. 1 illustrating the novel metal alloy material that forms the medical device.

Referring now to the drawings wherein the showings are for the purpose of illustrating embodiments of the invention only and not for the purpose of limiting the same, FIGS. 1-18 disclose a medical device in the form of a stent for use in a body passageway. The stent is particularly useful in the cardiovascular field; however, the stent can be used in other medical fields such as, but not limited to, orthopedic field, cardiology field, pulmonology field, urology field, nephrology field, gastroenterology field, gynecology field, otolaryngology field or other surgical fields. Additionally or alternatively, the medical device is not limited to a stent, thus can be in the form of many other medical devices (e.g., a staple, an orthopedic implant, a valve, a vascular implant, a pacemaker, a spinal implant, a guide wire, nail, rod, screw, etc.).

The stent, when used for vascular applications, can be used to address various medical problems such as, but not limited to, restenosis, atherosclerosis, atherogenesis, angina, ischemic disease, congestive heart failure or pulmonary edema associated with acute myocardial infarction, atherosclerosis, thrombosis, controlling blood pressure in hypertension, platelet adhesion, platelet aggregation, smooth muscle cell proliferation, vascular complications, wounds, myocardial infarction, pulmonary thromboembolism, cerebral thromboembolism, thrombophlebitis, thrombocytopenia or bleeding disorders.

As illustrated in FIG. 1, stent 20 is in the form of an expandable stent that includes at least one tubular shaped body member 30 having a first end 32, a second end 34, and member structures 36 disposed between the first and second ends. As can be appreciated, the stent can be formed of a plurality of body members connected together. Body member 30 has a first diameter which permits delivery of the body member into a body passageway. The first diameter of the body member is illustrated as substantially constant along the longitudinal length of the body member. As can be appreciated, the body member can have a varying first diameter along at least a portion of the longitudinal length of the body member. The body member also has a second expanded diameter, not shown. The second diameter typically varies in size; however, the second diameter can be non-variable in size. The stent can be expanded in a variety of ways such as by a balloon. A balloon expandable stent is typically pre-mounted or crimped onto an angioplasty balloon catheter. A balloon catheter is then positioned into the patient via a guide wire. Once the stent is properly positioned, the balloon catheter is inflated to the appropriate pressure for stent expansion. After the stent has been expanded, the balloon catheter is deflated and withdrawn, leaving the stent deployed at the treatment area. One or more surfaces of the stent can be treated so as to have generally smooth surfaces; however, this is not required. Generally, one or more ends of the stent are treated by filing, buffing, polishing, grinding, coating, and/or the like to remove or reduce the number of rough and/or sharp surfaces; however, this is not required. The smooth surfaces of the ends reduce potential damage to surrounding tissue as the stent is positioned in and/or expanded in a body passageway.

The stent as illustrated in FIG. 1 is typically designed to be inserted into a diseased area in a body passageway and to expand the diseased area to enable better or proper fluid flow through the body passageway; however, the stent can be used for other or additional reasons. In one specific non-limiting example, the stent can be used to open an obstructed blood vessel. The stent can include and/or be used with one or more biological agents used to inhibit thrombosis, in-stent restenosis, vascular narrowing and/or restenosis after the stent has been inserted into the blood vessel; however, this is not required. The one or more biological agents, when used, can also or alternatively be used to remove and/or dissolve lipids, fibroblast, fibrin, etc. from the blood vessel so as to at least partially clean the blood vessel of such substances in the region of the stent and/or down stream of the stent. As can be appreciated, the one or more biological agents, when used, can have additional or other functions.

The novel metal alloy that at least partially forms the medical device includes a majority of Mo and Re. The novel metal alloy has improved physical properties. The novel metal alloy used to at least partially form the medical device improves one or more properties (e.g., strength, durability, hardness, biostability, bendability, coefficient of friction, radial strength, flexibility, tensile strength, elongation, longitudinal lengthening, stress-strain properties, improved recoil properties, radiopacity, heat sensitivity, biocapatability, etc.) of such medical devices. In some instances, the use of the novel metal alloy can reduce the volume, bulk and or weight as compared to prior medical devices made from traditional materials; however, this is not required. The one or more materials used to form the medical device include one or more properties selected to form a medical device which promotes the success of the medical device.

The novel metal alloy that at least partially forms the stent includes a majority weight percent of Mo and Re. The novel metal alloy typically forms at least a majority weight percent of the stent; however, this is not required. As illustrated in FIG. 1, the member structures 36 of stent 20 are formed of 98-1000% of the novel metal alloy 40. In one non-limiting novel metal alloy composition, the metal alloy includes about 44-48 weight percent Re and about 52-56 weight percent Mo. In one non-limiting example, the novel metal alloy is a solid solution that includes about 44.5-47.5 weight percent Re and 52.5-55.5 weight percent Mo, a weight percent of Re plus Mo of at least about 99.9%, less than about 50 ppm carbon, less than about 10 ppm oxygen, less than about 20 ppm nitrogen, a carbon to oxygen atomic ratio of about 2.5-10:1, and no more than about 0.1 weight impurities. In another non-limiting novel metal alloy composition, the metal alloy includes about 44-48 weight percent Re, about 52-56 weight percent Mo, and up to about 0.5 weight percent Ti, Y and/or Zr. In one non-limiting example, the novel metal alloy is a solid solution that includes about 44.5-47.5 weight percent Re, 52.5-55.5 weight percent Mo, a weight percent of Mo plus Re plus Ti, Y and/or Zr that is at least about 99.9% 0.3-0.4 weight percent Ti, 0.06-0.1 weight percent Zr, 0-0.05 weight percent Y, a weight ratio of Ti:Zr of 1-3:1, less than about 50 ppm carbon, less than about 10 ppm oxygen, less than about 20 ppm nitrogen, a carbon to oxygen atomic ratio of about 2.5-10:1, and no more than about 0.1 weight impurities. The tensile elongation of the novel metal alloy is about 25-35%, the average density of the novel metal alloy is at least about 13.4 gm/cc., the average yield strength of the novel metal alloy is about at least about 98 (ksi), the average ultimate tensile strength of the novel metal alloy is about 100-150 UTS (ksi), and the average hardness of the novel metal alloy is about 80-100 (HRC) at 77° F. The 99.9 weight percent purity of the metal alloy forms a solid or homogenous solution. The unique combination of carbon and oxygen redistributes the oxygen at the grain boundary of the metal alloy, which in turn helps in reducing microcracks (defects) in the ultimately formed stent. A controlled carbon to oxygen atomic ratio can also be used to obtain a high ductility of the metal alloy which can be measured in part as tensile elongation. An increase in tensile elongation is an important attribute when forming the metal alloy into the stent. The purity of the metal alloy also results in a substantially uniform density throughout the metal alloy. The density of the solid homogeneous solution of the metal alloy results in the high radiopacity of the metal alloy. The addition of rhenium in the metal alloy improves the ductility of the molybdenum. The addition of titanium, yttrium and or zirconium, when used facilitates in grain size reduction of the novel metal alloy, improves ductility of the novel metal alloy and or increases the yield strength of the novel metal alloy. The solid or homogeneous solution of the novel metal alloy results in a novel metal alloy having the desired tensile yield strength and ultimate tensile strength of the novel metal alloy. Nitrogen in the novel metal alloy is an interstitial element that raises the Ductile Brittle Transition Temperature (DBTT). When the DBTT is too high, the novel metal alloy can become brittle. The maintenance of nitrogen below about 20 ppm overcomes this brittleness problem. The combination of these various properties of the solid or homogeneous solution of the novel metal alloy enables the novel metal alloy to be formed into a stent that has superior performance characteristics such as, but not limited from high radiopacity with thinner and narrower struts and simultaneously having a radial force adequate to retain the vessel lumen fairly open and prevent any recoil. The novel metal alloy can be fabricated from a tubing with an outer diameter as small as about 0.070 inch and with a wall thickness as small as about 0.002 inch. In one particular design, the average wall thickness after the final processing of the alloy tube is about 0.0021-0.00362 inch, and the average concentricity deviation after the final processing of the alloy tube is about 1-20%. As can be appreciated, the size values of the processed alloy rod set forth above are merely exemplary for using the novel metal alloy to form a stent for use in the vascular system of a patient. When the novel metal alloy is used to form other types of stents for use in different regions of a body, the size values of the final processed novel metal alloy can be different. The solid or homogeneous solution of the novel metal alloy has the unique characteristics of purity, ductility, grain size, tensile elongation, yield strength, and tensile strength that permits the novel metal alloy to be fabricated into the stent tubing without creating microcracks that are detrimental to the stent properties.

Referring again to FIGS. 1-2, the stent is an expandable stent that can be used to at least partially expand occluded segments of a body passageway; however, the stent can have other or additional uses. For example, the expandable stent can be used as, but not limited to, 1) a supportive stent placement within a blocked vasculature opened by transluminal recanalization, which are likely to collapse in the absence of an internal support; 2) forming a catheter passage through mediastinal and/or other veins occluded by inoperable cancers; 3) reinforcing a catheter creating intrahepatic communication between portal and/or hepatic veins in patients suffering from portal hypertension; 4) a supportive stent placement of narrowing of the esophagus, the intestine, the ureter and/or the urethra; and/or 5) a supportive stent reinforcement of reopened and previously obstructed bile ducts. Accordingly, use of the term "stent" encompasses the foregoing or other usages within various types of body passageways, and also encompasses use for expanding a body passageway. The stent can be implanted or applied in a body passageway by techniques such as, but not limited to, balloon delivery, sheath catheter delivery, etc.

Figure 19:
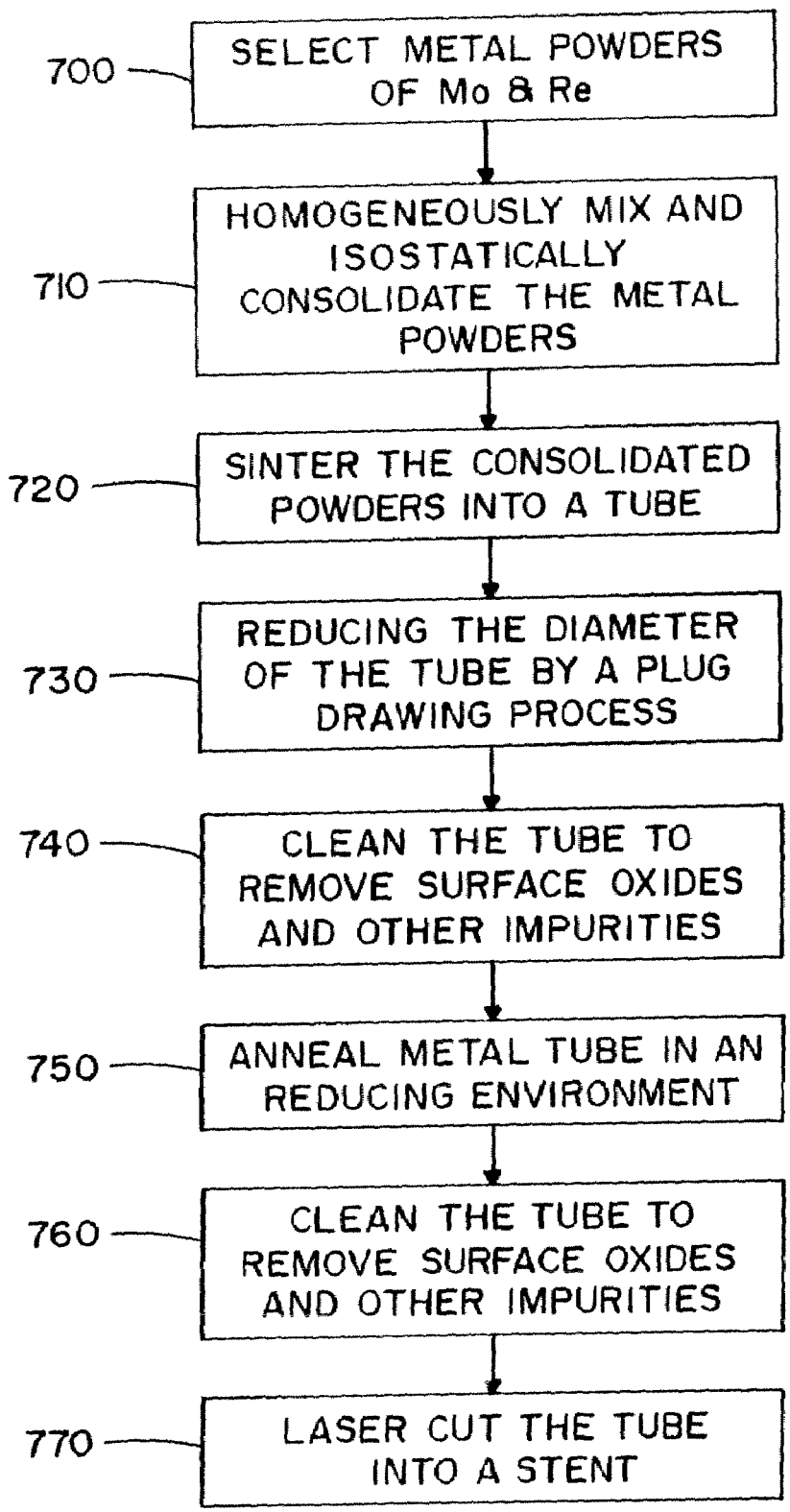

The novel metal alloy can be formed into a stent by a variety of manufacturing processes. One non-limiting process for forming the stent as illustrated in FIG. 19. As illustrated in this non-limiting process, the first step to form a stent is to form a tube of a solid solution of molybdenum and rhenium alloy. The tube can be form in a variety of ways. Process step 700 illustrates that metal powders of molybdenum and rhenium are selected to form the tube. The powders of molybdenum and rhenium constitute a majority weight percent of the materials used to form the metal tube. Small amounts of an additional metal such as titanium, yttrium and/or zirconium can also be used; however, this is not required. The purity of the metal powders is selected to minimize the carbon, oxygen and nitrogen content in the metal powder. Typically the carbon content of the metal powders is less than about 150 ppm, the oxygen content of the metal powders is less than about 100 ppm and the nitrogen content of the metal powders is less than about 40 ppm.

After the metal powders have been selected, the metal powders are substantially homogeneously mixed together as illustrated in process step 710. After the metal powders are mixed together, the metal powders are isostatically consolidated to form a tube. One non-limiting isostatic consolidation process is a cold isostatic pressing (CIP) process. The isostatic consolidation process typically occurs in a vacuum environment, an oxygen reducing environment, or in an inert atmosphere. The average density of the metal tube obtained by the isostatic consolidation process is about 80-90% of the final average density of the tube. One non-limiting composition of the tube is a solid solution of about 44-48 weight percent rhenium, about 52-56 weight percent molybdenum, up to about 0.5 weight percent Ti, Y and/or Zr, and no more than about 0.1 weight impurities. After the metal powder has been pressed together, the metal power is sintered to fuse the metal powders together and to form the tube of novel metal alloy as illustrated in step 720. The sinter of the metal powders occurs at a temperature of about 2000-2500° C. for about 5-120 minutes; however, other temperatures and/or sintering time can be used. The sintering of the metal powder typically takes place in an oxygen reducing environment to inhibit or prevent impurities from becoming embedded in the novel metal alloy and/or to further reduce the amount of carbon and/or oxygen in the formed tube. After the sintering process, the tube is formed of a solid solution of the novel metal alloy and has an as-sintered average density of about 90-99% the minimum theoretical density of the novel metal alloy. Typically, the sintered tube has a final average density of about 13-14 gm/cc. The length of the formed tube is typically about 48 inches or less; however, longer lengths can be formed. The average concentricity deviation of the tube is typically about 1-18%. In one non-limiting tube configuration, the tube has an inner diameter of about 0.31 inch plus or minus about 0.002 inch and an outer diameter of about 0.5 inch plus or minus about 0.002 inch. The wall thickness of the tube is about 0.095 inch plus or minus about 0.002 inch. As can be appreciated, this is just one example of many different sized tubes that can be formed.

The tube can be cleaned after the tube has been form sintered, however, this is not required. The cleaning of the tube is used to remove impurities and/or contaminants from the surfaces of the tube. Impurities and contaminants (e.g., carbon, oxygen, etc.) can become incorporated into the novel metal alloy during the processing of the tube. The inclusion of impurities and contaminants in the novel metal alloy can result in premature micro-cracking of the novel metal alloy and/or the adverse affect on one or more physical properties of the novel metal alloy. The cleaning of the tube can be accomplished by a variety of techniques such as, but not limited to, 1) using a solvent (e.g. acetone, methyl alcohol, etc.) and wiping the novel metal alloy with a Kimwipe or other appropriate towel, and/or 2) by at least partially dipping or immersing the novel metal alloy in a solvent and then ultrasonically cleaning the novel metal alloy. As can be appreciated, the tube can be cleaned in other or additional ways.

After the tube has been sintered, and optionally cleaned, the tube is then drawn through a die one or more times to reduce the inner and outer diameter of the tube and the wall thickness of the tube to the desired size. As illustrated in process step 730, the tube is reduced in size by the use of a plug drawing process. During the plug drawing process, the tube is heated (i.e., up to about 300° C.) and protected in a vacuum environment, an oxygen reducing environment, or inert environment. One non-limiting oxygen reducing environment includes argon and about 1-10 volume percent hydrogen. The amount of outer diameter draw down of the tube each time the tube is plug drawn is typically no more than about 10%. Controlling the degree of draw down facilitates in preventing the formation of micro-cracks during the drawing process. After each drawing process, the tube can be cleaned as illustrated in step 740; however, this is not required.

Prior to the tube being drawn down more than about 35-45% from its original outer diameter after the sintering process, the tube is annealed as illustrated in process step 750. If the tube is to be further drawn down after being initially annealed, a subsequent annealing process should be completed prior to the outer diameter of the tube being drawn down more than about 35-45% since a previous annealing process. As such, the tube should also be annealed at least once prior to the tube outer diameter being drawn down more than about 35-45% since being originally sintered or being previously annealed. This controlled annealing facilitates in preventing the formation of micro-cracks during the drawing process. The annealing process of the tube typically takes place in a vacuum environment, an inert atmosphere, or an oxygen reducing environment (e.g., argon, argon and 1-10% hydrogen, etc.) at a temperature of about 1400-1500° C. for a period of about 5-30 minutes; however, other temperatures and/or times can be used. The use of an oxygen reducing environment during the annealing process can be used to reduce the amount of oxygen in the tube. The chamber in which the tube is annealed should be substantially free of impurities such as, but not limited to carbon, oxygen, and/or nitrogen. The annealing chamber typically is formed of a material that will not impart impurities to the tube as the tube is being annealed. One non-limiting material that can be used to form the annealing chamber is a molybdenum TZM alloy.

Prior to each annealing process, the tube is cleaned and/or pickled to remove oxides and/or other impurities from the surface of the tube as illustrated in process step 740. Typically the tube is cleaned by first using a solvent (e.g. acetone, methyl alcohol, etc.) and wiping the novel metal alloy with a Kimwipe or other appropriate towel, and/or by at least partially dipping or immersing the tube in a solvent and then ultrasonically cleaning the novel metal alloy. As can be appreciated, the tube can be cleaned in other and/or additional ways. After the tube has been cleaned by use of a solvent, the tube is typically further cleaned by use of a pickling process. The pickling process includes the use of one or more acids to remove impurities from the surface of the tube. Non-limiting examples of acids that can be used as the pickling solution include, but are not limited to, nitric acid, acetic acid, sulfuric acid, hydrochloric acid, and/or hydrofluoric acid. The acid solution and acid concentration and time of pickling are selected to remove oxides and other impurities on the tube surface without damaging or over etching the surface of the tube. During the pickling process, the tube is fully or partially immersed in the pickling solution for a sufficient amount of time to remove the impurities from the surface of the tube. After the tube has been pickled, the tube is typically rinsed with a solvent (e.g., acetone, methyl alcohol, etc.) to remove any pickling solution from the tube and then the tube is allowed to dry. The cleaning of the tube prior to the tube being annealed removes impurities and/or other materials from the surfaces of the tube that could become permanently imbedded into the tubing during the annealing processes. These imbedded impurities could adversely affect the physical properties of the novel metal alloy as the tube is formed into a medical device, and/or can adversely affect the operation and/or life of the medical device. As can be appreciated, the tube can be again cleaned and/or pickled after being annealed and prior to being drawn down in the plug drawing process; however, this is not required.

Process steps 730-750 can be repeated as necessary until the tube is drawn down to the desired size. In one non-limiting process, a tube that is originally formed after being sintered has an inner diameter of about 0.31 inch plus or minus about 0.002 inch, an outer diameter of about 0.5 inch plus or minus about 0.002 inch, and a wall thickness of about 0.095 inch plus or minus about 0.002 inch. After the tube has been fully drawn down, the tube has an outer diameter of about 0.070 inch, a wall thickness of about 0.0021-0.00362 inch, and the average concentricity deviation of less than about 10%. Such small sizes for stents which can be successfully used in a vascular system have heretofore not been possible when formed by other types of metal alloys. Typically, the wall thickness of stent had to be at least about 0.0027-0.003 inch, or the stent would not have sufficient radial force to maintain the stent in an expanded state after being expanded. The novel metal alloy of the present invention is believed to be able to have a wall thickness of as small as about 0.0015 inch and still have sufficient radial force to maintain a stent in an expanded state after being expanded. As such, when a tube is formed into a stent, the wall thickness of the tube can be drawn down to less than about 0.0027 inch to form a stent. As can be appreciated, this is just one example of many different sized tubes that can be formed by the process of the present invention.

Once the tube has been drawn down to its final size, the tube is typically cleaned (Process Step 740), annealed (Process Step 750) and then again cleaned (Process Step 760). The cleaning step of process step 760 can include merely solvent cleaning, or can also include pickling.

After the tube has been cleaned in process step 760, the tube is then cut into the form of a stent as illustrated in FIG. 19. As can be appreciated, other stent designs can be formed during the cutting process as set forth in process step 770. The cutting of the tube is typically conducted by a laser. The laser that is used to cut the tube is selected so that the beam strength used to heat the tube can obtain a cutting temperature of at least about 2350° C. Non-limiting examples of lasers that can be used include a pulsed YAG-ND or $CO_2$ laser. The cutting of the tube by the laser occurs in an oxygen reducing environment such as an argon and 1-10 percent by volume hydrogen environment; however, a vacuum environment, an inert environment, or another type of oxygen reducing environment can be used. During the cutting of the tube, the tube is typically stabilized so as to inhibit or prevent vibration of the tube during the cutting process, which vibrations can result in the formation of micro-cracks in the tube as the tube is cut. The tube is typically stabilized by an apparatus formed of molybdenum, rhenium, tungsten, molybdenum TZM alloy, ceramic, etc. so as to not introduce contaminates to the tube during the cutting process; however, this is not required. The average amplitude of vibration during the cutting of the tube is typically no more than about 50% the wall thickness of the tube. As such, for a tube having a wall thickness of about 0.0024 inch, the average amplitude of vibration of the tube during the cutting process is no more than about 0.0012 inch.

The formed stent typically has a tensile elongation of about 25-35%, an average density of about 13.4-14 gm/cc., an average yield strength of at least about 100 (ksi), an average ultimate tensile strength of about 100-150 UTS (ksi), and an average hardness of about 80-100 (HRC) at 77° F. The solid or homogeneous solution of the metal alloy that is used to form the stent has the unique characteristics of purity, ductility, grain size, tensile elongation, yield strength and ultimate tensile strength that permits 1) the metal alloy to be fabricated into the stent from the tube without creating microcracks which are detrimental to the stent properties, and 2) the manufacture of a stent that has improved physical properties over stents formed from different materials.

After the stent has been cut, the stent can be further processed; however, this is not required. The one or more processes can include, but are not limited to, 1) electropolishing the stent, 2) treating one or more surfaces of the stent to create generally smooth surfaces (e.g., filing, buffing, polishing, grinding, coating, etc.), 3) at least partially coating the stent with one or more biological agents, 4) at least partially coating the stent with one or more polymers, 5) forming one or more surface structures and/or micro-structures on one or more portions of the stent, and/or 6) inserting one or more markers on one or more portions of the stent.

The stent can include one or more coating and/or one or more surface structures and/or micro-structures as illustrated in FIGS. 3-18. The one or more surface structures and/or micro-structures can be formed by a variety of processes (e.g., machining, chemical modifications, chemical reactions, MEMS (e.g., micro-machining, etc.), etching, laser cutting, etc.). The one or more coatings and/or one or more surface structures and/or micro-structures of the stent can be used for a variety of purposes such as, but not limited to, 1) increasing the bonding and/or adhesion of one or more biological agents, adhesives, marker materials and/or polymers to the stent, 2) changing the appearance or surface characteristics of the stent, and/or 3) controlling the release rate of one or more biological agents.

Figure 3:
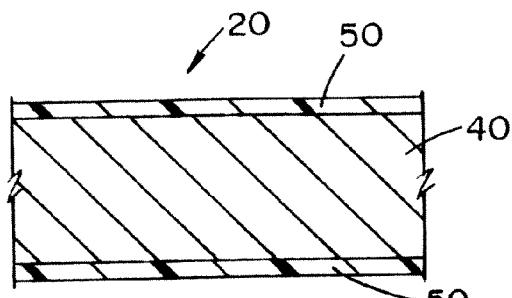
FIG. 3 is a cross-sectional view along line 2-2 of FIG. 1 illustrating the novel metal alloy that forms the medical device that includes a polymer coating or biological agent.

As illustrated in FIG. 3, the novel metal alloy 40 that form the body of stent 20 can be coated with one or more biological agents or polymers 50 that can be used to improve the functionality or success of the stent. The one or more polymer coatings can be porous or non-porous polymers. Non-limiting examples of the one or more polymers that can be coated on one or more regions of the novel metal alloy 40 include, but are not limited to, parylene, a parylene derivative, chitosan, a chitosan derivative, PLGA, a PLGA derivative, PLA, a PLA derivative. PEVA, a PEVA derivative. PBMA, a PBMA derivative, POE, a POE derivative, PGA, a PGA derivative, PLLA, a PLLA derivative, PAA, a PAA derivative, PEG, a PEG derivative, or combinations thereof. The one or more biological agents can include, but are not limited to, antibiotic agents, anti-body targeted therapy agents, anti-hypertensive agents, anti-microbial agents, anti-mitotic agents, anti-oxidants, anti-polymerases agents, anti-proliferative agents, anti-secretory agents, anti-tumor agents, anti-viral agents, bioactive agents, chemotherapeutic agents, cellular components, cytoskeletal inhibitors, drug, growth factors, growth factor antagonists, hormones, immunosuppressive agents, living cells, non-steroidal anti-inflammatory drugs, radioactive materials, radio-therapeutic agents, thrombolytic agents, vasodilator agents, etc. Non-limiting examples of biological agents that can be used include a vascular active agent that inhibits and/or prevents restenosis, vascular narrowing and/or in-stent restenosis such as, but not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. As can be appreciated, other or additional biological agents can be included on the stent to improve the functionality or success of the stent. The amount of biological agent delivered to a certain region of a patient's body can be controlled by varying the type of biological agent, the coating thickness of the biological agent, the drug concentration of the biological agent, the solubility of the biological agent, the location the biological agent that is coated and/or impregnated on and/in the stent, the amount of surface area of the stent that is coated and/or impregnated with the biological agent, the location of the biological agent on the stent, etc.

When one or more biological agents are included on and/or in the stent, the one or more biological agents can be controllably released and/or immediately released to optimize their effects and/or to compliment the function and success of the stent. The controlled release can be accomplished by 1) controlling the size of the surface structures, micro-structures and/or internal structures in the stent, and/or 2) using one or more polymer coatings; however, other or additional mechanisms can be used to control the release rate of one or more biological agents from the stent. The controlled release can be accomplished by 1) controlling the size of the surface structures, micro-structures and/or internal structures in the stent, and/or 2) using one or more polymer coatings; however, other or additional mechanisms can be used to control the release rate of one or more biological agents from the stent. For example, the amount of biological agent delivered to a certain region of a patient's body can be controlled by, but not limited to, one or more of the following: a) selecting the type of biological agent to be used on and/or in the stent, b) selecting the amount of biological agent to be used on and/or in the stent, c) selecting the coating thickness of the biological agent to be used on the stent, d) selecting the drug concentration of the biological agent to be used on and or in the stent, e) selecting the solubility of the biological agent to be used on and or in the stent, f) selecting the location the biological agent that is to be coated and/or impregnated on and/in the stent, g) selecting the amount of surface area of the stent that is coated and or impregnated with the biological agent, h) selecting the location of the biological agent on the stent, i) selecting the size, shape, amount and/or location of the one or more surface structures, micro-structures and/or internal structures of the stent that include and/or are integrated with the biological agent, j) selecting the type and/or amount of polymer to be mixed with the biological agent, k) selecting the type, amount and/or coating thickness of the polymer coating used to at least partially coat and/or encapsulate the biological agent, etc. The one or more biological agents can be combined with and/or at least partially coated with a polymer that affects the rate at which the biological agent is released from the stent; however, this is not required. The polymer coating can also or alternatively be used to assist in binding the one or more biological agents to the stent; however, this is not required. The polymer coating, when used, can be biodegradable or biostable. The polymer coating can be formulated to form a bond with the biological agent to the stent; however, this is not required. The one or more polymers used in the polymer coating and the one or more biological agents can be mixed together prior to being applied to the stent; however, this is not required. The one or more biological agents that are used in combination with a one or more polymers in the polymer coating can control the release of the biological agent by molecular diffusion; however, this is not required. The thickness of the polymer coating can be about 0.5-25μ; however, other coating thickness can be used. The time period the one or more biological agents are released from the stent can vary. The one or more biological agents, when used, can be coated on the surface of the novel metal alloy, on the surface of one or more polymer layers, and/or mixed with one or more polymer layers. One or more biological agents can also be coated on the top surface of stent 20. At least one biological agent can be entrapped within and/or coated over with a non-porous polymer layer to at least partially control the release rate of the biological rate; however, this is not required. When a non-porous polymer layer is used on the stent, the non-porous polymer typically includes parylene C, parylene N, parylene F and/or a parylene derivative; however, other or additional polymers can be used. Various coating combinations can be used on the stent. For instance, a polymer layer that includes one or more polymers can be coated on the top of the layer of one or more biological agents; however, this is not required. In another example, the novel metal alloy 40 can includes a layer of one or more polymers. A layer of one or more biological agent can be coated on the top of the layer of one or more polymers; however, this is not required. Furthermore, one or more polymers can be coated on the layer of one or more biological agents; however, this is not required. As can be appreciated other coating combinations can be used. Generally, one or more biological agent are released from the stent for at least several days after the stent is inserted in the body of a patient; however, this is not required. Generally, one or more biological agents are released from the stent for at least about 1-7 days after the stent is inserted in the body of a patient, typically at least about 1-14 days after the stent is inserted in the body of a patient, and more typically about 1-365 days after the stent is inserted in the body of a patient; however, this is not required. As can be appreciated, the time frame that one or more of the biological agents are released from the stent can be shorter or longer. The one or more biological agents that are released from the stent can be controllably released and/or non-controllably released. The time period for the release of two or more biological agents from the stent can be the same or different. The type of the one or more biological agents used on the stent, the release rate of the one or more biological agents from the stent, and/or the concentration of the one or more biological agents being released from the stent during a certain time period is typically selected to deliver the one or more biological agents to the area of treatment and/or disease. When the stent is used in the vascular system, the one or more biological agent can be used to inhibit or prevent thrombosis, restenosis, vascular narrowing and/or in-stent restenosis after the stent has been implanted; however, this is not required. When the stent is use in the vascular system, the biological agent that is generally included on and/or in the stent is, but not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CS F derivatives, or combinations thereof; however, it will be appreciated that other or additional biological agents can be used. In addition, many other or additional biological agents can be included on and/or in the stent such as, but not limited to, the following categories of biological agents: thrombolytics, vasodilators, anti-hypertensive agents, anti-microbial or anti-biotic, anti-mitotic, anti-proliferative, anti-secretory agents, non-steroidal anti-inflammatory drugs, immunosuppressive agents, growth factors and growth factor antagonists, chemotherapeutic agents, anti-polymerases, anti-viral agents, anti-body targeted therapy agents, hormones, anti-oxidants, radio-therapeutic agents, radiopaque agents and/or radio-labeled agents.

The surface of the novel metal alloy 40 can be treated to enhance the coating of the stent and or to enhance the mechanical characteristics of the stent; however, this is not required. Such surface treatment techniques include, but are not limited to, cleaning, buffing, smoothing, etching (chemical etching, plasma etching, etc.), etc. When an etching process is used, various gasses can be used for such a surface treatment process such as, but not limited to, carbon dioxide, nitrogen, oxygen, Freon, helium, hydrogen, etc. The plasma etching process can be used to clean the surface of the stent, change the surface properties of the stent so as to affect the adhesion properties, lubricity properties, etc. of the surface of the stent. As can be appreciated, other or additional surface treatment processes can be used prior to the coating of one or more biological agents and/or polymers on the surface of the stent.

As illustrated in FIGS. 3-7, various coating combinations can be used on the stent. As indicated above with reference to FIG. 3, the base structure 40 of the stent includes a layer 50 of biological agent and/or polymer. The layer of biological agent and/or polymer can include one or more biological agents and/or polymers. In one non-limiting example, layer 50 includes one or more biological agents that include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. In one non-limiting example, layer 50 includes one or more polymers. The polymer layer can include one or more polymers. The polymer layer can include one or more porous polymers and/or non-porous polymers, and/or biostable and/or biodegradable polymers. When the stent includes and or is coated with one or more polymers, such polymers can include, but are not limited to, parylene, parylene C, parylene N, parylene F, PLGA, PEVA, PLA, PBMA, POE, PGA. PLLA, PAA, PEG, chitosan and/or derivatives of one or more of these polymers. The polymer layer, when including one or more non-porous polymers, at least partially controls a rate of release by molecular diffusion of the one or more biological agents in layer 50. The one or more non-porous polymers can include, but are not limited to, parylene C, parylene N, parylene F and/or a parylene derivative.

Figure 4:
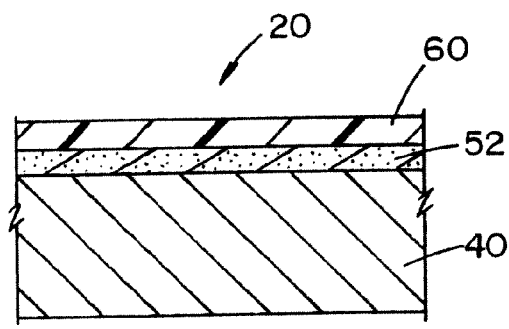
FIG. 4 is a cross-sectional view along line 2 of FIG. 1 illustrating one type of coating on a medical device.

As illustrated in FIG. 4, the base structure 40 of the stent 20 includes a layer 52 of biological agent. The layer of biological agent can include one or more biological agents. In one non-limiting example, the biological agent includes trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-C SF, GM-CSF derivatives, or combinations thereof. A polymer layer 60 is coated on the top of layer 52. The polymer layer can include one or more polymers. The polymer layer can include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the polymer layer includes one or more non-porous polymers to at least partially control a rate of release by molecular diffusion of the one or more biological agents of layer 52 from stent 20. The one or more non-porous polymers can include, but is not limited to, parylene C, parylene N, parylene F and/or a parylene derivative.

Figure 5:
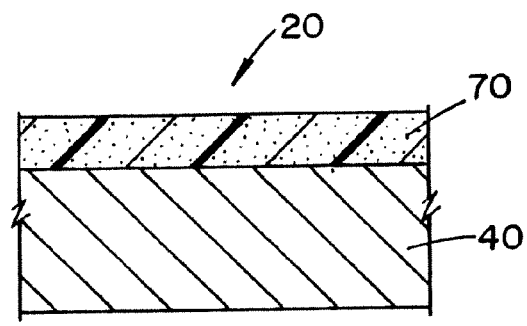
FIG. 5 is a cross-sectional view along line 2-2 of FIG. 1 illustrating another type of coating on a medical device.
Figure 6:
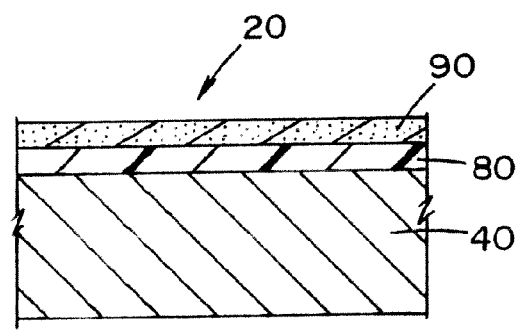
FIG. 6 is a cross-sectional view along line 2-2 of FIG. 1 illustrating another type of coating on a medical device.
Figure 7:
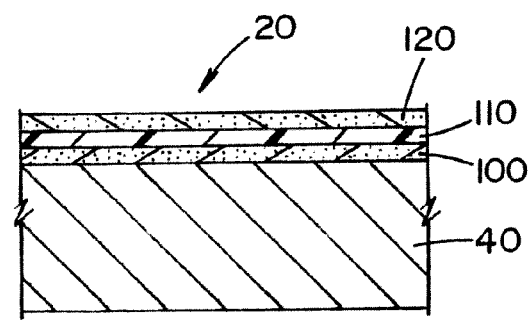
FIG. 7 is a cross-sectional view along line 2-2 of FIG. 1 illustrating another type of coating on a medical device.
Figure 8:
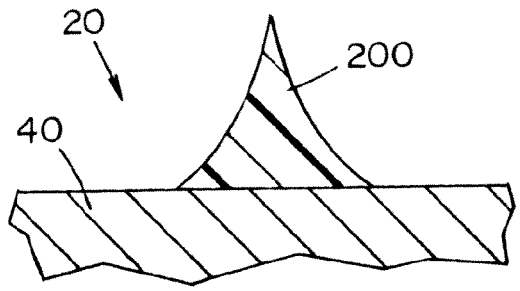
FIGS. 8 and 9 are a cross-sectional view along line 2-2 of FIG. 1 illustrating the novel metal alloy that includes one or more micro-needles on the surface of the novel metal alloy.
Figure 9:
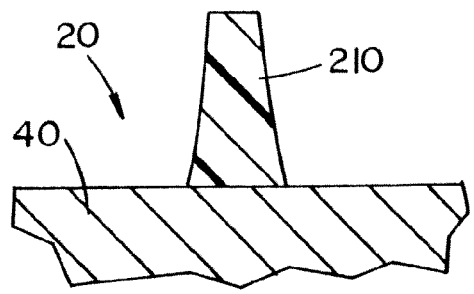
Figure 10:
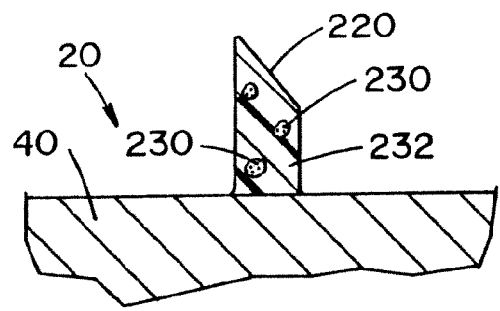
FIG. 10 is a cross-sectional view along line 2-2 of FIG. 1 illustrating the novel metal alloy that includes a plurality of micro-needles on the surface of the novel metal alloy which are formed of one or more polymers and biological agents.
Figure 11:
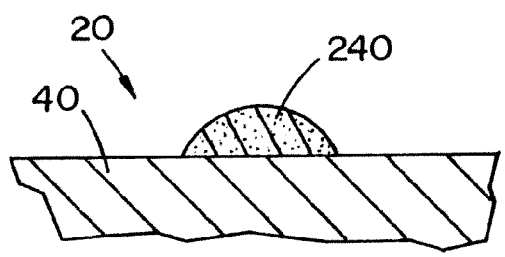
FIG. 11 is a cross-sectional view along line 2-2 of FIG. 1 illustrating the novel metal alloy that includes one or more micro-structures on the surface of the novel metal alloy.

As illustrated in FIG. 5, the base structure 40 of stent 20 includes a layer 70 of polymer and biological agent. Layer 70 can include one or more biological agents mixed with one or more polymers. In one non-limiting example, the one or more biological agents include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The one or more polymers can include one or more porous and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the one or more polymers included in layer 70 include a non-porous polymer to at least partially control a rate of release by molecular diffusion of the one or more biological agents in layer 70. The non-porous polymer can include, but is not limited to parylene C, parylene N, parylene F and or a parylene derivative.

As illustrated in FIG. 6, the base structure 40 of stent 20 includes a layer 80 of polymer. Layer 80 can include one or more porous polymers and/or non-porous polymers, and or one or more biostable and or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. The one or more non-porous polymers, when used, can include, but are not limited to, parylene C, parylene N, parylene F and or a parylene derivative. A layer 90 of one or more biological agents is coated on top of polymer layer 80. Polymer layer 80 can be used to facilitate in the securing of layer 90 to the stent; however, this is not required. In one non-limiting example, the one or more biological agents include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The placement of a layer of biological agent on the top surface of the stent can provide a burst of biological agent in the treatment area (e.g., body passageway etc.) after insertion of the stent. In one non-limiting example, the one or more biological agents include trapidil and or derivatives thereof.

As illustrated in FIG. 7, the base structure 40 of stent 20 includes a layer 100 of one or more biological agents. In one non-limiting example, the one or more biological agents include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. A polymer layer 110 is coated on the top of layer 100. The polymer layer can include one or more polymers. The polymer layer can include one or more porous polymers and or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the polymer layer includes one or more non-porous polymers to at least partially control a rate of release by molecular diffusion of the one or more biological agents of layer 100 from stent 20. The one or more non-porous polymers can include, but are not limited to, parylene C, parylene N, parylene F and/or a parylene derivative. A layer 120 of biological agent is coated on top of polymer layer 110. Layer 120 can include one or more biological agents. In one non-limiting example, the one or more biological agents include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The placement of a layer of biological agent on the top surface of the stent provide can provide a burst of one or more biological agents in the treatment area (e.g., body passageway, etc.) after insertion of the stent. In one non-limiting example, the one or more biological agents include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. As can be appreciated, other combinations of polymer layer and layer of biological agent can be used on the stent. These other combinations are also encompassed within the scope of the present invention.

Referring now to FIGS. 8-10, the novel metal alloy 40 of stent 20 includes one or more needles or micro-needles 200, 210, 220 formed on the surface of the novel metal alloy. These needles or micro-needles can be formed by MEMS (e.g., micro-machining, etc.) technology and/or by other processes. As illustrated in FIGS. 8-10, the needles or micro-needles can have a variety of shapes and sizes. The needles or micro-needles can be at least partially formed from one or more polymers and/or biological agents. It can be appreciated that the needles or micro-needles can be at least partially formed of other of additional material such as, but not limited to one or more adhesives, etc. As illustrated in FIG. 10, the needles or micro-needles include a combination of one or more polymers 232 and/or one or more biological agents 230. As can be appreciated, one or more layer of one or more biological agents and/or polymers can be coated on the needles or micro-needles; however, this is not required. When the one or more needles or micro-needles include and/or are coated with one or more biological agents, such biological agents can include, but are not limited to, trapidil, trapidil derivatives, 5-Phenylmethimazole, 5-Phenylmethimazole derivatives, GM-CSF, GM-CSF derivatives, or combinations thereof; however other or additional biological agents can be used. The use of one or more biological agents to coat the top surface of the needles or micro-needles can provide a burst of biological agent in the interior of the blood vessel and/or the blood vessel itself during and/or after insertion of the stent.

Referring now to FIG. 11, the novel metal alloy 40 of stent 20 includes one or more surface structures or micro-structures 240 in the form of a mound; however, it can be appreciated that other or additional shapes can be used. The mound is formed on the surface of the novel metal alloy. The mound can be formed by MEMS (e.g., micro-machining, etc.) technology and/or by other processes. The mound is shown to be formed of one or more biological agents; however, it can be appreciated that the mound can be formed of one or more polymers or a combination of one or more polymers and biological agents. As can also be appreciated, other or additional materials can be used to at least partially form the mound. The one or more biological agents can include, but are not limited to, trapidil, trapidil derivatives, 5-Phenylmethimazole, 5-Phenylmethimazole derivatives, GM-CSF, GM-CSF derivatives, or combinations thereof; however other or additional biological agents can be used. The one or more biological agents used to form the mound can provide a burst of biological agent in the interior of a body passageway and/or the body passageway itself during and/or after insertion of the stent in the body passageway; however, this is not required. As can be appreciated, a layer of one or more polymers can be coated on the mound; however, this is not required. The polymer layer can be used to control the release rate of the one or more biological agents from the mound; however, this is not required. The polymer layer can also or alternatively provide protection to the mound structure; however, this is not required. When the mound includes and/or is coated with one or more polymers, such polymers can include, but are not limited to, parylene, parylene C, parylene N, parylene F, PLGA, PEVA, PLA, PBMA, POE, PGA, PLLA, PAA, PEG, chitosan and/or derivatives of one or more of these polymers.

Figure 12:
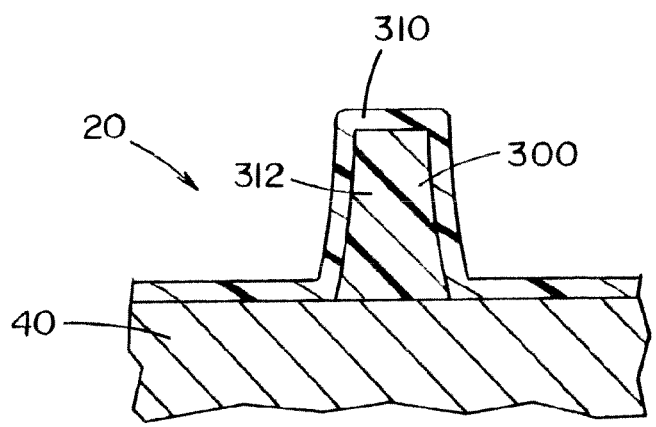
FIG. 12 is a cross-sectional view along line 2-2 of FIG. 1 illustrating one or more micro-needles on the surface of the novel metal alloy which one or more micro-needles are formed from one or more polymers and or biological agents and are coated with one or more polymers and/or biological agents.

Referring now to FIG. 12, the novel metal alloy 40 of stent 20 includes one or more needles or micro-needles 300. The one or more needles or micro-needles are formed on the surface of the novel metal alloy. The one or more needles or micro-needles are formed from one or more polymers 312. As can be appreciated, the one or more needles or micro-needles also or alternatively be formed from one or more biological agents and/or adhesives. The polymer can be porous, non-porous, biodegradable and or biostable. Polymers that can be used to at least partially form the one or more needles or micro-needles include, but are not limited to, Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers; however, other or additional polymers can be used. One or more polymer layers 310 are coated on the top of the one or more needles or micro-needles. As can be appreciated, layer 310 also or alternatively be formed from one or more biological agents and/or adhesives. The one or more polymer layers 310 can include one or more polymers. Layer 310 can include one or more porous polymer and/or non-porous polymers. Layer 310 can include one or more biostable and/or biodegradable polymers. The one or more polymers can include, but is not limited to, parylene, parylene C, parylene N, parylene F, PLGA, PEVA, PLA, PBMA, POE, PGA, PLLA, PAA, PEG, chitosan and/or derivatives of one or more of these polymers; however, other or additional polymers can be used. The one or more polymers that form the layer 310 can be the same or different from the one or more polymers that form the one or more needles or micro-needles 300. Layer 310 can be used to 1) provide protection to the structure of the one or more needles or micro-needles 300, 2) at least partially control a rate of degradation of the one or more needles or micro-needles 300, and/or 3) at least partially control a rate of release of one or more biological agents on and/or in the one or more needles or micro-needles 300. As can be appreciated, layer 310 can have other or additional functions. The surface of the layer 310 can be or include one or more layers of one or more biological agents to provide a burst of biological agent in the interior of a body passageway and/or in the body passageway itself during and/or after insertion of the stent; however, this is not required. The one or more biological agents that can be used can include, but are not limited to, trapidil, trapidil derivatives, 5-Phenylmethimazole, 5-Phenylmethimazole derivatives, GM-CSF, GM-CSF derivatives, or combinations thereof; however other or additional biological agents can be used.

Figure 13:
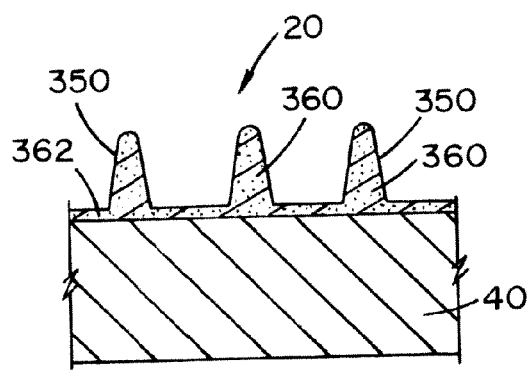
FIG. 13 is a cross-sectional view along line 2-2 of FIG. 1 illustrating micro-needles on the surface of the medical device that are formed of a biological agent.

Referring now to FIG. 13, the base structure 40 of stent 20 includes one or more needles or micro-needles 350. The one or more needles or micro-needles are formed on the surface of the base structure. The one or more needles or micro-needles are formed from one or more biological agents and/or one or more polymer 360. A layer 362 of biological agent and/or polymer is also termed on the surface of the base structure. In one non-limiting example, the one or more needles or micro-needles 350 are formed from one or more biological agents that include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. In this non-limiting example, layer 362 is also formed from one or more biological agents that include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. As can be appreciated, the one or more biological agents in layer 362 and forming the one or more needles or micro-needles 350 can be the same or different. The use of one or more biological agents to coat the top surface of the base structure and/or to form one or more needles or micro-needles can provide a burst of one or more biological agent in the treatment area (e.g., body passageway, etc.) after insertion of the stent. In another non-limiting example, the one or more needles or micro-needles 350 are formed from one or more biological agents that include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. In this non-limiting example, layer 362 is formed from one or more polymers. The polymer layer can include one or more polymers. The polymer layer can include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. When the one or more polymers are non-porous polymers, the one or more non-porous polymers can include, but are not limited to, parylene C, parylene N, parylene F and/or a parylene derivative. The use of one or more biological agents to form one or more needles or micro-needles can provide a burst of one or more biological agent in the treatment area (e.g., body passageway, etc.) after insertion of the stent. In still another non-limiting example, the one or more needles or micro-needles 350 are formed from one or more polymers. The polymer layer can include one or more polymers. The polymer layer can include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. When the one or more polymers are non-porous polymers, the one or more non-porous polymers can include, but are not limited to, parylene C, parylene N, parylene F and/or a parylene derivative. In this non-limiting example, layer 362 is formed from one or more biological agents that include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The use of one or more biological agents to form layer 362 can provide a burst of one or more biological agent in the treatment area (e.g., body passageway, etc.) after insertion of the stent; however, this is not required.

Figure 14:
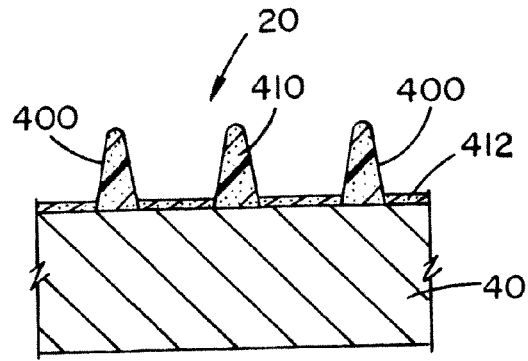
FIG. 14 is a cross-sectional view along line 2-2 of FIG. 1 illustrating micro-needles on the surface of the medical device that are formed of a biological agent and polymer.

Referring now to FIG. 14, the base structure 40 of stent 20 includes one or more needles or micro-needles 400. The one or more needles or micro-needles are formed on the surface of the base structure. The one or more needles or micro-needles are formed from one or more biological agents and one or more polymers 410. A layer 412 of biological agent and/or polymer is also formed on the surface of the base structure. As can be appreciated, the composition of layer 412 and forming the composition of the one or more needles or micro-needles 400 can be the same or different. In one non-limiting example, the one or more biological agents that at least partially form layer 412 and/or the one or more needles or micro-needles 400 include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The one or more polymers that at least partially form layer 412 and/or the one or more needles or micro-needles 400 can include one or more porous and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the one or more polymers that at least partially form layer 412 and/or the one or more needles or micro-needles 400 include a non-porous polymer to at least partially control a rate of release by molecular diffusion of the one or more biological agents that are mixed with the polymer. The inclusion of one or more biological agents in the one or more needles or micro-needles can provide controlled release of biological agent in the treatment area (e.g., body passageway, etc.) after insertion of the stent; however, this is not required. The use of one or more biological agents to form layer 412 and/or one or more needles or micro-needles 400 can provide a burst of one or more biological agent in the treatment area (e.g., body passageway, etc.) after insertion of the stent; however, this is not required.

Figure 15:
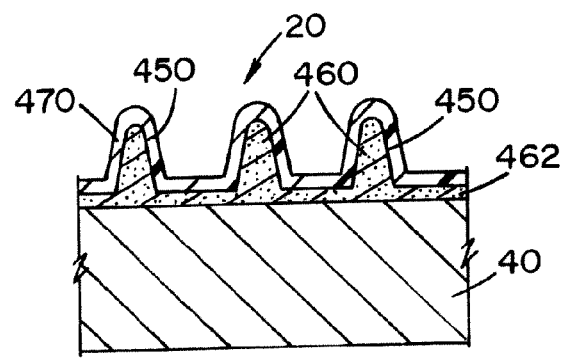
FIG. 15 is a cross-sectional view along line 2-2 of FIG. 1 illustrating micro-needles on the surface of the medical device that are formed of a biological agent and coated with a polymer.

Referring now to FIG. 15. FIG. 15 is a modification of the arrangement illustrated in FIG. 13. In FIG. 15, a coating 470, that is formed of one or more polymers and/or biological agents is placed over one or more needles or micro-needles 450 and layer 462. Specifically, the base structure 40 of stent 20 includes one or more needles or micro-needles 450. The one or more needles or micro-needles are formed on the surface of the base structure. The one or more needles or micro-needles are formed from one or more biological agents and/or polymers 460. A layer 462 of biological agent and/or polymer is also formed on the surface of the base structure. The composition of layer 462 and one or more needles or micro-needles can be the same or different. In one non-limiting example, the one or more biological agents that can at least partially form layer 462 and/or one or more needles or micro-needles 450 include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives. GM-CSF, GM-CSF derivatives, or combinations thereof. The one or more polymers that can at least partially form layer 462 and or one or more needles or micro-needles include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA. POE, PGA, PLLA, PAA, PEG, chitosan and or derivatives of one or more of these polymers. In one non-limiting example, the one or more polymers that can at least partially form layer 462 and/or one or more needles or micro-needles 450 include one or more non-porous polymer such as, but not limited to, parylene C, parylene N, parylene F and/or a parylene derivative. The one or more non-porous polymers can be used to at least partially control a rate of release by molecular diffusion of the one or more biological agents in layer 462 and or in the one or more needles or micro-needles 450; however, this is not required. Layer 470 that is coated on the top of the one or more needles or micro-needles and layer 462 includes one or more biological agents and/or polymers. In one non-limiting example, the one or more biological agents that can at least partially form layer 470 include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives. GM-CSF, GM-CSF derivatives, or combinations thereof. In one non-limiting example, the one or more polymers that can at least partially form layer 470 include one or more porous and or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. When the one or more polymers include one or more non-porous polymers, such non-porous polymer can include, but not limited to, parylene C, parylene N, parylene F and/or a parylene derivative. The one or more non-porous polymers can be used to at least partially control a rate of release by molecular diffusion of the one or more biological agents in layer 463, layer 470 and/or in the one or more needles or micro-needles 450; however, this is not required. When one or more biological agents at least partially form layer 470 and/or are coated on layer 470, not shown, the one or more biological agents can provide a burst of one or more biological agent in the treatment area (e.g., body passageway, etc.) after insertion of the stent; however, this is not required.

Figure 16:
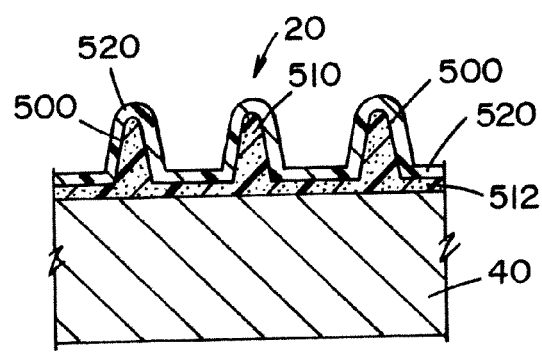
FIG. 16 is a cross-sectional view along line 2-2 of FIG. 1 illustrating micro-needles on the surface of the medical device that are formed of a biological agent and polymer and coated with a polymer.

Referring now to FIG. 16, FIG. 16 is a modification of the arrangement illustrated in FIG. 12. In FIG. 16, a coating 520, that is formed of one or more polymers and/or biological agents is placed over one or more needles or micro-needles 500 and layer 512. The composition of layer 520 and layer 512 and/or one or more needles or micro-needles can be the same or different. Specifically, the base structure 40 of stent 20 includes one or more needles or micro-needles 500. The one or more needles or micro-needles are formed on the surface of the base structure. The one or more needles or micro-needles are formed from a mixture of one or more biological agents and one or more polymers 510. A layer 512 of biological agent and polymer is also formed on the surface of the base structure. As can be appreciated, layer 512 and/or one or more needles or micro-needles 500 can be formed only of one or more polymers or one or more biological agents. The composition of layer 512 and one or more needles or micro-needles 500 can be the same or different. In one non-limiting example, the one or more biological agents that can at least partially form layer 512 and/or one or more needles or micro-needles 500 include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The one or more polymers that can at least partially form layer 512 and/or one or more needles or micro-needles 500 include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the one or more polymers that can at least partially form layer 512 and/or one or more needles or micro-needles 500 include one or more non-porous polymers such as, but not limited to, parylene C, parylene N, parylene F and/or a parylene derivative. The one or more non-porous polymers can be used to at least partially control a rate of release by molecular diffusion of the one or more biological agents in layer 512 and/or in the one or more needles or micro-needles 500; however, this is not required. In one non-limiting example, the one or more polymers that can at least partially form layer 520 include one or more porous and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. When the one or more polymers include one or more non-porous polymers, such non-porous polymer can include, but not limited to, parylene C, parylene N, parylene F and/or a parylene derivative. The one or more non-porous polymers can be used to at least partially control a rate of release by molecular diffusion of the one or more biological agents in layer 512, layer 520 and/or in the one or more needles or micro-needles 500, however, this is not required. When one or more biological agents at least partially form layer 520 and/or are coated on layer 520, not shown, the one or more biological agents can provide a burst of one or more biological agent in the treatment area (e.g., body passageway, etc.) after insertion of the stent; however, this is not required.

Figure 17:
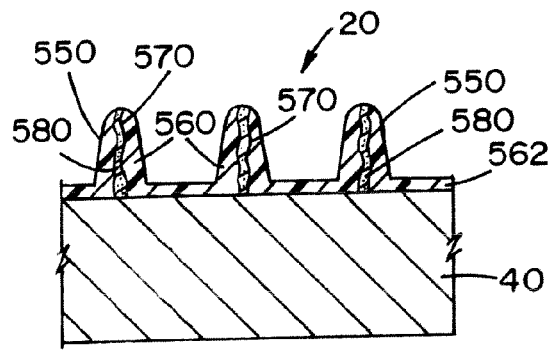
FIG. 17 is a cross-sectional view along line 2-2 of FIG. 1 illustrating micro-needles on the surface of the medical device that are formed of a polymer and includes an internal cavity that includes a biological agent.

Referring now to FIG. 17, FIG. 17 is another modification of the arrangement illustrated in FIG. 12. In FIG. 17, one or more internal channels 570 are formed in one or more needles or micro-needles 550. The one or more internal channels 570 can include one or more biological agent and/or polymers. Specifically, the base structure 40 of stent 20 includes one or more needles or micro-needles 550. The one or more needles or micro-needles are formed on the surface of the base structure. The one or more needles or micro-needles are formed from one or more polymers and/or biological agents 560. A layer 562 of polymer and/or biological agent is also formed on the surface of the base structure. The composition of layer 562 and one or more needles or micro-needles can be the same or different. The one or more polymers that can at least partially form layer 562 and/or one or more needles or micro-needles 550 include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the one or more polymers that can at least partially form layer 562 and/or one or more needles or micro-needles 550 include one or more non-porous polymers such as, but not limited to, parylene C, parylene N, parylene F and/or a parylene derivative. The one or more non-porous polymers can be used to at least partially control a rate of release by molecular diffusion of the one or more biological agents in layer 562, in the one or more needles or micro-needles 550, and/or in one or more internal channels 570; however, this is not required. One or more of the needles or micro-needles 550 include an internal channel 570. The internal channel is illustrated as including one or more biological agents 580; however, it can be appreciated that one or more channels can include a mixture of one or more polymers and or biological agents, or only one or more polymers. In one non-limiting example, the one or more biological agents includes trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The top opening of the channel enables delivery of one or more biological agents directly into treatment area (e.g., a wall of a body passageway or organ, etc.). The one or more biological agents in internal channel 570 can pass through and or molecularly diffuse through the one or more polymers that at least partially form the one or more needles or micro-needles; however, this is not required. The release of the one or more biological agents through the one or more polymers that at least partially form the one or more needles or micro-needles can be a controlled or an uncontrolled release rate. As can be appreciated, a layer of biological agent, not shown, can be coated one or more needles or micro-needles 550. The layer of biological agent could include one or more biological agents. The placement of the layer of biological agent on the one or more needles or micro-needles 550 can provide a burst of one or more biological agents in the treatment area; however, this is not required. As can be appreciated, other combinations of polymer layer and/or layer of biological agent can be used on the stent. As can also or alternatively be appreciated, a layer of polymer, not shown, can be coated one or more needles or micro-needles 550. The layer of polymer could include one or more polymers. The placement of the layer of polymer on the one or more needles or micro-needles 550 can be used to a) at least partially control a release rate of one or more biological agents from the stent, and/or 2) provide structural support and or protection to one or more needles or micro-needles. As can be appreciated, the polymer layer, when used, can have other or additional functions. These other combinations are also encompassed within the scope of the present invention.

Figure 18:
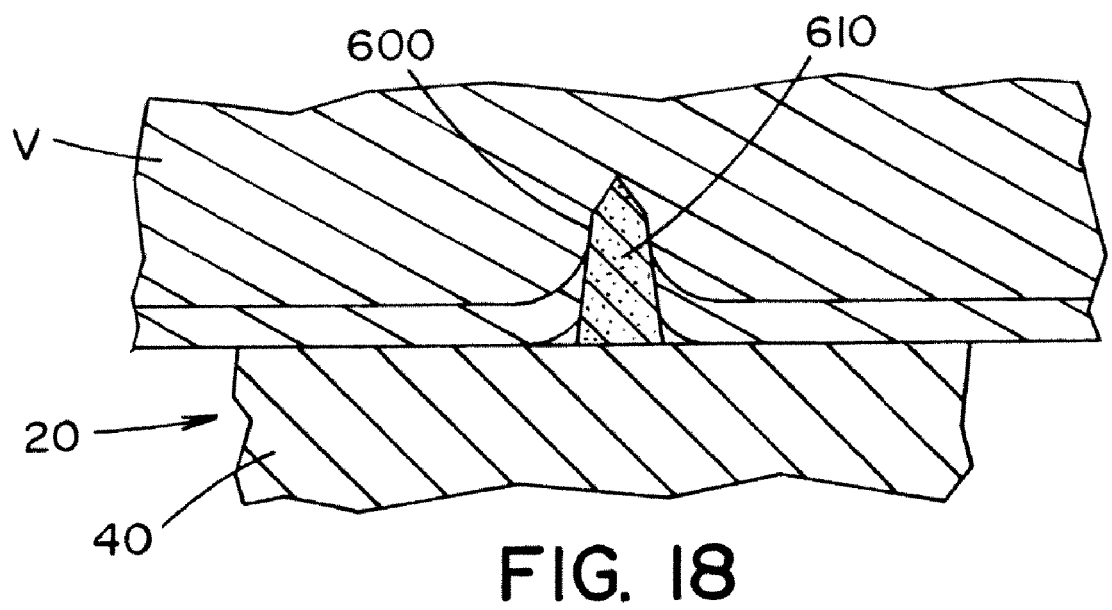
FIG. 18 is a cross-sectional view of a micro-needle that is penetrating into the inner surface of a body passageway or organ; and, FIG. 19 is one non-limiting process in accordance with the invention for manufacturing a stent from a molybdenum and rhenium alloy.

Referring now to FIG. 18, there is illustrated an enlarged portion of a surface of a stent 20 which includes a surface needle, micro-needle or other type of structure or microstructure 600. The needle is shown to include at least one biological agent 610; however, the needle can also or alternatively include one or more polymers, adhesives, etc. The stent, when in the form of a stent, is illustrated as being in an expanded state. When the stent is inserted or expanded in a treatment area, the needle 600 on the outer surface of the stent engages and/or at least partially penetrates into blood vessel or organ V. When the needle includes one or more biological agents, the one or more biological agents are at least partially locally applied to a treatment area. This can be a significant advantage over system wide treatment with one or more biological agents. The locally treatment with one or more biological agent via the needle can more effectively and/or efficiently direct the desired agents to a treated area. The release of one or more biological agents from the needle can be controlled, if desired, to direct the desired amount of one or more biological agents to a treated area over a desired period of time. When the stent is expanded in a blood vessel, the one or more needles enable local delivery of one or more biological agents into the wall of the blood vessel. This local delivery is especially advantageous in large and/or thick blood vessels wherein system wide drug treatment is not very effective. In addition, the local delivery of biological agent by the needle directly into the blood vessel can be more effective than only releasing the biological agent from the surface of the stent since diffusion from the surface of the stent to the larger and/or thicker blood vessel may not be as effective as direct delivery by the needles to the blood vessel. The one or more needles on the stent surface can also or alternatively be used to facilitate in securing the stent to the treatment area during the expansion and/or insertion of the stent in a treatment area.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween.

We claim:

1. A medical device at least partially formed of a metal alloy which improves the strength and radiopacity of the medical device, said metal alloy including at least about 95 weight percent of a solid solution of rhenium and molybdenum, said metal alloy including 40-55 weight percent rhenium and 45-60 weight percent molybdenum, said metal alloy including carbon, nitrogen and oxygen, said metal alloy having a nitrogen content of less than about 20 ppm, a carbon content of less than about 150 ppm, and an oxygen content of less than about 75 ppm, said metal alloy having a carbon to oxygen atomic ratio of at least about 1:1, said metal alloy having a carbon to oxygen atomic ratio of less than about 50:1, at least one region of said medical device including biological agent, polymer, micro-structure, or combinations thereof.

2. The medical device as defined in claim 1, wherein said metal alloy has an average yield strength of at least about 95 ksi and an average ultimate tensile strength of at least about 95 ksi, said metal alloy having an average grain size of over 5 ASTM, and said metal alloy having an average tensile elongation of at least about 25%.

3. The medical device as defined in claims 1 or 2, wherein said medical device is a stent, graft, valve, screw, nail, rod, PFO device, prosthetic device, sheath, guide wire, balloon catheter, hypotube, catheter, electrophysiology catheter, staple or cutting device.

4. The medical device as defined in claim 1, wherein said metal alloy includes over 99 weight percent of a solid solution.

5. The medical device as defined in claim 4, wherein said metal alloy includes at least about 99.95 weight percent of a solution.

6. The medical device as defined in claim 1, wherein said metal alloy has an average density of at least 10 gm/cc.

7. The medical device as defined in claim 5, wherein said metal alloy has an average density of at least 10 gm/cc.

8. The medical device as defined in claim 1, wherein said metal alloy includes about 46-49 weight percent rhenium and about 51-54 weight percent molybdenum.

9. The medical device as defined in claim 7, wherein said metal alloy includes about 46-49 weight percent rhenium and about 51-54 weight percent molybdenum.

10. The medical device as defined in claim 1, wherein said metal alloy includes about 40-50 weight percent rhenium and about 50-60 weight percent molybdenum.

11. The medical device as defined in claim 7, wherein said metal alloy includes about 40-50 weight percent rhenium and about 50-60 weight percent molybdenum.

12. The medical device as defined in claim 1, wherein said carbon content of said metal alloy is less than about 100 ppm and said oxygen content of said metal alloy is less than about 50 ppm, and a carbon to oxygen atomic ratio of at least about 2:1.

13. The medical device as defined in claim 9 or 11, wherein said carbon content of said metal alloy is less than about 100 ppm and said oxygen content of said metal alloy is less than about 50 ppm, and a carbon to oxygen atomic ratio of at least about 2:1.

14. The medical device as defined in claim 12, wherein said carbon content of said metal alloy is less than about 50 ppm and said oxygen content of said metal alloy is less than about 10 ppm.

15. The medical device as defined in claim 13, wherein said carbon content of said metal alloy is less than about 50 ppm and said oxygen content of said metal alloy is less than about 10 ppm.

16. The medical device as defined in claim 1, wherein said atomic ratio of carbon to oxygen in said metal alloy is up to about 20:1.

17. The medical device as defined in claim 15, wherein said atomic ratio of carbon to oxygen in said metal alloy is up to about 20:1.

18. The medical device as defined in claim 1, wherein said nitrogen content of said metal alloy is less than about 10 ppm.

19. The medical device as defined in claim 17, wherein said nitrogen content of said metal alloy is less than about 10 ppm.

20. The medical device as defined in claim 1, wherein said metal alloy has an average grain size of about 5-10 ASTM.

21. The medical device as defined in claim 19, wherein said metal alloy has an average grain size of about 5-10 ASTM.

22. The medical device as defined in claim 1, wherein said metal alloy comprises by weight percent:

| | |
|---|---|
| C | <150 ppm |
| Mo | 51-56% |
| O | <50 ppm |
| N | <20 ppm |
| Re | 44-49% | and has an average grain size of about 6-8 ASTM, an average tensile elongation of about 25-35%, and said content of rhenium plus molybdenum is at least about 99.9 weight percent.

23. The medical device as defined in claim 21, wherein said metal alloy comprises by weight percent:

| | |
|---|---|
| C | <150 ppm |
| Mo | 51-56% |
| O | <50 ppm |
| N | <20 ppm |
| Re | 44-49% | and has an average grain size of about 6-8 ASTM, an average tensile elongation of about 25-35%, and said content of rhenium plus molybdenum is at least about 99.9 weight percent.

24. The medical device as defined in claim 1, wherein said metal alloy comprises by weight percent:

| | |
|---|---|
| C | <50 ppm |
| Mo | 52.5-55.5% |
| O | <10 ppm |
| N | <10 ppm |
| Re | 44.5-47.5% | and has an average grain size of about 6-7 ASTM, and an average tensile elongation of about 25-35%, and said content of rhenium plus molybdenum is at least about 99.9 weight percent.

25. The medical device as defined in claim 21, wherein said metal alloy comprises by weight percent:

| | |
|---|---|
| C | <50 ppm |
| Mo | 52.5-55.5% |
| O | <10 ppm |
| N | <10 ppm |
| Re | 44.5-47.5% | and has an average grain size of about 6-7 ASTM, and an average tensile elongation of about 25-35%, and said content of rhenium plus molybdenum is at least about 99.9 weight percent.

26. The medical device as defined in claim 1, wherein said metal alloy comprises by weight percent:

| | |
|---|---|
| C | <50 ppm |
| Mo | 52.5% |
| O | <10 ppm |
| N | <10 ppm |
| Re | 47.5% | and has an average grain size of about 6-7 ASTM, and an average tensile elongation of about 25-35%, and said content of rhenium plus molybdenum is at least about 99.9 weight percent.

27. The medical device as defined in claim 21, wherein said metal alloy comprises by weight percent:

| | |
|---|---|
| C | <50 ppm |
| Mo | 52.5% |
| O | <10 ppm |
| N | <10 ppm |
| Re | 47.5% | and has an average grain size of about 6-7 ASTM, and an average tensile elongation of about 25-35%, and said content of rhenium plus molybdenum is at least about 99.9 weight percent.

28. The medical device as defined in claim 1, wherein said metal alloy including an additional metal, said additional metal constituting less than about 10 weight percent of said metal alloy, said additional metal including one or more metals selected from the group consisting of titanium, yttrium, and zirconium.

29. The medical device as defined in claim 21, wherein said metal alloy including an additional metal, said additional metal constituting less than about 10 weight percent of said metal alloy, said additional metal including one or more metals selected from the group consisting of titanium, yttrium, and zirconium.

30. The medical device as defined in claim 28, wherein said titanium content is less than about 1 weight percent of said metal alloy, said yttrium content is less than about 0.3 weight percent of said metal alloy, and said zirconium content is less than about 0.5 weight percent of said metal alloy.

31. The medical device as defined in claim 29, wherein said titanium content is less than about 1 weight percent of said metal alloy, said yttrium content is less than about 0.3 weight percent of said metal alloy, and said zirconium content is less than about 0.5 weight percent of said metal alloy.

32. The medical device as defined in claim 28, wherein said metal alloy includes titanium and zirconium, said titanium and zirconium having a weight ratio of about 1-10:1.

33. The medical device as defined in claim 31, wherein said metal alloy includes titanium and zirconium, said titanium and zirconium having a weight ratio of about 1-10:1.

34. The medical device as defined in claim 1, wherein said medical device includes polymer and biological agent, said polymer at least partially coating said biological agent, encapsulating said biological agent, and combinations thereof.

35. The medical device as defined in claim 21, wherein said medical device includes polymer and a biological agent, said polymer at least partially coating said biological agent, encapsulating said biological agent, and combinations thereof.

36. The medical device as defined in claim 1, wherein said medical device includes said polymer, said polymer includes one or more compounds selected from the group consisting of parylene, a parylene derivative, chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, and a PEG derivative.

37. The medical device as defined in claim 1, wherein medical device includes biological agent, said biological agent includes one or more compounds selected from the group consisting of trapidil, trapidil derivatives, taxol, taxol derivatives, cytochalasin, cytochalasin derivatives, paclitaxel, paclitaxel derivatives, rapamycin, rapamycin derivatives, GM-CSF, and GM-CSF derivatives.

38. The medical device as defined in claim 1, wherein said medical device includes said micro-structure on an outer surface of said medical device.

39. The medical device as defined in claim 38, wherein said at least one micro-structure is at least partially formed of, includes, or combinations thereof, a material comprising a said polymer, said biological agent, and combinations thereof.

40. A stent that is formed of at least about 80 weight percent of a metal alloy which improves the strength and ductility of the stent, said metal alloy including at least about 99.9 weight percent of a solid solution of rhenium and molybdenum, said metal alloy including carbon and oxygen and having a carbon to oxygen atomic ratio of at least about 1:1 and less than about 50:1, said metal alloy having an average yield strength of about 98-122 ksi and an average ultimate tensile strength of about 100-150 ksi, said metal alloy having an average grain size of about 6-9 ASTM, said metal alloy having an average tensile elongation of about 25-35%, at least one region of said medical device including biological agent, polymer, micro-structure, or combinations thereof, said medical device including by weight percent:

| | |
|---|---|
| C | <150 ppm |
| Mo | 51-56% |
| O | <50 ppm |
| N | <20 ppm |
| Re | 44-49%. |

41. The stent as defined in claim 40, wherein said metal alloy comprises by weight percent:

| | |
|---|---|
| C | <50 ppm |
| Mo | 52.5-55.5% |
| O | <10 ppm |
| N | <10 ppm |
| Re | 44.5-47.5% | and an average grain size of about 6-7 ASTM.

42. The stent as defined in claim 40, wherein said metal alloy including an additional metal, said additional metal constituting less than about 10 weight percent of said metal alloy, said additional metal including one or more metals selected from the group consisting of titanium, yttrium, and zirconium, said titanium content is less than about 1 weight percent of said metal alloy, said yttrium content is less than about 0.3 weight percent of said metal alloy, and said zirconium content is less than about 0.5 weight percent of said metal alloy.

43. The stent as defined in claim 41, wherein said metal alloy including an additional metal, said additional metal constituting less than about 10 weight percent of said metal alloy, said additional metal including one or more metals selected from the group consisting of titanium, yttrium, and zirconium, said titanium content is less than about 1 weight percent of said metal alloy, said yttrium content is less than about 0.3 weight percent of said metal alloy, and said zirconium content is less than about 0.5 weight percent of said metal alloy.

44. A medical device at least partially formed of a metal alloy which improves the strength and radiopacity of the medical device, said metal alloy including at least about 95 weight percent of a solid solution of rhenium and molybdenum, said metal alloy including at least 40 weight percent rhenium and at least 40 weight percent molybdenum, said metal alloy including carbon, nitrogen and oxygen, said metal alloy having a nitrogen content of less than about 30 ppm, a carbon content of up to 200 ppm, and an oxygen content of up to 100 ppm, said metal alloy having a carbon to oxygen atomic ratio of at least about 1:1, said metal alloy having a carbon to oxygen atomic ratio of less than about 50:1, said metal alloy having an average yield strength of at least about 70 ksi and an average ultimate tensile strength of about 80-150 ksi, said metal alloy having an average grain size of over 5 ASTM, said metal alloy having an average tensile elongation of at least about 25%, at least one region of said medical device including biological agent, polymer, microstructure, or combinations thereof.

* * * * *